United States Patent
Chandra-Mody

(10) Patent No.: US 10,786,424 B1
(45) Date of Patent: Sep. 29, 2020

(54) EXPERT ASSOCIATIONS-BASED TREATMENT SYSTEM FOR REDUCING TISSUE DAMAGE FROM REPERFUSION INJURY

(71) Applicant: Stroma Physical Therapy, New York, NY (US)

(72) Inventor: Vinita Chandra-Mody, New York, NY (US)

(73) Assignee: Stroma Physical Therapy, New York, NY (US)

( * ) Notice: Subject to any disclaimer, the term of this patent is extended or adjusted under 35 U.S.C. 154(b) by 68 days.

(21) Appl. No.: 16/045,201

(22) Filed: Jul. 25, 2018

Related U.S. Application Data

(60) Provisional application No. 62/536,629, filed on Jul. 25, 2017.

(51) Int. Cl.
| | |
|---|---|
| *G06T 11/00* | (2006.01) |
| *A61H 23/06* | (2006.01) |
| *A61B 5/00* | (2006.01) |
| *G16H 20/30* | (2018.01) |
| *A61H 37/00* | (2006.01) |

(52) U.S. Cl.
CPC ........... *A61H 23/06* (2013.01); *A61B 5/4519* (2013.01); *A61B 5/4523* (2013.01); *G16H 20/30* (2018.01); *A61H 37/00* (2013.01)

(58) Field of Classification Search
CPC ................ G06Q 50/2057; G06Q 10/10; G06F 21/6218; G06F 3/0623; G06F 16/212; G06F 9/547; G06T 7/20; G06T 1/20
USPC .......................... 382/128, 162; 705/2; 707/10
See application file for complete search history.

(56) References Cited

U.S. PATENT DOCUMENTS

| | | | | |
|---|---|---|---|---|
| 8,566,115 B2 * | 10/2013 | Moore | .................. | G06F 19/325 705/2 |
| 2009/0254572 A1 * | 10/2009 | Redlich | .................. | G06Q 10/06 |

* cited by examiner

*Primary Examiner* — Phuoc H Doan
(74) *Attorney, Agent, or Firm* — Fennemore Craig, P.C.

(57) ABSTRACT

An expert system facilitates non-surgical manual semi-occlusion method for treating Reperfusion Injury (RI). This technique involves a four phase framework: (1) palpating a soft tissue structure or segment of the body in order to bring blood flow to the area—called the "Touch"; (2) placing a contact point at the nearest proximal vascular branch that supplies the specific target structure and creating manual tension at a vector running 90° to the elongate axis of the artery to act as a manual tourniquet—called the "Activation"; (3) maintaining the vector of tension until a pulse is felt under the contact point and then waiting for the pulse to adequately diminish—herein called the "Pulse"; and (4) applying a stretch on the nerve that supplies the Structure or Segment, both locally and centrally, in order to occlude the blood supply to the nerve for 30 seconds—called the "Neurovascular Stretch."

43 Claims, 42 Drawing Sheets

| PREVENTION --302-- | TREAT:ACUTE --304-- | TREAT: SUB-ACUTE & CHRONIC --306-- |
|---|---|---|
| Preconditoning "Pre-C" | Ischemia "Per-C" | Postconditioning "Post-C" |

FIG. 3

| | | |
|---|---|---|
| | S⁵ --804-- | 1.1.9 FEMORAL: PECTINEUS --802-- |
| --A-- | T --804-- | --808--<br>Origin – Pecten Pubis and Pectineal surface of the pubis<br><br>Insertion – Pectineal line of femur<br><br>Blood Supply – Muscular Branches of the Femoral Artery<br><br>Innervation – Femoral Nerve |
| --B-- | A --806-- | HP1 – Femoral Artery at Scarpa's Triangle (Pectineus) --808--<br><br>Vector = _Posterior_ (medial)<br><br>HP2 – Femoral Pulse at Adductor Hiatus --810-- ♡--812-- |
| --C-- | P --814-- | Mody Pulse @ Femoral Artery at Scapa's Triangle |
| --D-- | N --816-- | Local Stretch – Femoral Nerve: Supine/Hip Extension and Internal Rotation/Knee Flexion/Ankle Plantarflexion<br><br>Central Stretch – Dura: Head Flexion and Contralateral Knee Flexion |

FIG. 8

| Precautions | Contraindications |
|---|---|
| • Age<br>• Gender<br>• Pregnancy<br>• Family History of Cardiovascular Disease<br>• Sedentary<br>• Diabetes<br>• Cholesterol<br>• Hypotension or Hypertension<br>• Smoking<br>• Stress<br>• Obesity<br>• Prior hospitalization and surgeries<br>• Medications<br>• Laboratory results and diagnostic imaging<br>• Mood Disorders or Poor Sleep Habits<br>• Congenital Heart Defects<br>• Shortness of Breath<br>• Burning, Wheezing and Coughing in Chest<br>• Foreign implants<br>• Osteopenia or Osteoporosis<br>• An old brain injury or stroke<br>• Excessive joint swelling<br>• Peripheral neuropathies<br>• Acute or chronic skin infection<br>• Thermoregulatory issues<br>• Dermatological trauma<br>• Varicosities<br>• Endocrine, Metabolic Diseases<br>• Raynaud's, RA, Lupus, Connective Tissue Disorders, Lymphatic Disorders<br>• Anemia and bruising easily<br>• Hiatal hernia<br>• Recurrent Tonsillitis<br>• Eating Disorders<br>• Nausea and Vomiting | • Medications that lead to weakening of bone and connective tissue and/or excessive bleeding<br>• Incapacity or Failure to Consent<br>• Long-term addiction or substance abuse<br>• Coronary Arterial Disease (CAD)<br>• Peripheral Arterial Disease (PAD)<br>• Atherosclerosis<br>• Arteriosclerosis<br>• Coronary, Arterial and Venous Insufficiency<br>• Congestive Heart Failure (CHF)<br>• Arterial Aneurysm<br>• Thrombus, Embolism, or DVT<br>• Arteriovenous Malformation<br>• Chest pain related to Angina<br>• Palpitations or Dysrhythmias<br>• Claudication<br>• Cardiovascular Hardware or Implant<br>• Vertebral Basilar Insufficiency (VBI)<br>• Cancer<br>• Lymphedema<br>• Current Fever or Infection<br>• Hematological and Blood Diseases<br>• Hematoma<br>• Severe Liver, Kidney or Bladder Diseases<br>• Severe Reproductive Organ Diseases<br>• Glaucoma |

FIG. 13

| | Taxonomy Code: (System) . (Segment) . (Structure) --1402-- |
|---|---|
| --1401-- $S^{xy}$ | |
| Touch/ Treatment --1404-- T | Provide any soft tissue palpation to a specific structure or group of structures that are found in one segment of the body in the taxonomy order, as defined by *ICT by Stroma*™ to attract blood flow to the area.<br>Origins, Insertions, Blood Supply and Innervations are listed. --1406-- |
| Activation (Occlusive Event #1) --1408-- A | Hand Placement 1 – Treating Hand; HP1 --1410--<br>Palpate the proximal common artery for the segment and move ADJACENT to it. Provide 30sec-5min seconds of continuous compression X glide = Tension at 90 away from the artery being treated in order to semi-occlude it.<br>Tension at 90° Vector --1412--<br>The vector is indicated to optimize the tension at 90 degrees using the equation:<br>v = Compression(Glide); where the compression can occur in 1 and/or 2 planes and the glide can occur in 1 and/or 2 planes<br>Denotes Activation Points 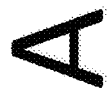 --1416--<br>Hand Placement 2-Assessing Hand or Treating Hand; HP2 --1414--<br>Place the second hand on an artery distal to the structure or group of structures that were treated to use as a comparison for the Chandra-Mody Pulse occurring at HP1 (assessing hand). May also be used as an activation point in the case of a double activation (treating hand).<br>Denotes Pulse Points  --1418--<br>(DA) Double Activation - HP2 acts as a second activation site proximal to the structure(s) being treated to improve the ischemic effect. In this case there will be 2 activation stars present.<br>(T) Terminal Branch - HP2 cannot be used on a distal artery since there is no distal point available. In this case there will be 1 activation star present. |

FIG. 14A

| | | |
|---|---|---|
| Pulse<br><br>--1420-- | P | At the end of the activation, a pulse phase is felt which begins with the first Chandra-Mody pulse. Chandra-Mody pulses at HP1 (and HP2 if a double activation is being used) are felt by the practitioner (and occasionally the patient) and determine the effectiveness of the hand placement and level of activation at an activation site. During the pulse phase, the practitioner has the option to move to the next step to enhance the ischemic effect.  --1422-- |
| Neurovascular Stretch (Occlusive Event #2)<br><br>--1424-- | N | To enhance the ischemic effect, stretch the neurovascular tissue that supply the treated segment to occlude the blood vessels supplying the nerve. Using the local stretch, hold for 30 seconds. If the patient can tolerate a deeper stretch, slowly perform the central stretch in conjunction with the local stretch during the 30 second period.  --1426-- |

VARIATIONS:
Combined Approach - TAPN is occurring simultaneously versus Separated Approach -- TAPN is occurring sequentially.
TAPN - The full procedure is used as the intervention and can be either combined or separated.
TAP - The touch/treatment, Activation and Chandra-Mody Pulse is used as the intervention.
AP - The Activation and the Chandra-Mody pulse is used as the intervention.
T - The touch/treatment follows the taxonomy of structures and segments and is used as the intervention and not occlusion.

| | |
|---|---|
| S³ --1504-- | 2.1.1 PECTORAL: PECTORALIS MAJOR |
| T --1506-- | Origin – Clavicular head: anterior border of the medial half of the clavicle. Sterno-costal head: anterior surface of the sternum, the superior six costal cartilages, and the aponeurosis of the external oblique muscle Insertion – Lateral lip of the bicipital groove of the humerus Blood Supply – Axillary Artery (Pectoral Branch) Innervation – Lateral Pectoral Nerve and Medial Pectoral Nerve |
| A --1508-- | HP1 – 2ⁿᵈ Section of Axillary Artery at Pectoralis Minor (Pectoralis Minor) Vector = _posterior(inferomedial)_ ✦ --1512-- HP2 - Brachial Pulse at Antecubital Fossa ♡ --1514-- |
| P --1516-- | Chandra-Mody Pulse @ 2ⁿᵈ Section Axillary Artery at Pectoral Tunnel |
| N --1516-- | Local Stretch – Pectoral Nerve: Shoulder Abduction to 120°, Elbow Extension, Forearm Supination, Wrist and Finger Extension Central Stretch – Dura: Contralateral Neck Side Flexion |

| | |
|---|---|
| $S^{1,2,5}$ --2004-- | 3.5.1 EXTRINSIC LUMBAR LATISSIMUS DORSI ORGIN |

| | |
|---|---|
| T<br>--2006-- | Origin – Spinous processes of vertebrae T7-L5, thoracolumbar fascia, iliac crest, inferior 3 or 4 ribs and inferior angle of scapula<br><br>Insertion – Inferior angle of scapula and floor of intertubercular groove of humerus<br><br>Blood Supply – Thoracodorsal Branch of Subscapular Artery and Lumbar Arteries<br><br>Innervation – Thoracodorsal Nerve |
| A<br>--2008-- | HP1 – Thoracodorsal Artery --2010--<br>(Latissimus Insertion at Inferior Angle of Scapula)<br>Vector = _anterior(medial)_ --2014--<br>HP2 – Lumbar arteries --2012--<br>(between the transverse processes of L1-L5)<br>Vector = _anterior(medial)_ --2016--<br>DA |
| P<br>--2018-- | Chandra-Mody Pulse @ Thoracodorsal Artery and Lumbar Arteries |
| N<br>--2020-- | Local Stretch – Thoracodorsal and Ventral Lumbar Rami Stretch: Hip Extension, Adduction and Internal Rotation, Contralateral Lumbar Rotation --2022--<br><br>Central Stretch – Dura: Ipsilateral Shoulder Flexion and Internal Rotation, Elbow Extension, Head Flexion --2024-- |

FIG. 20

| | 2500 |
|---|---|
| S³ --2504-- | 4.1.1 EXTRINSIC LUMBAR: OCCIPITALIS |
| T --2506-- | Origin – Superior nuchal line of occipital bones and mastoid processes<br>Insertion – Galea aponeurosis<br>Blood Supply – Occipital Artery<br>Innervation – Posterior Auricular Nerve |
| A --2508-- | HP1 – Occipital Artery at the Nuchal Line (Right) ✧ --2510--<br>(Nuchal Line of Occipital Bone) --2514--<br>Vector = *anterior(medial)*<br>HP2 – Occipital Artery at the Nuchal Line (Left) ✧ --2512--<br>(Nuchal Line of Occipital Bone)<br>Vector = *anterior(medial)* --2516--<br>DA |
| P --2518-- | Chandra-Mody Pulse @ Occipital Artery at Nuchal Line |
| T --2520-- | Local Stretch – Posterior Auricular Nerve Stretch<br>Bilaterally: Neck Flexion --2522--<br>Unilaterally: Contralateral Neck Rotation and Side Flexion, Neck Flexion<br>Central Stretch – Dura: Lumbar Flexion, Hip Flexion, Knee Flexion, Ankle Flexion (Reverse Child's Pose or Child's Pose) --2524-- |

FIG. 25

| | |
|---|---|
| S³ --3004-- | 5.1.B.1 SACRAL LIGAMENTS/ INFERIOR: SACROTUBEROUS LIGAMENT --3002-- |
| T --3006-- | Origin – Sacrum (the lower transverse sacral tubercles, the inferior margins of the sacrum and the upper coccyx<br>Insertion – Tuberosity of the ischium<br>Blood Supply – Inferior Gluteal Artery<br>Innervation – Pudendal Nerve |
| A --3008-- | HP1 – Inferior Gluteal Artery Inferior to the Piriformis (Piriformis) --3010--<br>Vector = _medial(inferoposterior)_ --3014--<br>HP2 – Superior Lateral Sacral Artery --3012--<br>(Posterior Sacral Foramen 1 and 2 of Sacrum)<br>Vector = _anterior(medial)_--3016--<br>DA |
| P --3018-- | Chandra-Mody Pulse @ Inferior Gluteal Artery and Lateral Sacral Artery |
| T --3020-- | Local Stretch – Pudendal Nerve Stretch: Side lying/Hip Adduction and External Rotation/Knee Flexion/Ankle Inversion --3022--<br><br>Central Stretch – Dura: Head Flexion and Contralateral Hip Extension and External Rotation/Knee Flexion --3024-- |

EXPERT ASSOCIATIONS-BASED TREATMENT SYSTEM FOR REDUCING TISSUE DAMAGE FROM REPERFUSION INJURY

RELATED APPLICATIONS

This application claims benefit of priority to U.S. provisional application Ser. No. 62/536,629 filed Jul. 25, 2017, which is hereby incorporated by reference to the same extent as though fully replicated herein.

BACKGROUND

Field

The presently disclosed instrumentalities relate to physical therapy and, more particularly, systems utilizing occlusion to reduce tissue damage from reperfusion injury ("RI").

Description of the Related Art

RI constitutes inflammatory and oxidative tissue damage caused by a re-supply of blood after a sustained period of ischemia. The absence of oxygen and nutrients from blood during the ischemic period creates a condition in which the restoration of circulation results in inflammation and oxidative tissue damage through the induction of Reactive Oxygen Species (ROS) rather than restoration of normal function. FIG. 2 shows a sequence of events or steps that occur in RI regardless of tissue type. Ischemia, 201, leads to cellular events, specifically the decrease in intracellular pH, 202. When tissue is reperfused by blood carrying oxygen, 204, this creates ROS 203, also known as free radicals, which result in direct cellular damage, 206 together with induction of an inflammatory cascade via the mitochondria 208, 209. Eventually, the cascade results cellular death by apoptosis 210.

FIG. 5 is reproduced from Knight, K. L. (1995). Cryotherapy in sports injury management. Champaign, Ill.: Human Kinetics. FIG. 5 shows the damage to surrounding healthy tissue from ischemia as secondary hypoxic injury 509. A primary trauma 501 directly damages tissues. In response to this primary injury, blood vessels, 502, muscles and connective tissues, 503, and nerves, 504, are secondarily affected, resulting in hemostasis of the clotting cascade 507, increased blood viscosity 512, from the inflammatory response, 511, edema 513, pain 514, and spasm 515 from hematoma formation 510. These problems all result in decreased delivery of oxygen and blood flow, i.e., ischemia, in the vicinity of the primary injury 508. Ischemia in surrounding healthy tissue resulting from these events may trigger the same pathway shown in FIG. 2 and may also cause eventual death of healthy tissues due to the presence of ROS.

Reperfusion injury may be characterized as an ischemic reperfusion cycle or I/R cycle. Counterintuitively, it has been medically proven that providing brief transient bouts of occlusion (or ischemia, which are used interchangeably) may reduce damage from RI to organs and other types of tissue. This type of treatment is known in the art as Ischemic Conditioning (IC). Cryotherapy studies have also proven the beneficial effects of the use of ice on acute injuries. Ice is a vasoconstrictor that helps reduce blood flow to a specific injury site and helps moderate swelling and other pro-inflammatory effects. As one can imagine that occlusion is a method of providing "internal ice", and occluding blood vessels as an intervention is justified in the treatment of acute and soft tissue musculoskeletal injuries.

Currently the field of medicine has known about the beneficial effects of occlusion in treating reperfusion injury (RI) in organs for the past 75 years. In the past 30 years, more research has been shedding light on the innate healing mechanism that is triggered in mammals from ischemic conditioning. Studies have demonstrated there is a benefit to conditioning tissue by use of brief transient bouts of occlusion at different points in time in relationship to the ischemic injury itself (Murry et al. (1986), Pryzyklenk et al. (1993), Wei et al. (2011), Zhao et al. (2012), Kocman et al. (2015)). As demonstrated in FIG. 3, if the intervention is applied prior to the ischemia, this is called Pre-Conditioning (Pre-C), 301, which is a form of prevention. If the intervention is applied during the injury, this is called Per-Conditioning (Per-C), 302, which treats acute injury. Finally, if the intervention is applied after the injury, this is called Post-Conditioning (Post-C), 303, and treats subacute and chronic injuries.

Although occlusion therapy has been investigated and rests on established scientific principles, the art has not advanced very far beyond the investigatory stage despite the passage of years. The art has not recognized, nor has it solved, the following problems within the field of ischemic conditioning:

- Currently, there is no full body manual technique that exists to treat sport and musculoskeletal soft tissue reperfusion injuries using occlusion and ischemic conditioning as its basis.
- There has been very little innovation with respect to how ischemia is provided as the intervention in ischemic conditioning. Conventional medicine has used sphygmomanometers or pressure cuffs, and clamps to occlude major blood vessels such as the femoral artery and brachial artery, in ischemic conditioning models. However, the use of the sphygmomanometer or clamps as a tourniquet risks damage to both arterial and neural tissues and has side effects. There is no other technique that uses manual pressure to simulate the ischemic effect.
- Currently, there is no semi-occlusive method being utilized despite evidence that demonstrates a reduction of tissue damage from RI.
- Currently, there is no technique that utilizes an additional ischemic effect on the vascular supply to neural structures.

SUMMARY

The presently disclosed instrumentalities overcome the problems outlined above and advance the art by providing a system that facilitates occlusion in treating reperfusion injury throughout the body. This is done by use of a hierarchically organized system that serves as a taxonomic guide for training and clinical reference that facilitates various clinical modalities as physical therapy techniques for the treatment and mitigation of reperfusion injuries. The system may be implemented, for example, as content that is organized and made searchable using a computer. Using occlusion or ischemia, the system aims to reduce damage to musculoskeletal tissue using a hands-on technique that is guided by an expert system of rules or associations, rather than tourniquets or clamps.

According to none embodiment, the system may be used to guide practitioners in prevention and treatment of patients afflicted by musculoskeletal soft tissue injuries due to reperfusion injury. A database contains images of taxonomically classified hand placements for treatment of reperfusion injury at one or more structures of interest in a human body. The database also contains descriptive information categorizing use of the hand placement as shown in the images into a framework including how to perform component actions of the treatment. These components may include: (1) touching (T) the one or more structures of interest to attract blood flow; (2) activating (A) occlusive treatment by creating a semi-occlusive manual tourniquet at an artery that supplies blood to the one or more structures of interest; (3) ascertaining effectiveness of the semi-occlusive manual tourniquet by determining a shift in volume and/or rate of a pulse (P) at the hand placement; and (4) stretching a portion of the human body to occlude blood flow to a nerve (N) segment of the human body by elongation of the nerve segment. The database also contains a system of data associations established by the application of expert guidance that facilitates reporting and selection of the taxonomically classified images and the descriptive information. A processor is equipped with program logic for a diagnostic query engine utilizing user input to access the system of expert rules or associations as an aid used in reporting to select and organize the images and the descriptive information in a report that demonstrates a modality of treating reperfusion injury at the structures of interest. A graphical user interface is configured to present the report for use in performing the modality of treatment.

In one aspect, the images of the report produced by the system may show the neural stretching component of the treatment being performed sequentially after activation of the artery called the separated approach. Alternatively, the images may show the neural stretching component of the treatment being performed simultaneously in a combined approach that conducts the stretch at the same time as activation of the treatment.

In one aspect, the images show the stretch occurring locally to stretch the nerve locally by movement of the nerve as elongated by movement of the body under the activating hand placement. The images may also show the stretch occurring centrally to further elongate the nerve by motion that is not occurring proximate the hand placement.

In one aspect, the images are taxonomically classified by use of a three-element code corresponding to Systems as divisions of the human body, Segments as divisions of a particular System, and Structures forming the structures of interest in the human body. The codes may be, for example, numeric or alphanumeric. A structure is a part of the human body that is susceptible to reperfusion injury. Structures may include, without limitation, muscles, tendons, ligaments, fascia, skin, fibrous tissues, connective tissue, fat synovial membrane, bone, nerves, blood vessels, glands, ducts and/or organs.

In one aspect, the descriptive information of the database may provide origins, insertions, blood supply and innervation of the proposed treatment in order to facilitate proper hand placement.

In one aspect, the hand placement may be a single activation utilizing one hand for activation. Alternatively, the hand placement may be a double activation utilizing two hands for activation.

In various aspects, the specific treatments may include, for example, those addressing a groin pull, pectoral strain, neck pain, lower back pain, or a sacral sprain.

In one aspect, the images of the report may include a combination of hand placements shown on medical illustrations and photographs demonstrating the modality in application.

In one aspect, the program logic may be user-selectively configurable for operation in a state selected from the group consisting of treating patients and training practitioners. The program logic may also include modules for subscription access management, and for patient monitoring across multiple therapy sessions to provide patient monitoring data. The system of expert rules or associations may access the patient monitoring data to assist selection of one or more additional treatment modalities in a follow-on treatment session. The associations may be established, for example, in a lookup table of as an element in a database relating a Segment or Structure of the human body to information that provides guidance in implementing a modality of treating or preventing RI in the Segment or Structure. The information may include, for example, anatomical diagrams, drawings, images, photographs and descriptive information demonstrating proper hand placement and hand motion for the occlusive technique.

The aforementioned system is useful in facilitating treatments of a human body including component aspects of touch, activation, pulse and nerve stretch performed according to a report produced by the system. The method includes: (1) touching (T) one or more structures of interest in the human body to thereby attract blood flow; (2) activating (A) or occluding treatment by creating a semi-occlusive manual tourniquet at an artery that supplies blood to the one or more structures of interest; (3) ascertaining effectiveness of the semi-occlusive manual tourniquet by determining a shift in volume and/or rate of a pulse (P) at the hand placement; and (4) stretching a portion of the human body to occlude blood flow to a nerve segment of the human body by elongation of the nerve segment locally and/or centrally.

In treating ischemic injury, tissue structure and function may be preserved by 30-60% if ischemic conditioning is applied during injury in a variety of organs and tissue such as the heart, brain, kidneys, liver, lungs, pancreas, GI tract and musculoskeletal tissue. Studies are demonstrating many more tissue types that may benefit from this type of intervention. The system may be applied in all three scenarios of musculoskeletal injury (Pre-C, Per-C, and Post-C), as RI is occurring in basic soft tissue trauma due to the resulting ischemia in surrounding healthy tissues as indicated in the secondary injury model. In fact, tendinopathies, sprains and osteoarthritis are all implicating RI as a part of the pathogenesis of these conditions (Farrell et al (1993), Toumi et al (2003), Bestwick et al. (2004), Findlay et al. (2007)).

Using current research, the presently disclosed system utilizes an expert system of rules or associations for directing non-surgical semi-occlusive manual manipulation at specific arterial sites throughout the body followed by a neurovascular stretch to further occlude the blood vessels surrounding the nerves to a specific segment or structure of the body as a novel method of ischemic conditioning. The treatment is facilitated by the use of data that is reported from a database that is taxonomically organized to associate Segments or Structures of the human body with instructions or other data that is useful for RI treatment. In one aspect, the reports form an anatomical guide that facilitates ischemic conditioning to treat RI by in phases that may be summarized by the acronym TAPN for Touch/Activation/Pulse/Neurovascular Stretch. A generic TAPN framework may be adapted to train and/or assist practitioners in implementing particular treatment modalities for ischemic injury treatment for a any specific Segment or Structure of the body.

It will be appreciated that applications of the TAPN framework described herein are not strictly limited to uses on the human body because the presently disclosed instrumentalities may be adapted for treatment of non-human animals as well.

Again, TAPN stands for Touch, Activation, Pulse and Neurovascular Stretch. There are 2 highlighted phases that focus on ischemic conditioning which are the Activation, or first occlusive event, and Neurovascular Stretch, or second occlusive event. The Touch phase focuses on enhancing the effect of the activation. The Pulse phase lets a practitioner know when the activation is stopping or has stopped and when the neurovascular stretch may begin. As such, the Touch and Pulse phases are preferably but optionally performed because the Activation and Neurovascular stretch phases are more directly responsible for the treatment of RI. The Touch phase enhances the Activation phase by bringing blood flow to the area and better locating the hand placement. The Pulse phase enhances the Activation phase by determining when the Activation is near completion or complete so that the N phase or second occlusive event can occur. Also, these phases do not necessarily need to be performed in a sequential manner. It is possible, for example, to perform the Activation phase simultaneously with the Neuro stretch, or at least with some substantial overlap.

There are two types of ischemic conditioning: local or remote. Depending on the location of the intervention in relation to the target organ, ischemic conditioning may be applied directly on the target Structure or remote to the target Structure as the technique has a systemic effect. For example, remote ischemic conditioning has been demonstrated where brief and transient bouts of occlusion at an artery in the skeletal system, such as the femoral artery, have shown to reduce reperfusion damage in distant organs, such as the heart and brain. Thus, ischemic conditioning can attenuate tissue damage at the site of the applied occlusion and it can also preserve remote tissues throughout the rest of the body. The system may be used as both a local and remote model.

Using the TAPN framework, the modalities facilitated by the system may be stated as a semi-occlusive Pre-C, Per-C and Post-C model that may be applied locally or remotely after a soft tissue musculoskeletal injury takes place or as a form of prevention.

According to one embodiment the system overcomes the aforementioned problems by providing an expert system to apply a manual semi-occlusive vascular technique throughout the body as a method of ischemic conditioning. Clinical experience has shown that the technique is effective at both locally and remotely preventing (Pre-C) musculoskeletal soft tissue injuries and treating them in acute (Per-C), and sub-acute and chronic (Post-C) situations. It is a full body technique, as arteries anywhere in the body can elicit the same healing effect and may benefit from the application of "internal ice" to treat injury. Using a semi-occlusive manual pressure at the nearest proximal vascular site to a Structure or group of Structures and additionally applying an occlusion at the neural structure using a neurovascular stretch in the same structure or group of Structures, can create sufficient ischemia in a region of the body without having to directly obstruct the artery or the nerve itself. This makes an improved alternative to using a blood pressure cuff or clamp.

In one aspect, the system utilizes a framework as an outline for the methodology to apply the technique called TAPN. These phases provide an easy way to train practitioners to remember the sequencing of events to perform the technique.

In one aspect, the system utilizes an anatomical coding system to identify different Structures in the body that need to be treated using semi-occlusion. The system denotes each musculoskeletal Structure in the body with a numerical code which is called the taxonomy number. Each region of the body is defined as a System (a). Each region of the body is then divided into Segments (b). Each Segment of the body is divided into specific soft tissue Structures which can include muscles, ligaments, tendons, organs and bones (c). Thus, each Structure is given the taxonomy code a.b.c. Here is a list of the Systems in the body:

System 1: Lower Extremity
System 2: Upper Extremity
System 3: Spine and Thorax
System 4: Cranium, Face and Anterior Neck
System 5: Pelvic, Abdominal and Visceral By way of example, the Vastus Medialis (a quadriceps muscle) is found in the anterior thigh of the lower extremity. Thus, it is found in System 1, Segment 1 (Femoral) and is listed as the $5^{th}$ Structure of the thigh. The taxonomy code is, accordingly, 1.1.5 which stands for Femoral: Vastus Medialis. Structures are intentionally ordered in a way that they are found right next to each other and have direct fascial connections. Thus, a logical Structure after Vastus Medialis would be the patellar ligament which is denoted by 1.1.6 Femoral: Patellar Ligament. Another example is Pectoralis Major which has a taxonomy code of 2.1.1 Pectoral: Pectoralis Major.

Another element to taxonomy codes as taught herein is the segue Structure. As some Structures connect from one System to the next, segue Structures are identified using the following image:

The S indicates that it is a segue Structure, while the x and y will indicate which System it connects to (see FIG. 8). Not all Structures are segue structures. Only the structures that connect 2 different Systems are labelled as segue Structures.

The T portion of the Touch/Activation/Pulse/Neurovascular Stretch or TAPN framework, indicates the "touch" or palpation of a Structure or group of Structures within a Segment and System of the body that may be treated using the presently disclosed system. In the T portion, a medical practitioner will touch the Structure(s) of interest in a particular Segment of the body as to attract blood flow to it. There is no specific requirement for this phase apart from contacting the tissue(s) of interest with a form of touch in order to create blood flow or erythema to the area of interest.

The A portion of the Touch/Activation/Pulse/Neurovascular Stretch or TAPN framework, indicates the "Activation" or occlusion of the nearest proximal blood vessel that supplies the Structure(s) or Segment of interest. This is termed the first occlusive event and requires specific hand placement on what are known as activation points. The point of this phase is to create the semi-occlusive manual tourniquet around the common proximal arterial supply of the Segment of interest. An activation point, which is the common proximal arterial point that supplies a Segment of the body, is where the first hand is placed called HP1 or Hand Placement 1. This is the hand that is often the proximal hand and is performing the technique using a contact point to create the semi-occlusion manual tourniquet around the common arterial supply of a Segment of the body for 30 seconds to 5 minutes. The method to achieve this requires palpation of the pulse of the common arterial supply of a Segment of the body. Once this is felt, the hand is placed next to the artery (not directly on it) in a perpendicular direction away from the artery as to bisects the artery. This is termed Compression X Glide=Tension at a 90° and has direction which is termed the Vector of Tension at 90°. The Vector of Tension at 90° describes the three-dimensional direction of HP1 at the activation point. It informs the practitioner about how to direct the hand placement in all 3 planes of motion (transverse, frontal and sagittal) to create the manual tourniquet necessary for partial ischemia. The notation for the vector is indicated in each TAPN table using the following notation:

Compression $X$ Glide=<u>Compression</u>(Glide)=Vector of Tension at 90 degrees

This relationship is not intended as a precise mathematical relationship. The relationship merely connotes that the amount of occlusion is provided by compressing at a pressure point and gliding this pressure point out at approximately 90° away from the general direction of elongation in a blood vessel or the axis of the blood vessel proximate the pressure point. Compression or glide may occur in either 1 or 2 planes, but never in 2 planes for compression and glide at the same time. If the glide is directed in 2 planes, then the compression will only be possible in 1 plane. Not all vectors will have all 3 planes involved. The compression plane(s) will always be underlined. The glide plane(s) will always be bracketed. This notation makes it easier for the practitioners to apply the vector more accurately. Additionally, to determine the amount of force used during the compression and glide or tension at 90° along the vector, a subjective scale can be used to help practitioners evaluate the strength of the force being applied as different activation points as certain points will call for different levels of strength to create the manual tourniquet. Level 1 indicates a light force, level 2 indicates a mild force, level 3 indicates a moderate force and level 4 indicates a firm force.

There is also a second hand placement called HP2 or Hand Placement 2. This is often the distal hand which palpates a pulse at an artery distal to the Structure(s) or Segment being treated and acts as a comparison to HP1. However, HP2 may also be involved in creating activation, and when this occurs, it is referred to as a double activation. As activation points move further away from the trunk, it becomes increasingly difficult to develop enough manual pressure to fight systemic pressure. It also becomes difficult to provide a true occlusive event as there are several anastamoses that reroute blood flow. The use of double activation (pressing on 2 different activation points simultaneously) helps address this problem. Thus, HP1 and HP2 act as 2 different activation/occlusion points during a double activation and require Vectors of Tension @ 90° on both. DA denotes Double Activation.

Certain activation points are terminal branches and do not have distal pulses to assess with HP2 nor do they have the potential for double activations. This is because the artery does not have a distal arterial point that is palpable. These are clearly labeled for each Structure and Segment and, thus, no HP2 is available. T denotes Terminal Branch.

The P portion of the Touch/Activation/Pulse/Neurovascular Stretch or TAPN framework, known as the "Pulse" phase, indicates the effectiveness of the activation/first occlusive event and may be felt as a shift in volume and/or rate of a "pulse" at HP1 or HP1 and HP2 (in the case of a double activation). This phase resembles that of the sounds heard in a stethoscope during blood pressure cuff readings. Once the manual tourniquet is applied in the direction of the vector at a point adjacent to the common arterial supply of the Segment of interest, pulses may be felt under the contact points that are creating the Compression X Glide=90°. This is due to the contractile properties of the arteries. As the static pressure competes with systolic blood pressure, the artery will accommodate it's diameter and enlarge which allows blood to move past the manual tourniquet. The turbulence of fluid felt immediately distal to the contact point, is termed the distal turbulent pulses. This is what makes the technique semi-occlusive as it allows the artery to modify its diameter.

The N portion of the Touch/Activation/Pulse/Neurovascular Stretch or TAPN framework, indicates the "Neurovascular" occlusion which involves occluding the vascular supply to the nerve by using stretch. Nerves, which are richly supplied with blood, require a great deal of blood to function normally. Intra-neural blood vessels are shaped like curls so that they can stay relaxed even while a degree of elongation takes place. When a nerve is stretched, the vessels straighten out until their slack is taken up, still permitting ongoing circulation. The protective feature of these curly-cues has its limits as strangulation can occur if a nerve is stretched beyond a certain point. At 8%, blood vessels that supply the nerve begin to get taken up. At 15% of nerve elongation, arterial, capillary and venous flow is completely occluded. Normal flow will resume once the load is removed and as long as the stretch remains under 15%.

There are 2 ways in which the neural stretch is achieved. A local neurovascular stretch is first achieved by stretching the local nerve that supplies the Segment of the body that is being treated. If 15% of the slack of nerve has not been taken up by the local stretch, then a central or dural stretch may be used. The central neurovascular stretch is achieved by enhancing dural tension in the opposite direction to the local nerve stretch, using opposing limbs, including the head, to achieve the effect.

Thus, the second occlusive event that occurs after the activation during the N of the framework, is the neurovascular stretch up to 15% for up to 30 seconds. Adding a neurovascular stretch, either locally or locally and centrally, during the N portion of the framework, augments the effect of the ischemia created in the activation phase and, thus, improves the level of occlusion of the entire technique without compromising the nerve itself.

There are variations of the Touch/Activation/Pulse/Neurovascular Stretch or TAPN framework as to accommodate for the patient symptoms, tolerance and health risks. There are 4 main ways the technique may be varied. For instance, the A portion and the N portion, which are the hallmark phases of the technique as they specifically provide the ischemic conditioning, may be done simultaneously which has been termed "Combined Approach" or it may be done sequentially which has been termed "Separated Approach". The combined approach has an increased ischemic effect as compared to the separated approach. When Touch/Activation/Pulse/Neurovascular Stretch is being done in a phase by phase fashion, the soft tissue "Touch" or palpation is being conducted, the "Activation" at HP1 or HP1 and HP2 are achieved with a corresponding "Pulse", and the "Neurovascular Stretch" is applied independently from one another sequentially making it less effective as an ischemic technique. When the activation point and neurovascular stretch are being conducted simultaneously, this is called a combined approach. Not all patients can tolerate the combined approach, thus, it is important to be able to adjust to the needs of the patient. Another way the technique is varied is based on what component of the TAPN framework is being performed. For instance, individual phases or combinations of the TAPN framework are possible given the patients' needs. If a patient cannot tolerate certain aspects to the framework, the practitioner can simply provide the Touch/Activation/Pulse or TAP phases in s, or the Activation/Pulse or AP phases or the Activation/Pulse/Neurovascular Stretch or the APN phases as their method of choice. Thirdly, the neurovascular stretch also maintains some flexibility as a local stretch may be performed with or without the central stretch. Typically, the local stretch may be accomplished by both the help of the practitioner and patient. However, the central stretch usually requires the active movement of the patient, and thus, may not be suitable for patients that cannot move actively on their own or cannot perform what is necessary for the central stretch. Finally, there is variability in the amplitude of the tension at 90° as patients may have different levels of sensitivity at activation points, and the practitioner can vary the amount of pressure applied to meet the patients' needs.

The framework is particularly useful as an aid in training others to treat patients by use of the system. Medical practitioners can learn to use the framework, including the taxonomy of the soft tissue structures, according to the system in online or live seminars and tutorials where actual or simulated patients are treated using the technique. These and other features of the present system will become apparent to those skilled in manual techniques to help facilitate tissue healing.

The system facilitates a full body technique that may be used in the prevention and treatment of patients afflicted by musculoskeletal soft tissue injuries from reperfusion injury. According to an expert treatment framework called the Touch/Activation/Pulse/Neurovascular Stretch Framework, which bases its effect based on the science of ischemic conditioning, injury to a Structure or Segment in any of the five Systems of the body may be treated using the following phases of the framework:

a) TOUCH: A touch or palpation of a Structure(s) in a Segment of the body that the patient complains of pain, swelling, numbness, aching, tingling, burning, weakness, atrophy, hypersensitivity, circulatory changes and restricted motion or any combinations thereof in order to locate hand position and bring blood flow to the area, is defined as the Touch portion of the framework.

b) ACTIVATION: A perpendicular manual tension is applied to a common vascular site of a Segment of the body that bisects the common artery along a vector. Using the equation Compression X Glide= Compression(Glide)=Vector of Tension at 90°, the manual pressure is provided by Hand Placement 1 or HP1 for 30 seconds-5 minutes at an adjacent area to the nearest proximal artery that supplies the Structure or Segment being treated to semi-occlude it; defined as the Activation (1$^{st}$ Occlusive Event) portion of the framework. A light pulse palpation called Hand Placement 2 or HP2 is placed at the nearest distal artery to the Structure or Segment being treated as a way to evaluate and compare changes in blood flow to Hand Placement 1; If a double occlusion is required to increase the effect of the ischemia, HP2 acts similar to HP1 providing a perpendicular manual tension at 90 degrees (using the equation Compression X Glide=Compression(Glide)= Vector of Tension at 90°) to another proximal artery that supplies the Structure or Segment being treated which is defined as a Double Activation if it is needed. HP2 does not exist if the artery being occluded by HP1 is a terminal branch. HP2 also occurs during the Activation portion of the framework.

c) PULSE: A palpable distal turbulent pulse is felt and then adequately diminishes at HP1 or, in the case of a double activation, at HP1 and HP2, is defined as the Pulse portion of the framework.

d) NEUROVASCULAR STRETCH: A local neurovascular stretch is provided for 30 seconds in the Segment being treated and, if necessary, a central neurovascular stretch may be added during the pulse phase or after it has been completed in order to further occlude the blood vessels that surround the nerve that supply the Structure or Segment being treated, is defined as the Neurovascular Stretch or the N portion of the framework.

BRIEF DESCRIPTION OF THE DRAWINGS

FIG. 3 depicts an image of the temporal variants of ischemic conditioning and when it may be applied in relation to the damaging ischemic event;

FIG. 8 depicts an example of a treatment protocol for System 1, femoral Segment, Structure 9 pectineus muscle denoted with the taxonomy 1.1.9 Femoral: Pectineus;

FIG. 13 depicts a modified list of contraindications and precautions for manual therapy as per New York State Education Department;

FIGS. 14A and 14B respectively provide portions of a summary chart for the Touch/Activation/Pulse/Neurovascular Stretch or TAPN framework provided to practitioners for each listed structure;

FIG. 15 depicts an example of a treatment protocol for System 2, Segment 1 pectoral Segment, Structure 1, Pectoralis Major muscle denoted with the taxonomy 2.1.1 Pectoral: Pectoralis Major;

FIG. 20 shows an example of a treatment protocol for System 3, Segment 5 extrinsic lumbar Segment, Structure 1, Latissimus Dorsi Origin denoted with the taxonomy 3.5.1 Extrinsic Lumbar: Latissimus Dorsi Origin;

FIG. 25 shows an example of a treatment protocol for System 4, Segment 1 occipital Segment, Structure 1, Occipitalis denoted with the taxonomy 4.1.1 Occipital: Occipitalis;

FIG. 30 shows an example of a treatment protocol for System 5, Segment 1B sacral ligaments Segment, Structure 1, Sacrotuberous ligament denoted with the taxonomy 5.1.B.1 Sacral Ligaments/Inferior: Sacrotuberous Ligament;

DETAILED DESCRIPTION OF THE PREFERRED EMBODIMENT

Introductory Principles of Ischemic Conditioning

The present RI treatment system, is designed to provide non-surgical prevention (Pre-C), and treatment of acute (Per-C), sub-acute and chronic (Post-C) musculoskeletal injuries that have been damaged by reperfusion injury. This method of ischemic conditioning can eliminate or reduce symptoms of pain, swelling, numbness, aching, tingling, burning, weakness, atrophy, hypersensitivity, circulatory changes and restricted motion or any combinations thereof.

Figure 1:
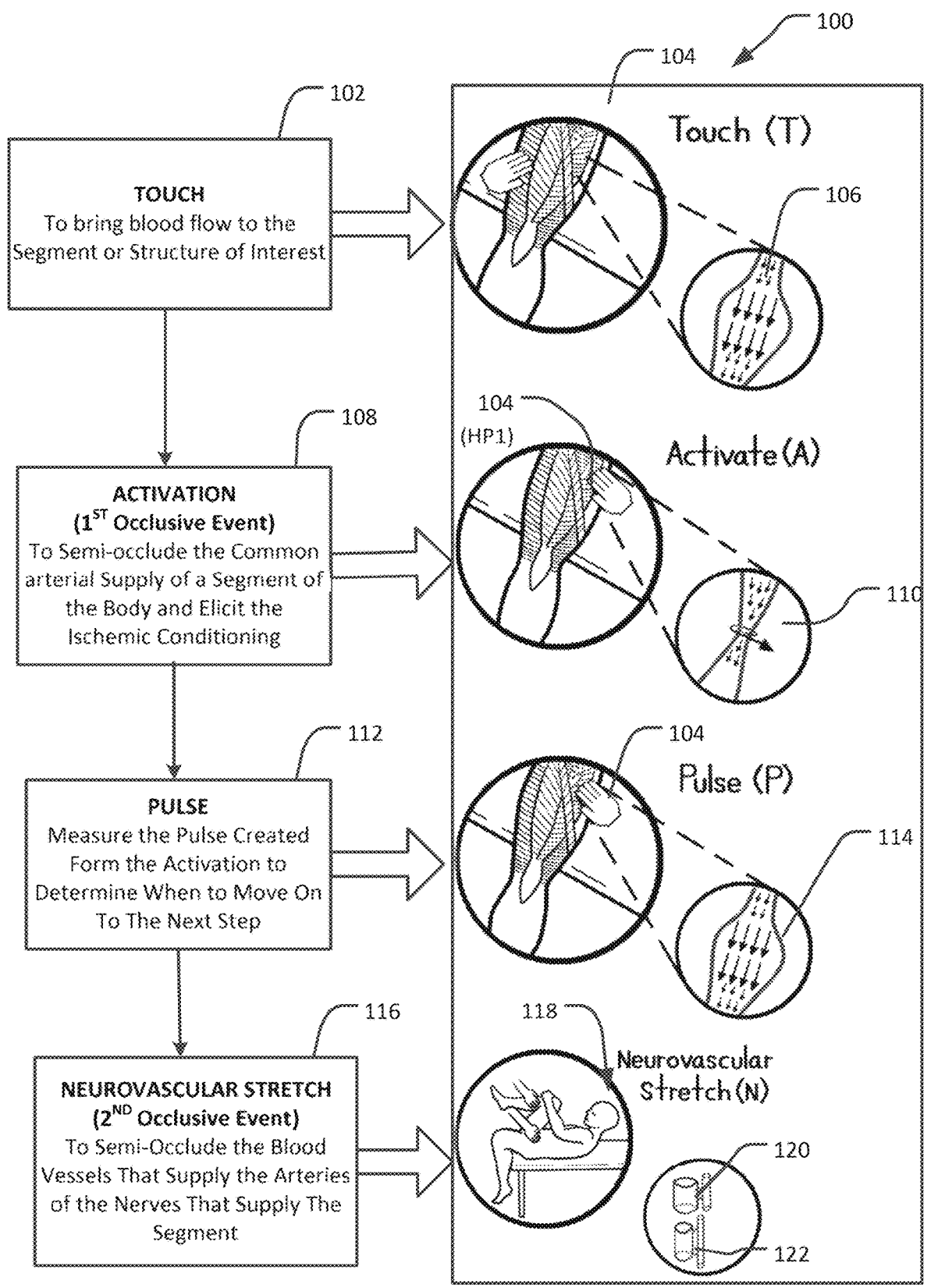
FIG. 1 depicts a simplified scheme of theTouch/Activation/Pulse/Neurovascular Stretch or TAPN framework.

FIG. 1 demonstrates a simplified scheme of the system by displaying the basic phases that occur in performing the Touch/Activation/Pulse/Neurovascular Stretch or TAPN framework. In FIG. 1, there is a flowchart which indicates not only the TAPN phases but also the main objective of the phases, which is to apply ischemic conditioning in musculoskeletal injury. As indicated by the framework, Touch, 101, Activation, 102, Pulse, 103, and Neurovascular Stretch, 104, are conducted to perform this technique. For a more in-depth model see FIGS. 6A, 6B and 14

Figure 4A:
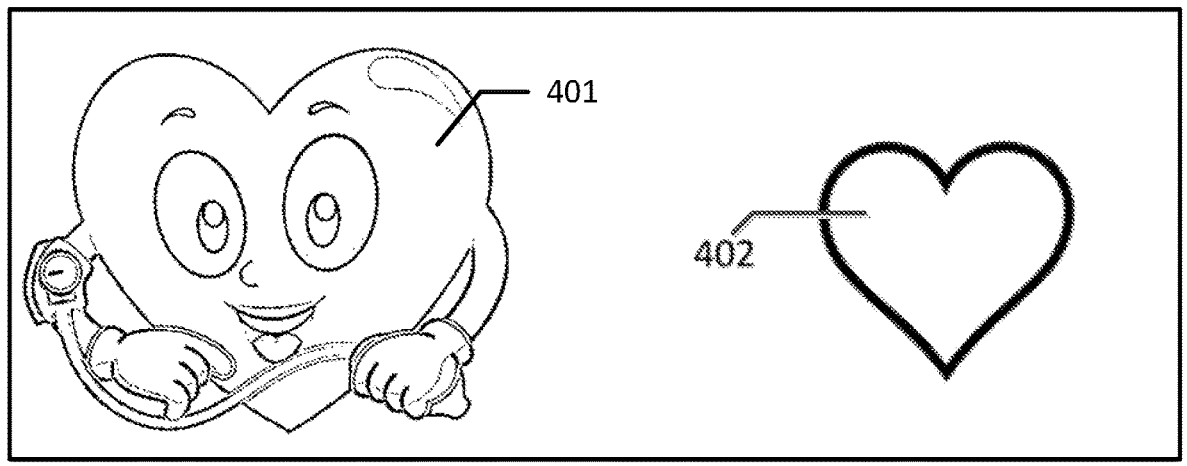
FIG. 4A depicts an image of local ischemic conditioning and FIG. 4B depicts remote ischemic conditioning.
Figure 4B:
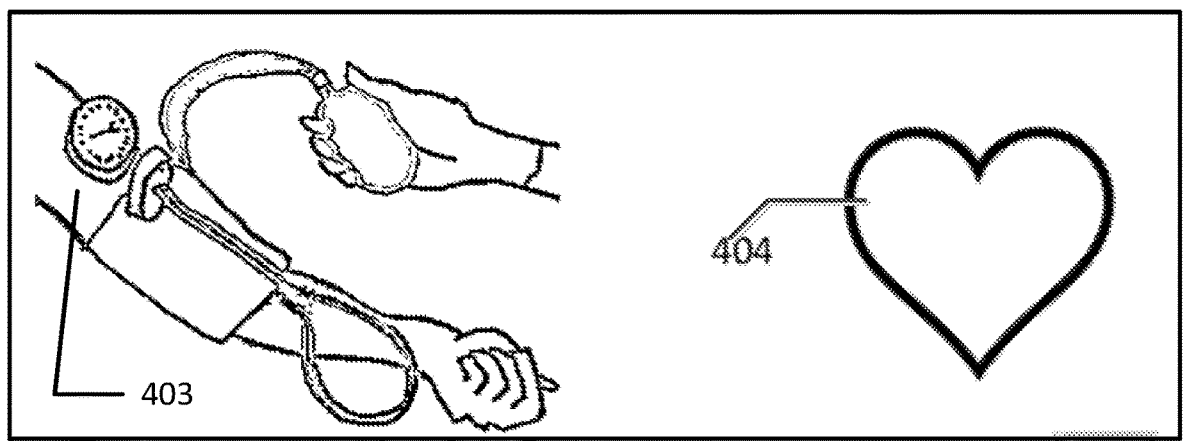

The application of the ischemic conditioning has both local and remote effects because the act of providing an occlusion has both an effect on the structures supplied by the artery being occluded and systemically throughout the body, i.e. remotely. FIGS. 4A and 4B demonstrate the difference between local and remote ischemic conditioning. In FIG. 4A, an example of local ischemic conditioning is where an ischemia as an intervention is applied to an artery in the heart, 401, which can improve the outcomes of tissue damage at the target organ which is also the heart, 402. An example of remote ischemic conditioning is where ischemia as an intervention is applied to an artery at a remote site to the target organ that suffers from the ischemic injury. In this example, the brachial artery is used as the site of the intervention 403, and the target organ is the heart, 404.

Figure 2:
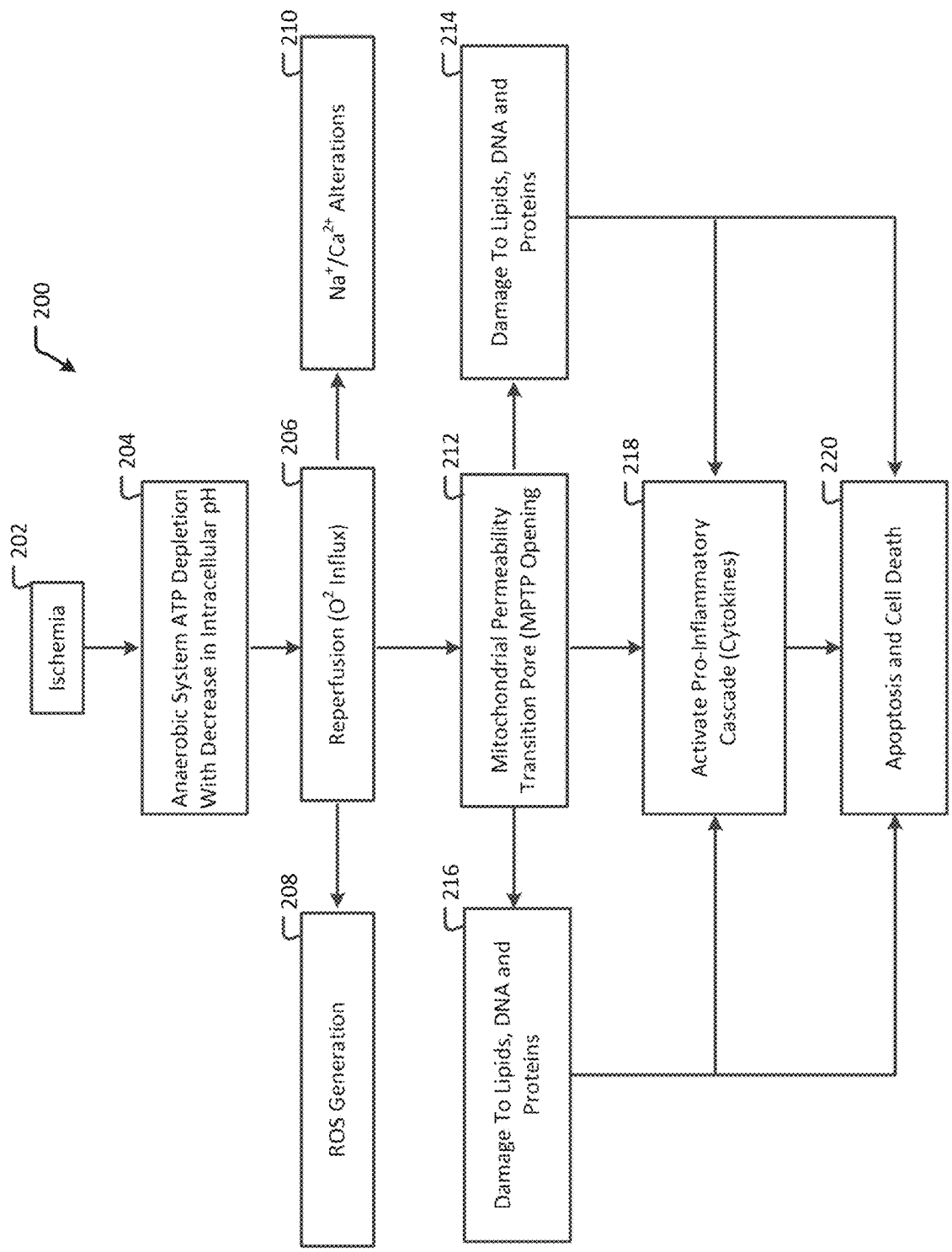
FIG. 2 depicts a flowchart of cellular damage from Reperfusion Injury (RI)
Figure 5:
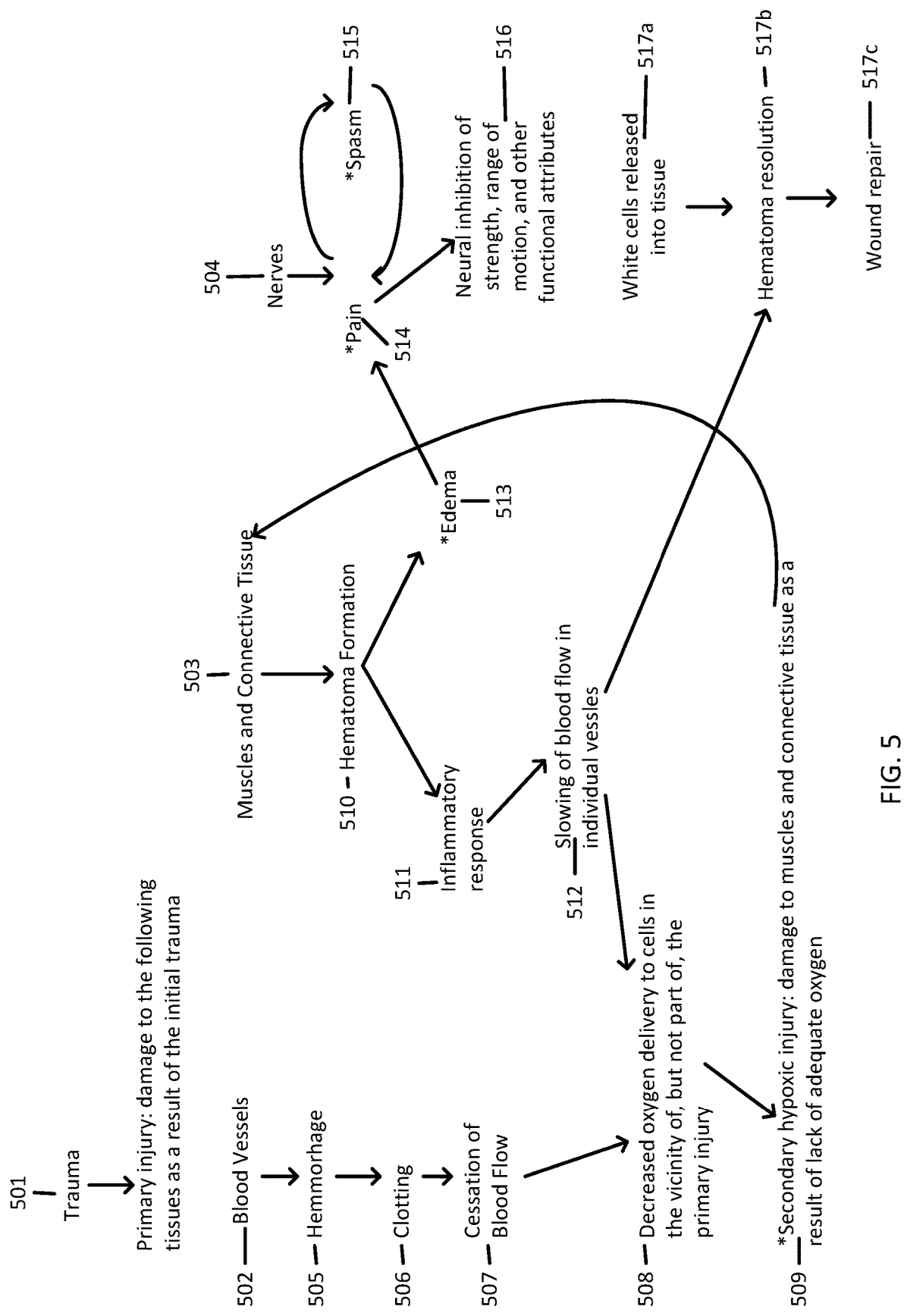
FIG. 5 depicts the Secondary Injury Model in a flowsheet previously presented by Knight et. al.

The present system utilizes the TAPN framework to benefit less severe musculoskeletal soft tissue injury as, ischemia reperfusion cycles or I/R cycles may be found in surrounding healthy tissue which is damaged from primary musculoskeletal trauma through the loss of blood flow, thus mitigating the effects of RI as shown in FIGS. 2 and 5. According to one embodiment, the system facilitates two key principles in action. These principles are: A) the method in which the ischemia is applied to the blood vessels of a Segment of the body and the blood vessels that supply the nerves, and B) the sequencing of the framework which includes the appropriate taxonomy during the "T" portion. The T or Touch phase normally precedes the A or Activation phase and is preferably but optionally performed as a way of improving bhand placement for the A phase while also enhancing blood flow to the targeted area for treatment.

The portions of the TAPN methodology pertaining to the direct ischemic conditioning technique occur during the A or "Activation" and the N or "Neurovascular Stretch" portion of the Touch/Activation/Pulse/Neurovascular Stretch framework. During the A portion, the semi-occlusive manual pressure is applied perpendicular to a blood vessel that is to be occluded. One occlusion technique is to create a pressure point by compressing the blood vessel with tension at 90° and slide the pressure point perpendicularly outward from the blood vessel until a substantial difference in pulse is achieved. This normal-gliding technique produces occlusive tension that may be visualized by the relationship Compression X Glide=Tension at 90°. The A portion may precede the N portion, or there may be temporal overlap such that the A portion precedes the N portion with overlap at the end, or else there may be complete temporal overlap. The N portion may sometimes precede the A portion if patient tolerance improves, however, this is expected to be rarely performed.

Using a pressure point that bisects the common vascular site of a specific Segment or Structure of the body along the indicated vector (3-Dimensional direction) is a preferred aspect of the occlusion technique. The amplitude of the tension can be subjectively determined using the following scale: level 1: light, level 2: mild, level 3: moderate, level 4: firm. The pulse taken at a point distal to the pressure point is termed the distal turbulent pulse. A determination that this pulse has diminished demarcates the end of the "A" phase or portion of the TAPN framework. By way of example, where the A phase precedes the N phase, a diminished pulse in the P phase may guide the practitioner to determine when the "A" phase finishes and when the "N" phase should begin.

Once the distal turbulent pulse has diminished, a second ischemic event "N" occurs at the neurovascular supply to the nerve of the Segment or Structure of interest. This is the neurovascular stretch "N", which is a neural stretch to approximately 15% of the usual anatomical length. This type of stretch is sufficient to choke off the blood supply to the nerve and create another ischemic event. If a 15% stretch cannot be accomplished in the local nerve, central or dural stretches in opposing limbs such as the contralateral limb and the head, may be implemented to enhance the effect of the stretch and, thus, the ischemia.

Both the "A" and the "N" phases of the technique are the ischemic phases and if they are done together, in a combined fashion, then the ischemic effect is augmented. The order of events of the framework is also a unique component of the system and has purpose. As indicated previously, the "T" phase brings blood flow to the Structure(s) of a Segment following guidance outlined by descriptive information that may be reported or otherwise ascertained by reporting from an electronic database. The database may be structured for reporting by taxonomical and/or symptomological identifiers for reporting to a practitioner who follows the report as a guide to implementing a modality of treatment for a specific structure of the body. Once the blood flow is directed to the area of interest during the "T" phase using the taxonomy as a guide, the blood flow is subsequently choked off during the "A" phase. The "P" phase is an indicator of when the "A" ends and the "N" begins. Finally, the "N" enhances the ischemic effect obtained by the "A" as it is the second ischemic event.

The system utilizes a set of expert rules that facilitate a non-surgical semi-occlusive method which may be used to prevent (Pre-C) and treat (Per-C and Post-C) reperfusion injuries in musculoskeletal tissue. FIG. 1, discussed supra., depicts a flowchart of the TAPN framework as may be implemented with use of computer logic.

Figure 6A:
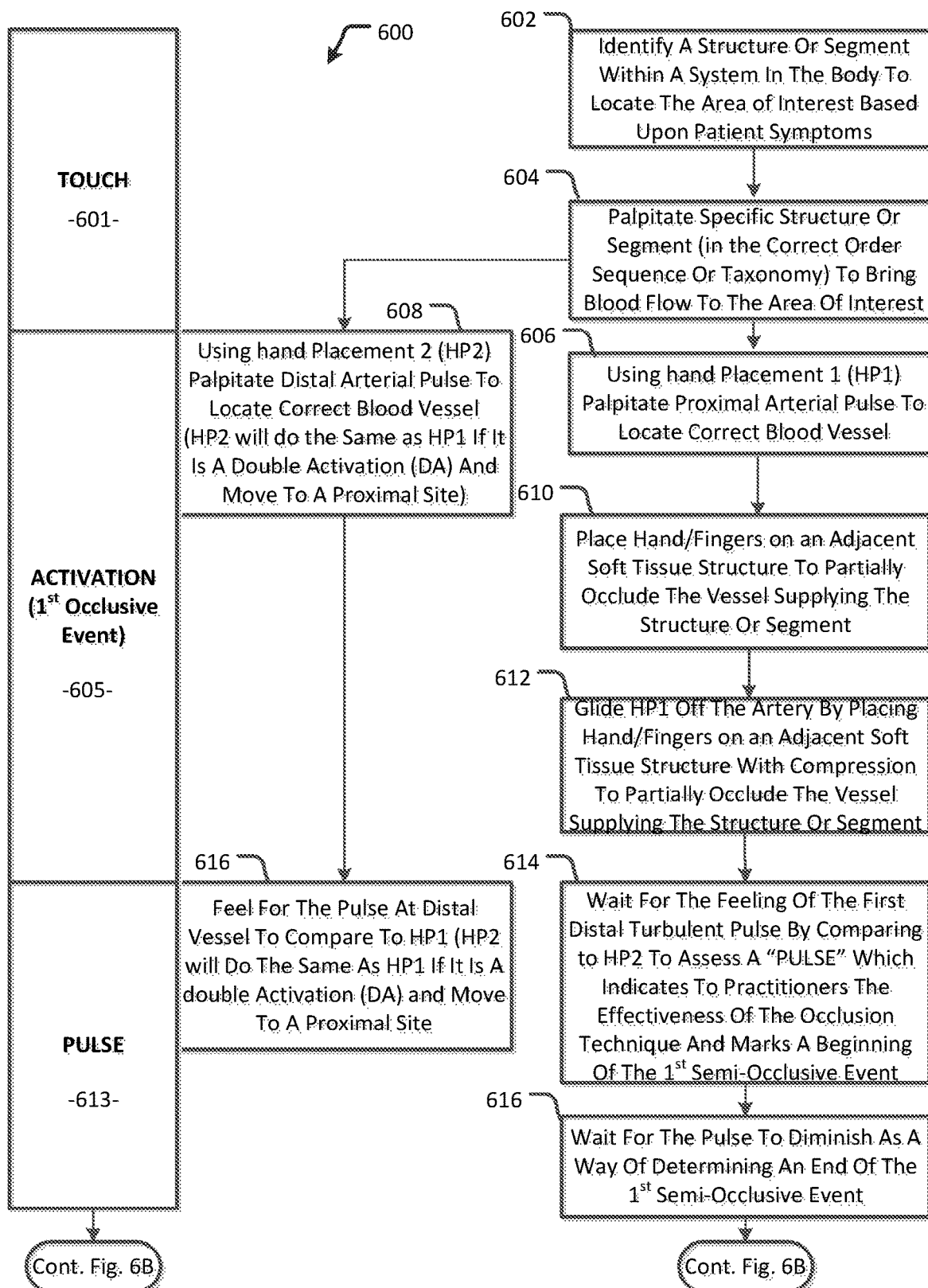
FIGS. 6A and 6B depict a detailed flowchart of the Touch/Activation/Pulse/Neurovascular Stretch or TAPN framework where the flowchart carries over between FIGS. 6A and 6B.
Figure 6B:
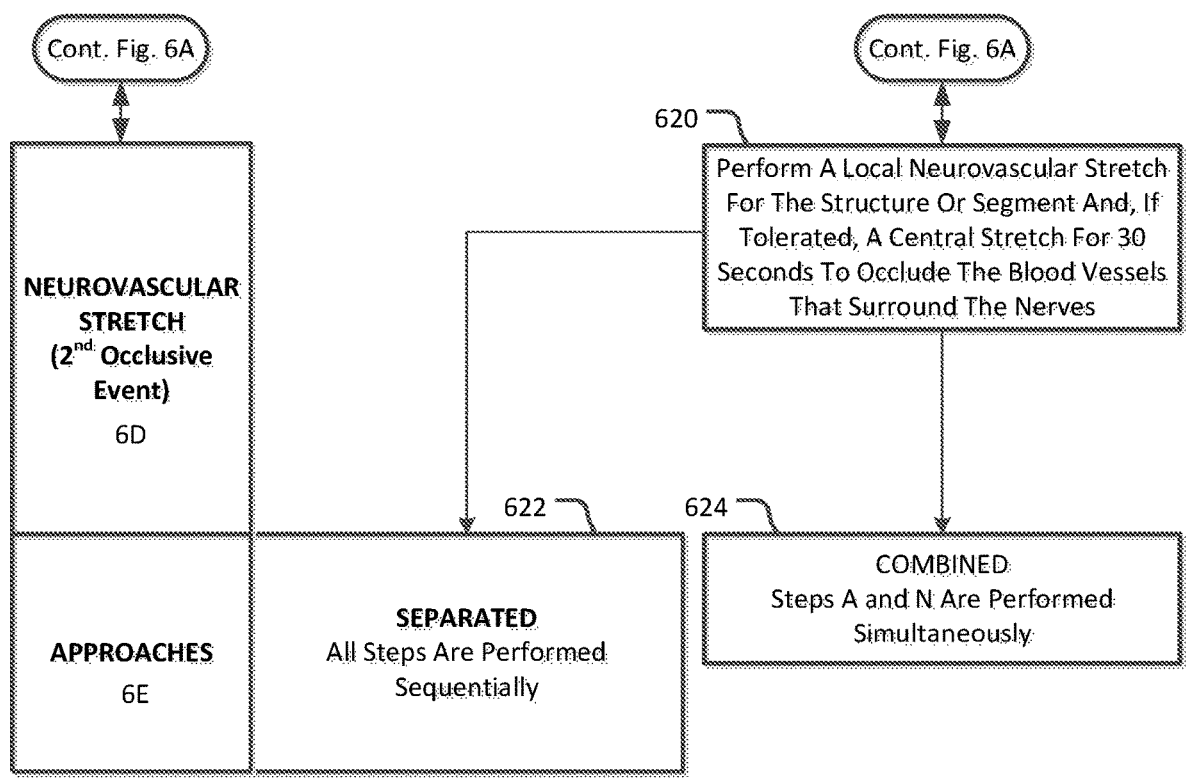

FIGS. 6A and 6B depict a more detailed flowchart 600 of the TAPN framework. The first phase is Touch 601 to identify 602 which Structure or Segment of the body that needs to be treated based on the patient's presented symptoms. After attracting blood flow to the structure(s) that require treatment using palpation 604 or touch in the correct taxonomy as described by the technique, the next goal is to occlude the main arterial supply to the Structure(s) in a particular Segment of the body. This is done by palpation 606 of the proximal common pulse of the artery using the HP1 and simultaneously using HP2 to feel 608 for a pulse distal to the structure(s) in the Segment 608, commencing the activation phase 605. HP1 is first placed 610 on the proximal common artery to begin the first occlusive event and then moved 612 off the proximal common artery along a vector that is approximately perpendicular to the axis of elongation or arterial axis in the artery to begin the Compression X Glide=Tension at 90° along the vector for a suitable time such as 30 seconds to 5 minutes, which acts to create the manual tourniquet in the first partial occlusive event. Once systolic blood pressure matches the Tension at 90° and the artery has vasodilated in response to the stressor, a distal turbulent pulse "P" at 613 is felt 614 at HP1 as blood can move past the tension creating a palpable turbulence. This turbulence may be felt for comparison 616 to HP2 if the second hand is not partaking in a double activation. Alternatively, if HP2 is acting in a double activation, it will follow the same phases as HP1 but at a different proximal arterial site to the structure(s) of interest. When the pulse diminishes 618 this indicates that the next phase or "N" 619 may begin. The neurovascular stretch 620, can occlude the blood supply to nerves and thus may act as a second occlusive event. The stretch at the Segment, called the local stretch, may be maintained for up to 30 seconds, and if tolerated, an opposing dural stretch in the opposite limbs and head, called the central stretch, may be used. The A (605) and the N (619) phases may be performed simultaneously, which is termed a combined approach 624. If the framework is done sequentially, it is termed separated approach 622. 6A-6E, outline the framework's headings.

In context of FIGS. 6A and 6B, it will be appreciated that the phases of Touch 601 and Pulse 613 are preferred but optional phases. The Phases of Activation 605 and Neurovascular stretch 619 may be performed sequentially or with at least some overlap.

Overview of Treatment Process

Figure 7:
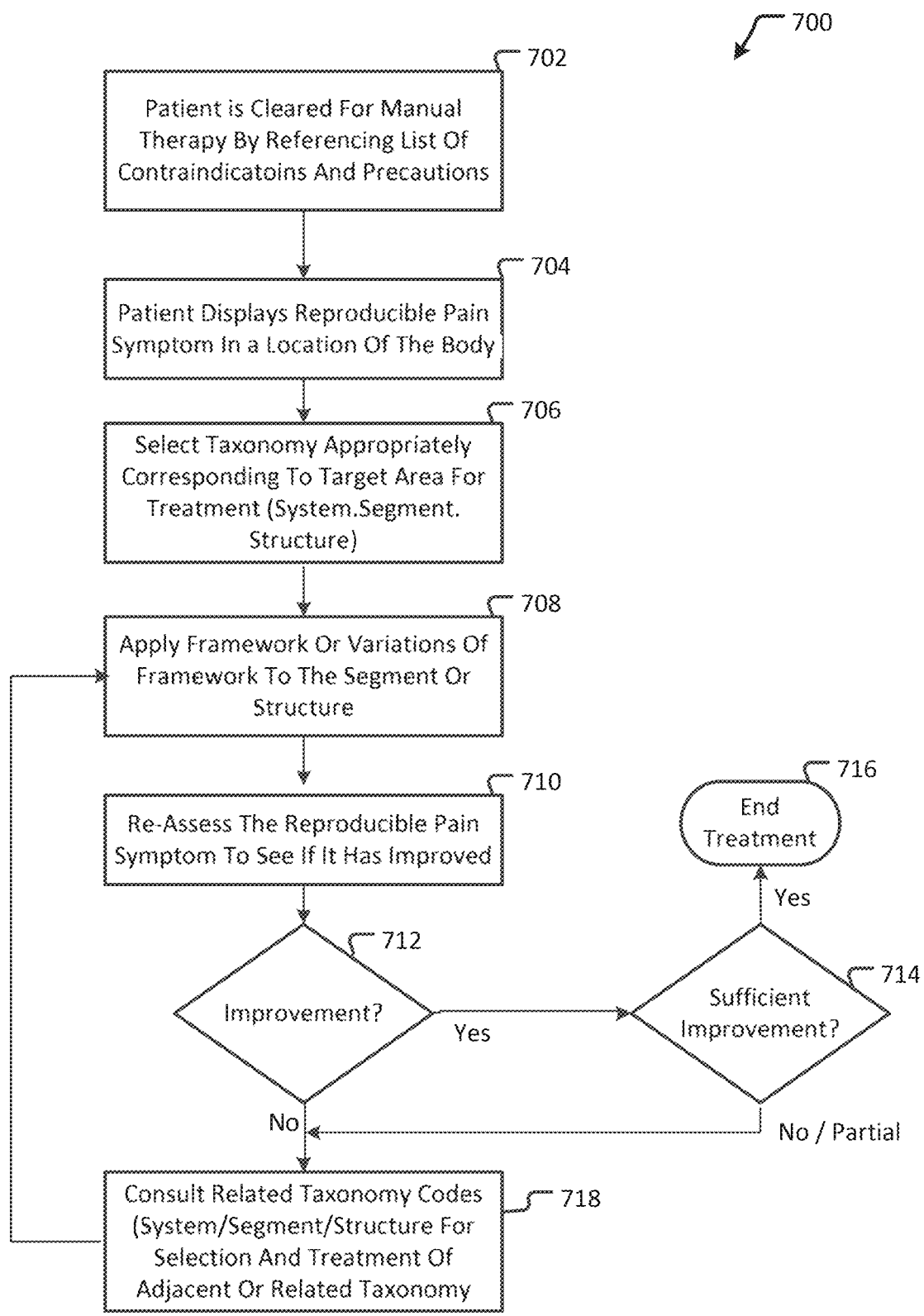
FIG. 7 depicts a flowchart of the Treatment Strategy for a medical practitioner to use in order to treat a particular pain complaint

As the framework may be used clinically, FIG. 7 outlines the general process 700 for use in treating patients according to the presently disclosed instrumentalities. A significant advantage of the framework is that musculoskeletal soft tissue injury may be treated using conservative non-surgical methods. Soft tissues are able to optimize their healing potential through the use of ischemic conditioning. The presently disclosed instrumentalities may be implemented prior to injury as a form of prevention, Pre-C, and in acute, Per-C, and sub-acute and chronic, Post-C, situations. This provides practitioners with tremendous potential to heal tissues with the use of their hands. Once a patient has been given clearance 702 for manual therapy using the guidelines outlined in FIG. 13, a practitioner notes the patient's reproducible pain pattern 704, in any part of the body. Based on the patient's symptoms, the practitioner will select 706 the appropriate location or taxonomy code to begin working on the target area (either a structure, group or structures or an entire Segment). The TAPN framework or any variation is provided 708, which follows the sequencing presented in FIGS. 1 and 6. The patient is asked 710 to see if their symptoms has improved 706. If improvement exists and is sufficient 714 then the treatment can end 716. If there is partial improvement or no improvement 718 improvement, an adjacent Structure, or Segment or System (through the indicated segue structures) may be selected 718 using the taxonomy codes and the framework can repeat from step 708 until sufficient improvement is achieved.

Working Example 1—Groin Pull

FIG. 8 shows a TAPN framework box that may be provided by reporting from a computer database for use in guiding practitioners. The taxonomy code 801 of "1.1.9" identifies System 1 which is the lower extremity, Segment 1 which is a femoral Segment, and a Structure 9 which is pectineus muscle. This taxonomy is also related as a segue structure 802 indicating that there is fascial connectivity to System 5 which is the Pelvic, Abdominal and Visceral System. The Touch row 804 provides useful information concerning the origins, insertions, blood supply and innervation for use as a reference tool in order to guide palpation of the correct structure and review anatomy according to Phase 601 (see FIG. 6A). The Activation row 806 corresponding to Phase 605 of FIG. 6A identifies HP1 808 for the pectineus which is the femoral artery. Note that the star 808 pictorially denotes a hand placement position HP1 for Activation. Row 806 describes the vector as occurring to the posterior indicating a direction of tension for HP1 to create occlusion according to the concept of Compression X Glide=Tension at 90°. Here HP2 810 is simply a pulse point measurement used as a comparison to the pulse at HP1 for assessing the effectiveness of the occlusion at HP1. A heart 810 pictorially denotes use of HP2 to obtain a Pulse.

The Pulse row 814 corresponds to Phase 613 of FIG. 6A and identifies the distal turbulent Pulse that will be felt at the activation point or HP1 808. This is not a double activation because HP1 808 serves as an activation point while HP2 810 merely provides a pulse comparison, which is why Row 812 only indicates a distal turbulent pulse occurring at location of blood flow immediately downstream from HP1 808.

The Neurovascular Stretch row corresponds to Phase 619 of FIG. 6B and lists two additional movement sequences for the local neurovascular stretch supplying the femoral Segment, in this case, there is a local stretch addressing the femoral nerve, which may be supplemented by the dural or central Neurovascular Stretch addressing in this case the head and contralateral lower extremity.

Figure 9:
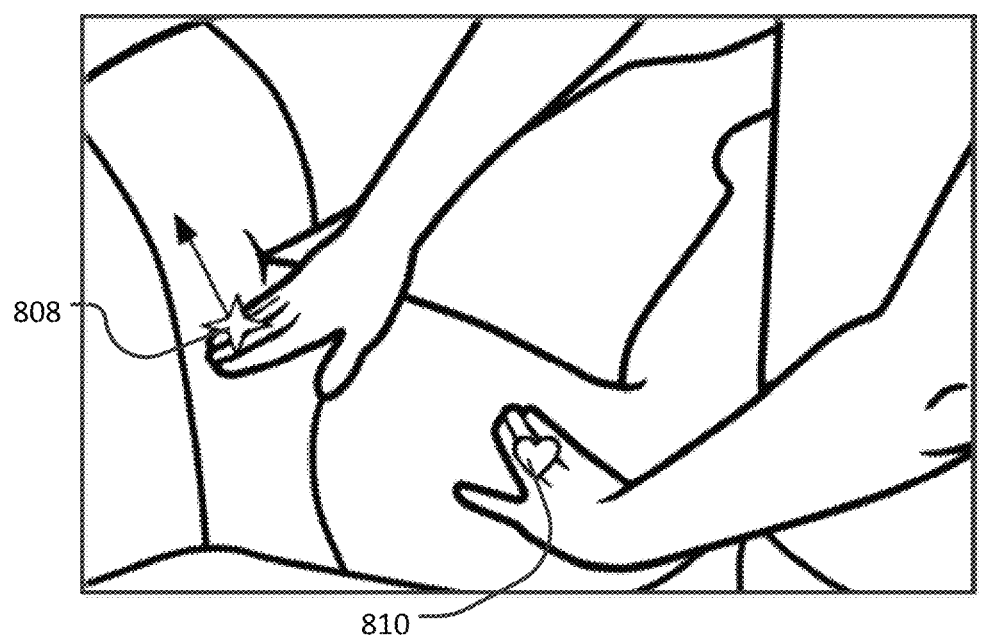
FIG. 9 shows the correct Hand Placement 1 (HP1) and Hand Placement 2 (HP2) for System 1, Segment 1, for use in the Activation component of Touch/Activation/Pulse/Neurovascular Stretch or TAPN framework.

In implementation, as shown in FIG. 9, a patient presents with a groin pull and states pain in the location of the anterior thigh. A practitioner may then choose to treat the pectineus muscle and provide ischemia to the pectineus muscle using the framework box shown in FIG. 8 as a guide. After locating the structure using the anatomy reference in the Touch row 804 and palpating it to elicit blood flow to the area, HP1 808 may be placed at Scarpa's Triangle for 30 seconds to 5 minutes while HP2 810 may be placed at the adductor hiatus to compare the distal turbulent pulse occurring at HP1 808. This is occurring in the Activation component of the framework according to row 806 of FIG. 8. Once the pulse at HP1 808 has adequately diminished, the practitioner can move on to the next phase.

Figure 10:
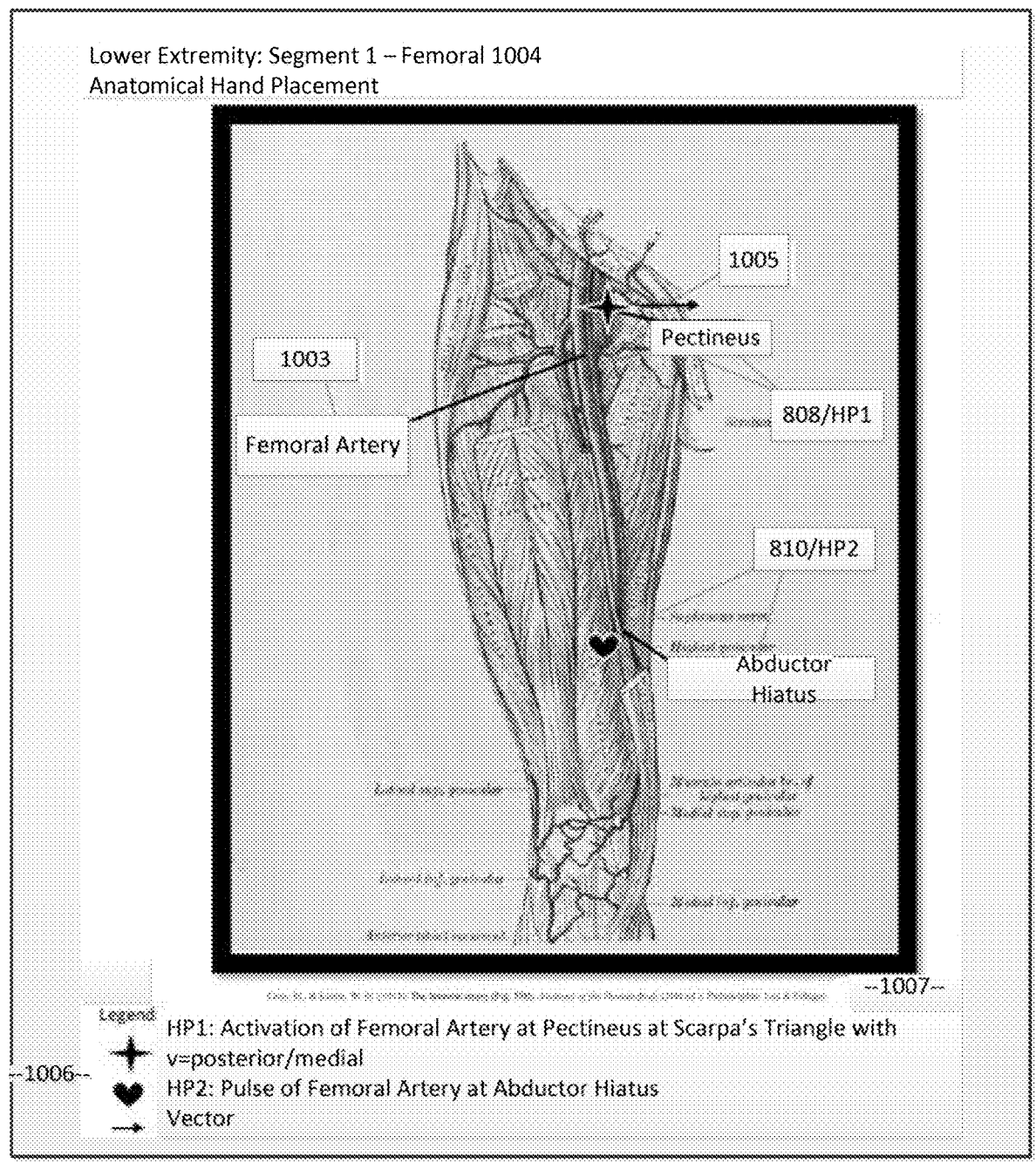
FIG. 10 shows the anatomical hand placement of Hand Placement 1 (HP1) and Hand Placement 2 (HP2) for System 1, Segment 1 on a medical illustration from Gray's Anatomy (reproduced by permission) with the corresponding vector as indicated by an arrow.

FIG. 10 indicates the anatomical hand placements for what is depicted in FIG. 9. Using medical illustration, the activation point HP1 808 is located at the pectineus in Scarpa's triangle using the star as a notation, as previously mentioned. The pulse point at HP2 810 at the adductor hiatus is indicated a heart as a notation, as previously mentioned. The main arterial supply for the anterior thigh that is here called the Femoral Segment 1004 is indicated as the femoral artery 1003, and the vector 1005 or 3-Dimensional tension of HP1 808 is indicated as the vector 1005, using the notation of underlining the compression and bracketing the glide to enhance occlusion according to the concept: Compression X Glide=compression(Glide)=Vector of Tension at 90°.

A legend 1006, accompanies the medical illustration which has been cited for use, 1007.

Figure 11:
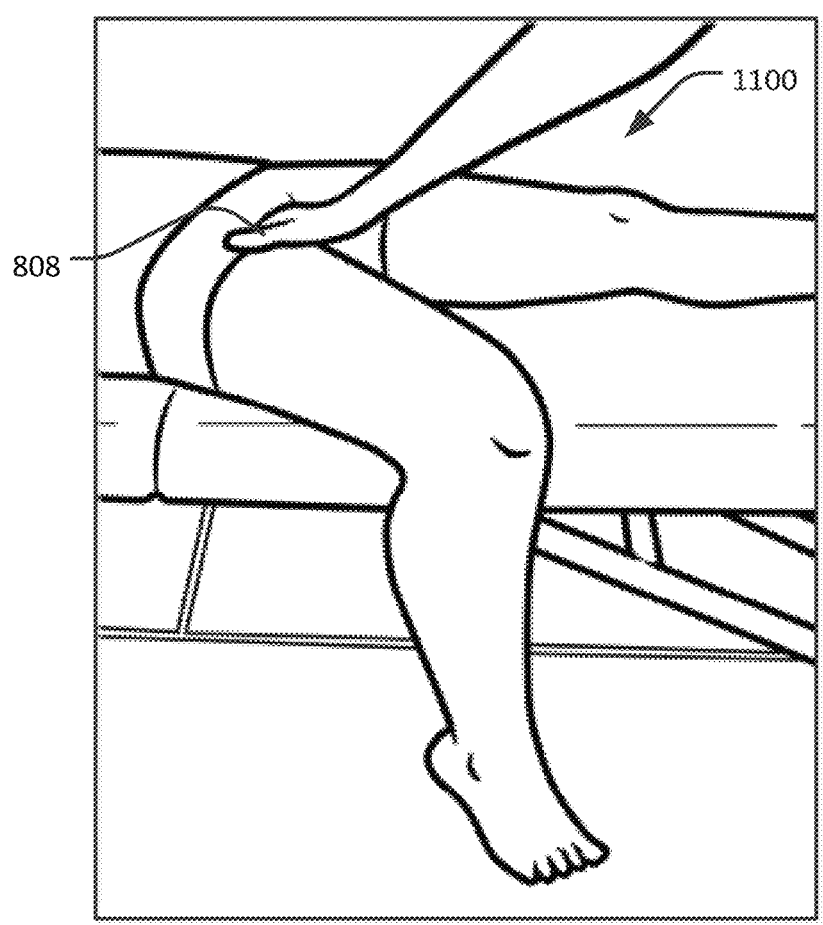
FIG. 11 shows a local neurovascular stretch called the Local Stretch in the Neurovascular Stretch component of Touch/Activation/Pulse/Neurovascular Stretch or TAPN framework according to one modality of treatment.
Figure 12:
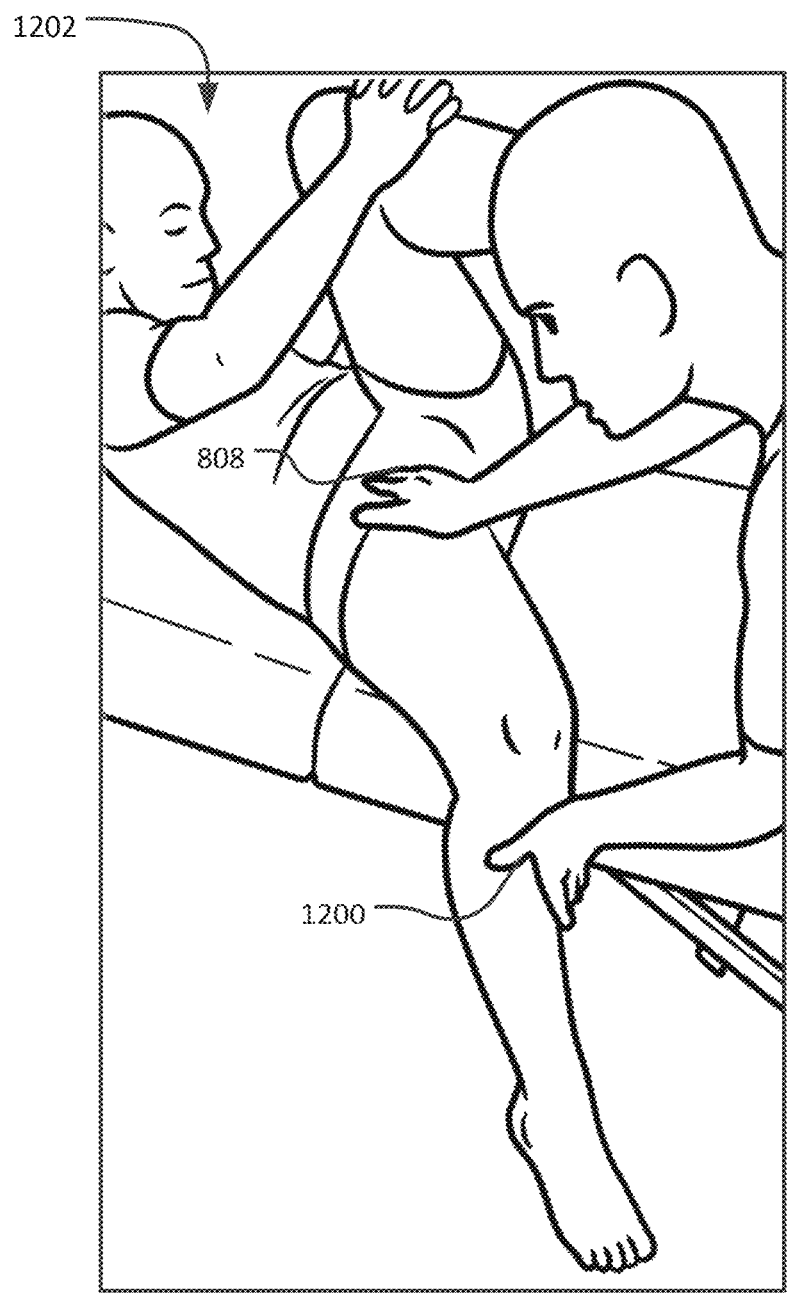
FIG. 12 shows a central neurovascular stretch called the Central Stretch in the Neurovascular Stretch component of Touch/Activation/Pulse/Neurovascular Stretch or TAPN framework according to one modality of treatment.

FIG. 11 demonstrates use of a combined approach for the local stretch at the femoral nerve. This means that HP1 808 is being maintained simultaneously at the pectineus using the correct vector 1005 as described above, while the local femoral nerve stretch 1100 including a supine hip extension with internal rotation plus knee flexion and ankle plantarflexion is being by the patient and/or the practitioner. If more nerve stretch is needed to reach the approximate 15% required to occlude blood vessels surrounding the nerve, and the patient can tolerate the movement, then a central stretch 1200 may be done as demonstrated in FIG. 12. This also demonstrates the combined approach where HP1 808 is being maintained at the same time as the local stretch 1200, with the assistance of the practitioner. Additionally, the patient has assisted with flexing 1202 the contralateral limb and head, in order to provide the central stretch which enhances the occlusive effect upon the femoral nerve. The central stretch 1200 may be left out, or the neurovascular stretch as a whole may be left out if a patient cannot tolerate the movements according to the variations. A separated approach may also be used as a variation if the combined approach cannot be tolerated.

FIGS. 14A and 14B show the phases of the TAPN framework represented in a generic box format with data fields that may be adapted for use in electronic or paper reporting to demonstrate RI treatment of any Structure in the human body. The system of expert rules may provide a box like FIGS. 14A and 14B as a guide facilitating the TAPN framework according to any hierarchical taxonomy code, such as System/Segment/Structure as shown in FIG. 8. To illustrate a suitable reporting structure by way of example, TAPN box 1400 includes an identifier as taxonomy code 1402, which in this case allocates the human body into discrete parts where hand placements may control blood flow for occlusive treatment of RI. All structures and tissues of the body may be outlined in this way as a standard format to ease the complication of the practitioner being trained and/or guided in implementing the technique. Field 1403 identifies one or more a segue Systems X, Y which are different Systems that are fascially related to particular system of taxonomy code 1402.

A Touch row 1404 provides useful information 1406 concerning the origins, insertions, blood supply and innervation for use as a reference tool in order to guide palpation of the correct structure and review anatomy according to Phase 601 (see FIG. 6A). An Activation row 1408 corresponding to Phase 605 of FIG. 6A includes a field 1410 for hand placement HP1 occurring over the proximal common artery for the Segment, together with a description 1412 of vector movement or tension of this hand position that enhances the occlusive effect according to the concept of Compression X Glide=Tension at 90°. A field 1414 for hand placement HP2 describes placement of a second hand over structures that have been treated by HP1 1410 for either: (1) a second activation point, or (2) to ascertain a distal pulse that by virtue of its relative intensity indicates the effectiveness of HP1 1410. Since HP2 1412 may be, in the alternative, a second activation point or a location to measure a distal pulse, a star 1416 may be used to designate use as a second proximal activation point, and a heart 1418 pictorially designates use to ascertain a distal pulse. A designation "T," as needed, indicates a terminal branch such that HP2 1412 is not required. Where HP2 1412 is intended for use as a double activation point given the designation "DA", there will be a second vector field (not shown) allocated to HP2 1412 describing movement of HP2 to enhance the occlusive effect of the Structure or Segment of interest.

A Pulse row 1420 corresponds to Phase 613 of FIG. 6A includes field 1422 listing distal turbulent Pulse that will be felt at the activation points HP1 1410 and HP2 1412 if it is a double activation.

A Neurovascular Stretch row 1424 corresponds to Phase 619 of FIG. 6B and includes field 1426 listing two movement sequences for the local neurovascular stretch supplying the femoral Segment. The two movement sequences include a local stretch intended to occlude blood supplying the main nerve proximate HP1 and HP2. There is also a central stretch that improves the occlusion if the patient can tolerate the central stretch.

A legend field 1428 accompanies the medical illustration which has been cited for use, 1007.

Working Example 2—Pectoral Strain

FIG. 15 shows a TAPN framework box 1500 that may be provided by reporting from a computer database for use in guiding practitioners. The taxonomy code 1502 of "2.1.1" identifies System 2 which is the upper extremity, Segment 1 which is a pectoral Segment of System 2, and a Structure 9 which is the pectoralis major muscle of Segment 1. This taxonomy is also related as a segue structure 1504 indicating that there is fascial connectivity to System 3 which is the Spine and Thorax System. The Touch row 1506 corresponds to Phase 601 of FIG. 6A and provides useful information concerning the origins, insertions, blood supply and innervation for use as a reference tool in order to guide palpation of the correct structure and review anatomy according to Phase 601 (see FIG. 6A). The Activation row 1508 corresponding to Phase 605 of FIG. 6A associates HP1 1510 with the pectoralis minor, specifically at the $2^{nd}$ section of the axillary artery at the pectoralis minor. The Activation row 1508 describes a vector 1512 associated with HP1 1510 as occurring to the posterior/inferomedial indicating a direction of tension to create occlusion according to the concept of Compression X Glide=Tension at 90°. Here HP2 1514 is simply a pulse point measurement used as a comparison to the pulse at HP1 1510 for assessing the effectiveness of the occlusion at HP1 1510. HP2 1514 is to be taken as the brachial pulse at the antecubital fossa.

The Pulse row 1516 corresponds to Phase 613 of FIG. 6A and identifies the distal turbulent Pulse that will be felt at the activation point or HP1 1510. This is not a double activation because HP1 1510 serves as an activation point while HP2 1514 merely provides a pulse comparison, which is why Row 1514 only indicates a distal turbulent pulse at the patient's pectoral tunnel.

The Neurovascular Stretch row 1516 corresponds to Phase 6D 619 of FIG. 6B and lists two additional movement sequences for the neurovascular stretch supplying the pectoral Segment. In this case, there is a local stretch 1518 addressing the pectoral nerve by use of a shoulder abduction to 120° with an elbow extension, forearm supination and wrist and finger extension. The may be enhanced by the second movement sequence which is the use of a central neurovascular stretch 1518 including contralateral neck side flexion.

Figure 16:
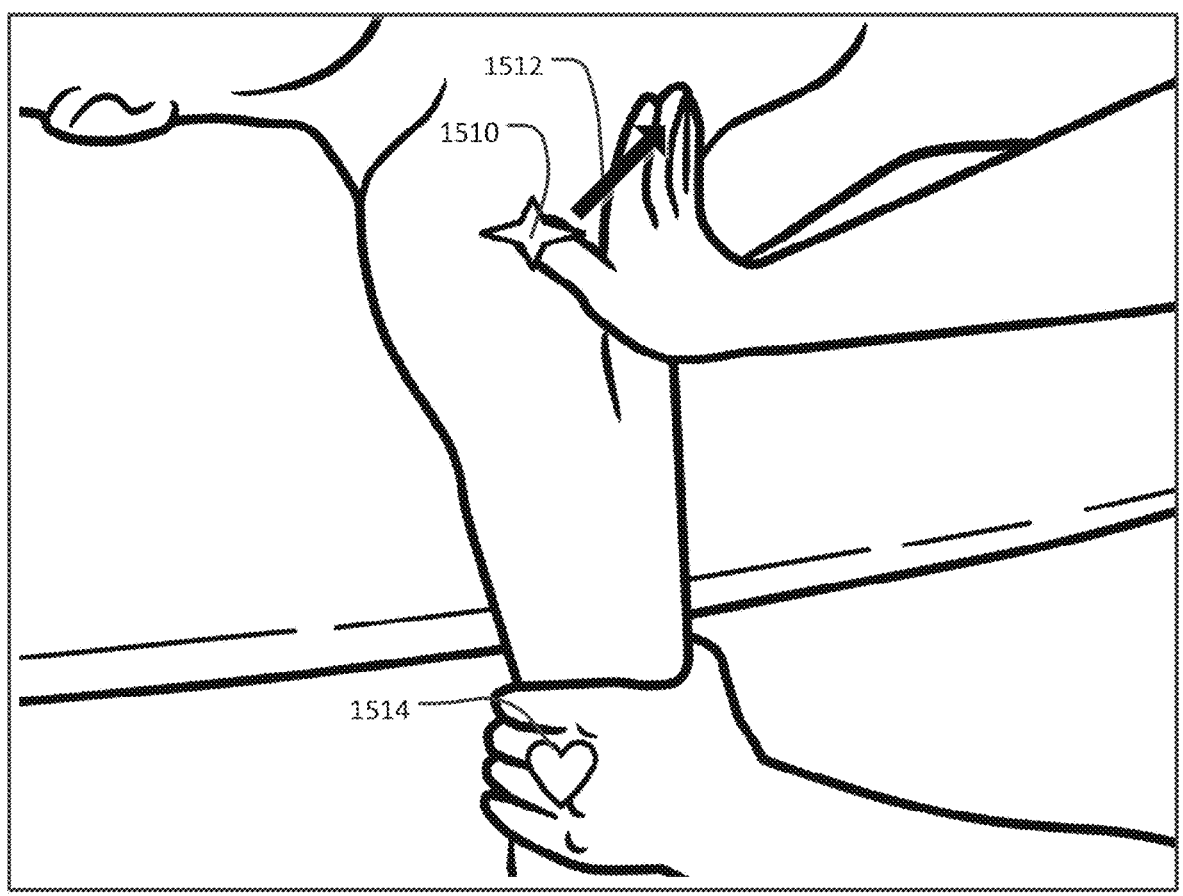
FIG. 16 shows the correct Hand Placement 1 (HP1) and Hand Placement 2 (HP2) for System 2, Segment 1, for use in the Activation component of Touch/Activation/Pulse/Neurovascular Stretch or TAPN framework.

In implementation, as shown in FIG. 16, a patient presenting with a pectoral muscle pull or strain and states pain in the location of the pectoralis major. A practitioner may then provide ischemia at the pectoralis minor using the framework box shown in FIG. 15 as a guide. After locating the structure using the anatomy reference in the Touch row 1506, and palpating it to elicit blood flow to the area, HP1 1510 may be placed at the pectoralis minor for 30 seconds to 5 minutes to occlude the main upstream artery for the pectoral Segment at the $2^{nd}$ portion of the axillary artery while HP2 1514 may be placed at the antecubital fossa to compare against the pulse occurring at HP1 1510. This is occurring in the Activation component 1508 of the framework. Once the pulse at HP1 1510 has adequately diminished, the practitioner can move on to the next phase.

Figure 17:
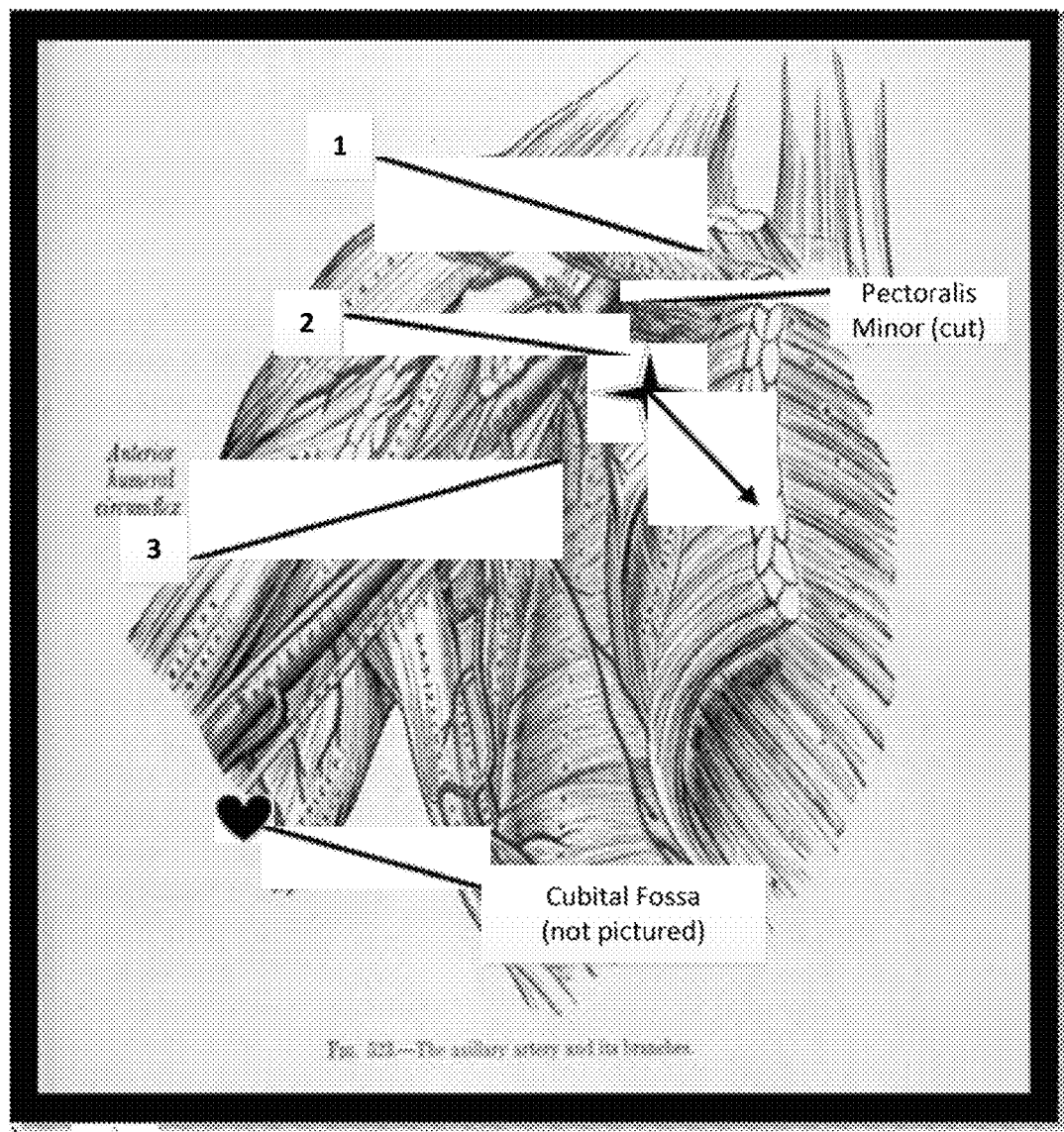
FIG. 17 shows the anatomical hand placement of Hand Placement 1 (HP1) and Hand Placement 2 (HP2) for System 2, Segment 1, on a background medical illustration from Gray's Anatomy (reproduced by permission) with the corresponding vector as indicated by an arrow.

FIG. 17 shows the anatomical hand placements for what is depicted in FIG. 16. Using medical illustration 1700, the activation point of HP1 1510 at the pectoralis minor is designated using the star as a notation as previously mentioned. The pulse point of HP2 1514 at the antecubital fossa is indicated using the heart as a notation as previously mentioned. Gliding HP1 1510 along the vector 1512 occludes the main arterial supply for the pectoral Segment according to the concept of Compression X Glide=Compression(Glide)=Vector of Tension at 9J. A legend 1702 accompanies the medical illustration 1700 to provide additional information concerning the hand placements HP1 1510 and HP2 1512.

Figure 18:
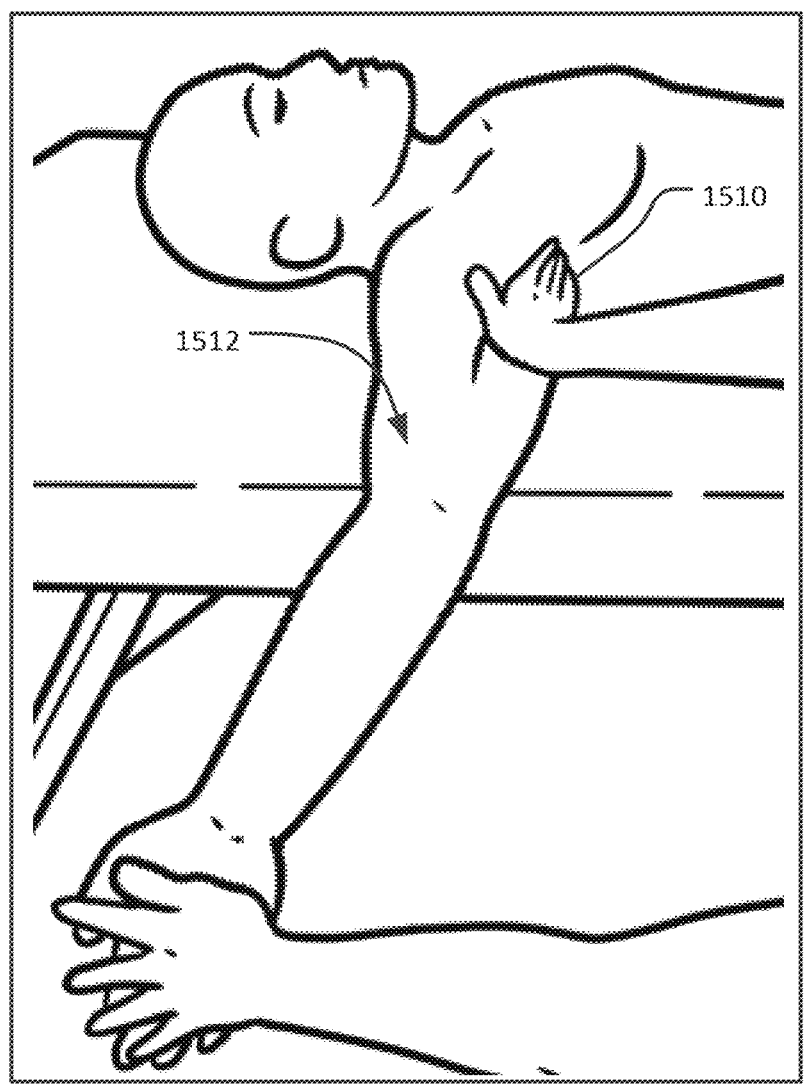
FIG. 18 shows the local neurovascular stretch called the Local Stretch in the Neurovascular portion of Touch/Activation/Pulse/Neurovascular Stretch or TAPN framework for System 2, Segment 1.

FIG. 18 demonstrates use of a combined approach for the local stretch at the pectoralis minor. This means that HP1

Figure 19:
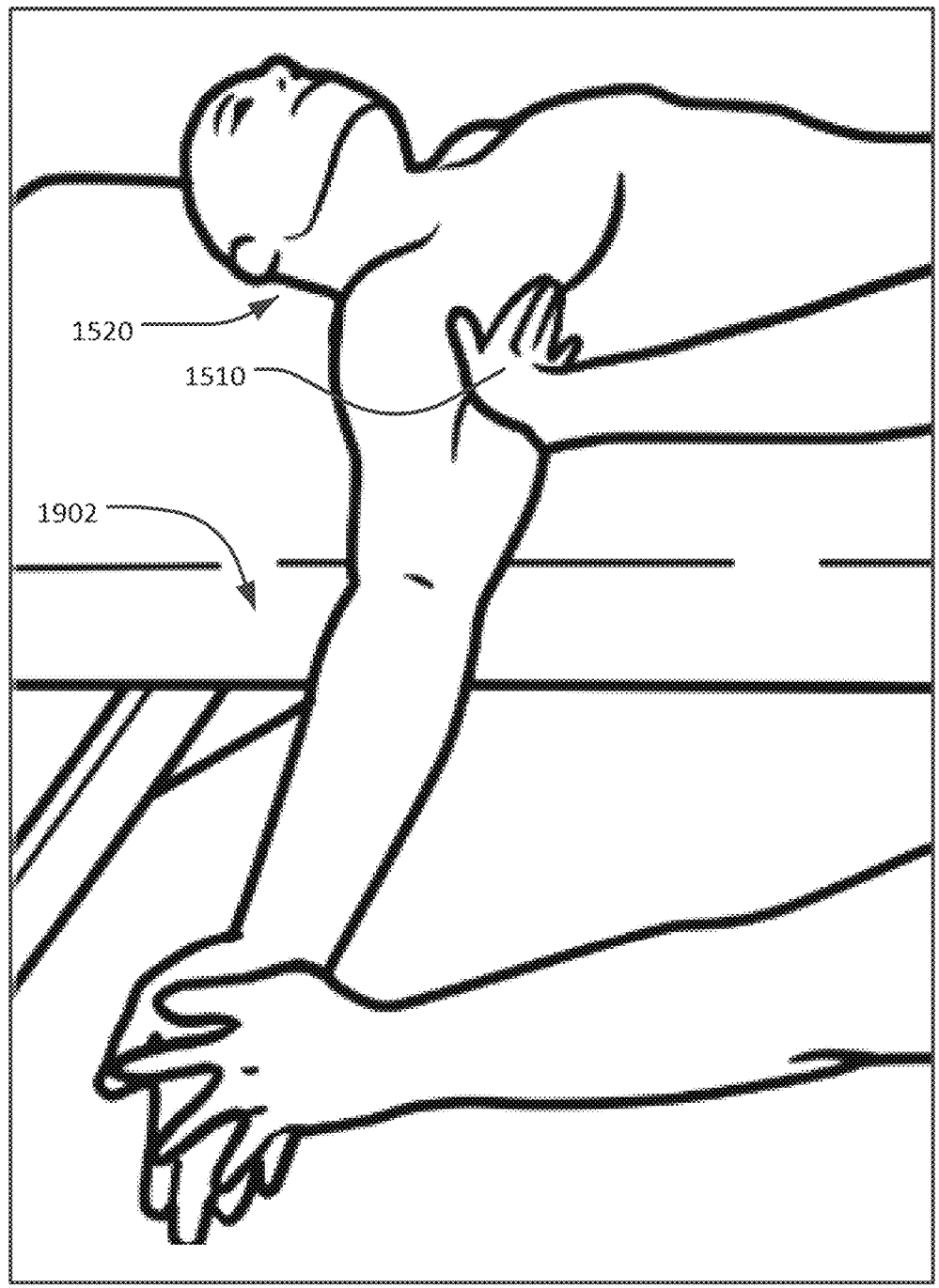
FIG. 19 shows the central neurovascular stretch called the Central Stretch in the Neurovascular portion of Touch/Activation/Pulse/Neurovascular Stretch or TAPN framework for System 2, Segment 1.

1510 is being maintained simultaneously at the pectoralis minor using the correct vector 1512, while a local pectoral nerve stretch 1518 is being produced by the patient and/or the practitioner. If more nerve stretch is needed to reach the approximate 15% required to occlude blood vessels surrounding the nerve, and the patient can tolerate the movement, then a central stretch 1520 may be done as demonstrated in FIG. 19. This also demonstrates the combined approach where HP1 1510 is being maintained at the same time as the local stretch 1518, with the assistance of the practitioner. Additionally, the patient has assisted with flexing the contralateral side of the neck, in order to provide the central stretch which provides the central stretch 1520 to enhance the effect of the local stretch 1518. The central stretch 1520 may be left out, or the neurovascular stretch as a whole may be left out if a patient cannot tolerate the movements according to the variations.

Working Example 3—Lower Back Pain

FIG. 20 shows a TAPN framework box 2000 that may be provided by reporting from a computer database for use in guiding practitioners. The taxonomy code 2002 of "3.5.1" identifies System 3 which is the Spine and Thorax System, Segment 5 which is the Extrinsic Lumbar Segment of that System, and Structure 9 which is the Lattisimus Dorsi Origin of the Extrinsic Lumbar Segment. This taxonomy is also related as a segue structure 2004 indicating that there is fascial connectivity to Systems 1, 2 and 5. The Touch row 2006 provides useful information concerning the origins, insertions, blood supply and innervation for use as a reference tool in order to guide palpation of the correct structure and review anatomy according to Phase 601 (see FIG. 6A). The Activation row 2008 corresponding to Phase 605 of FIG. 6A lists HP1 2010 as being over the thoracodorsal artery with latissimus insertion at the inferior angle of the scapula. A second hand placement position HP2 2012 for Activation; however, this differs from HP2 of FIGS. 8 and 15 because HP2 2012 of FIG. 20 is a second or double activation point providing a second point of occlusion at the lumbar arteries located between the transverse processes of lumbar vertebrae L1 to L5. Movement of HP1 2010 occurs as described for vector 2014 to the anterior/medial to facilitate the occlusive effect of HP1 2010. Similarly, the vector 2016 is associated with HP2 2012 where tension to the anterior/medial enhances the occlusive effect of HP2 2012. These vector movements occur according to the concept of Compression X Glide=Tension at 90°.

The Pulse row 2018 corresponds to Phase 613 of FIG. 6A and identifies the distal turbulent pulses at the thoracodorsal and lumbar arteries that will be felt at the activation points HP1 2010 and HP2 2012. This is a double activation at the thoracodorsal artery and Lumbar Arteries because both HP1 2010 and HP2 2012 serve as activation points.

The Neurovascular Stretch row 2020 corresponds to Phase 619 of FIG. 6B and lists two additional movement sequences for the neurovascular stretch of key nerves in the taxonomy. In this case, there is a local stretch 2022 addressing the thoracodorsal and ventral lumbar rami by use of a hip extension with adduction and internal rotation together with contralateral lumbar rotation. This may be enhanced by a central neurovascular stretch 2024 utilizing in this case an ipsilateral shoulder flexion and internal rotation with elbow pronation and head flexion.

Figure 21:
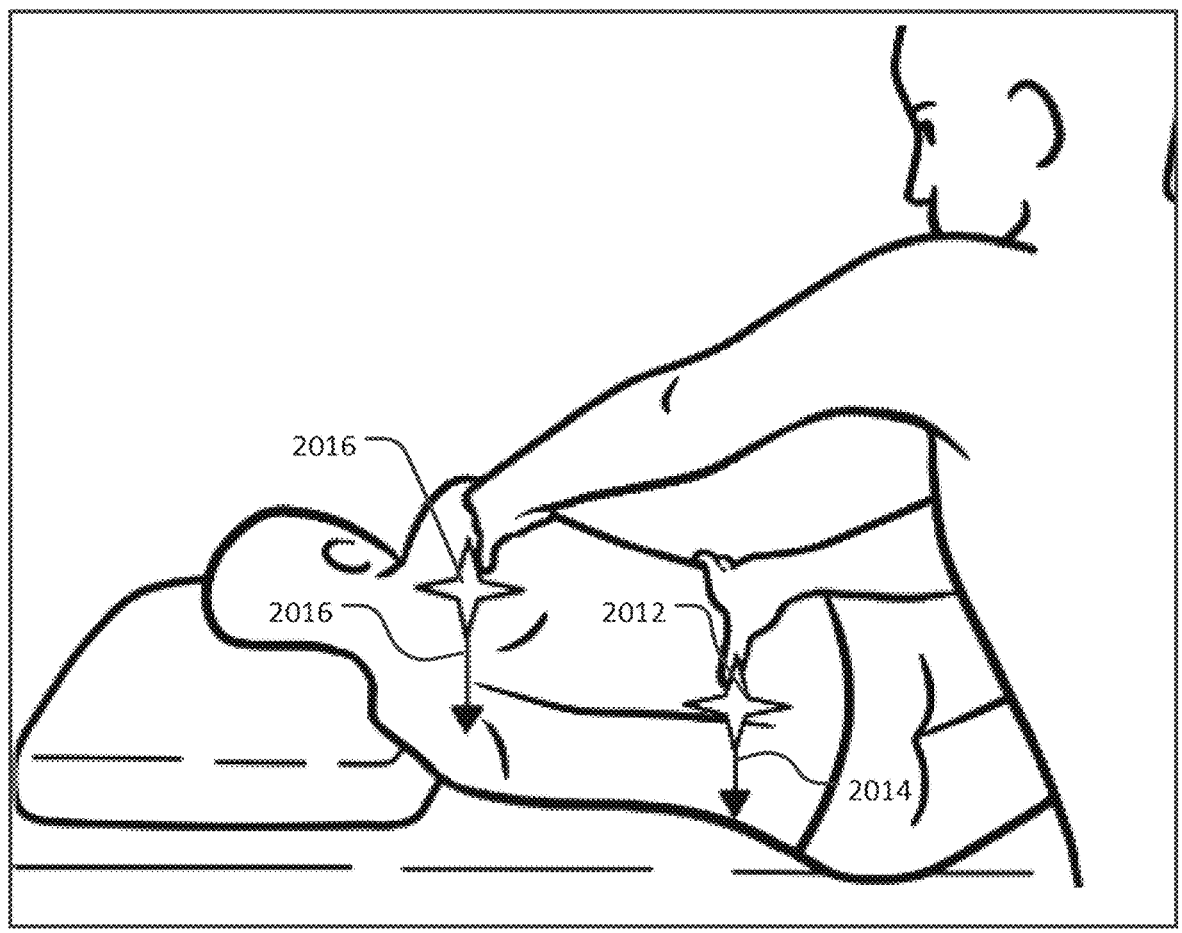
FIG. 21 shows the correct Hand Placement 1 (HP1) and Hand Placement 2 (HP2) for System 3, Segment 5, for use in the Activation component of Touch/Activation/Pulse/Neurovascular Stretch or TAPN framework.

In implementation, as shown in FIG. 21, a patient presents with lower back pain. A practitioner may then provide ischemia to the thoracodorsal artery and the lumbar arteries using the framework box shown in FIG. 20 as the guide. After locating the structure using the anatomy reference in the Touch row 2006 and palpating to elicit blood flow to the area, HP1 2010 may be placed at the thoracodorsal artery for 30 seconds to 5 minutes while HP2 2012 is placed at the lumbar arteries. Gliding along vectors 2014, 2016 occurs as described in row 2008 of FIG. 20 to create the occlusive effect using these hand placements. Once the pulses at HP1 2010 and HP2 2012 have adequately diminished, the practitioner can move on to the next phase.

Figure 22:
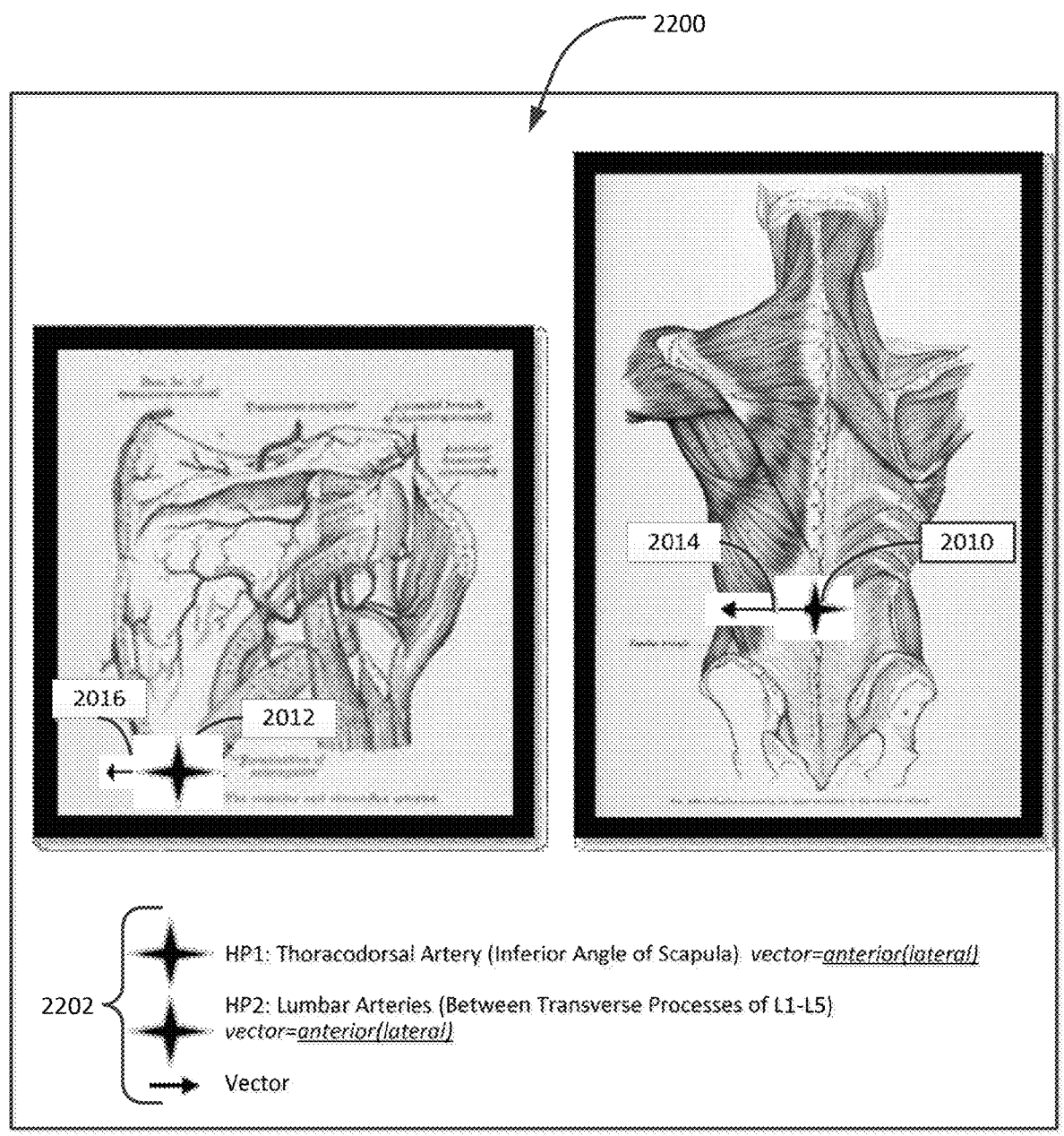
FIG. 22 shows the anatomical hand placement of Hand Placement 1 (HP1) and Hand Placement 2 (HP2) for System 3, Segment 5, atop a medical illustration from Gray's Anatomy (reproduced by permission) with the corresponding vector as indicated by an arrow.

FIG. 22 shows the anatomical hand placements for what is depicted in FIG. 20. Using medical illustration 2200, the activation point of HP1 2010 at the thoracodorsal artery is indicated the star as a notation as previously mentioned. The hand placement HP2 2012 at the lumbar arteries is indicated by the star at 2204. Gliding HP1 2010 along the vector 2014 occludes the main arterial supply for the thoracodorsal artery according to the concept of Compression X Glide=Compression(Glide)=Vector of Tension at 90°. Gliding HP2 2012 along the vector 2016 similarly occludes the main arterial supply for the Lumbar Arteries. A legend 2202 accompanies the medical illustration 2200 to provide additional information concerning the hand placements HP1 2010 and HP2 2012.

Figure 23:
FIG. 23 shows the local neurovascular stretch called the Local Stretch in the Neurovascular portion of Touch/Activation/Pulse/Neurovascular Stretch or TAPN framework for System 3, Segment 5.
Figure 24:
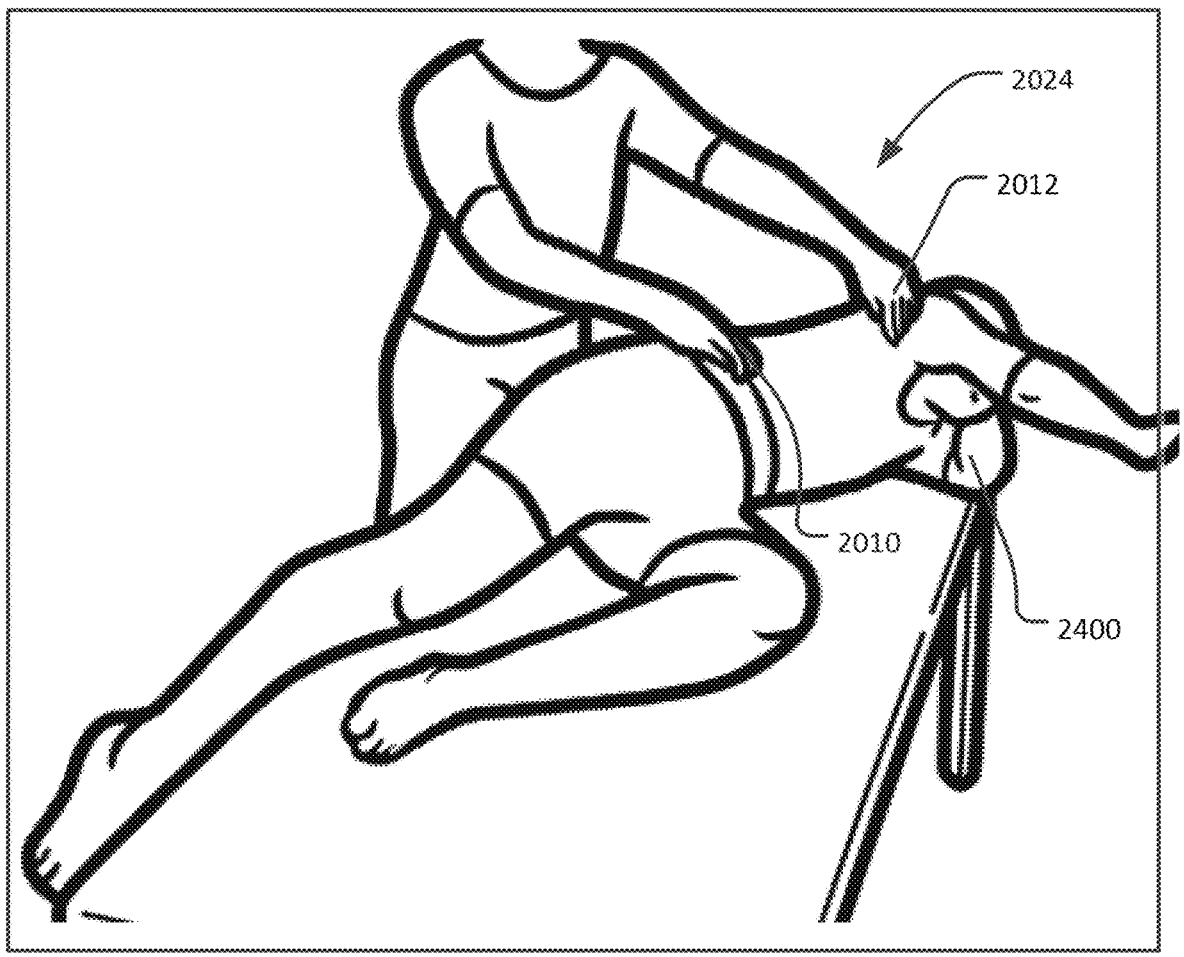
FIG. 24 shows the central neurovascular stretch called the Central Stretch in the Neurovascular portion of Touch/Activation/Pulse/Neurovascular Stretch or TAPN framework for System 3, Segment 5.

FIG. 23 demonstrates use of a combined approach for the local stretch 2022 targeting occlusive treatment targeting the thoracodorsal and ventral lumbar rami. The patient is demonstrating a hip extension with adduction and internal rotation of the hip, together with rotation of the contralateral lumbar region. HP1 2010 and HP2 2012 are being maintained simultaneously at the thoracodorsal and ventral lumbar rami using the correct vectors 2014, 2016 (see FIG. 22). If more nerve stretch is needed to reach the approximate 15% required to occlude blood vessels surrounding the nerve, and the patient can tolerate the movement, then a central stretch 2024 may be done as demonstrated in FIG. 24 as described in the Neurovascular Stretch row 2020 of FIG. 20. This also demonstrates the combined approach where HP1 2010 is being maintained at the same time as the local stretch 2012, with the assistance of the practitioner. Additionally, the patient has assisted with flexing 2400 the neck and the shoulder with the elbow extending and thumb pointing down, in order to provide the central stretch 2024 which enhances the effect. The central stretch 2406 may be left out, or the neurovascular stretch as a whole may be left out if a patient cannot tolerate the movements according to the variations.

Working Example 4—Neck Pain

FIG. 25 shows a TAPN framework box 2500 that may be provided by reporting from a computer database for use in guiding practitioners. The taxonomy code 2502 of "4.1.1" identifies System 4 which is the Cranium, Face and Anterior Neck, Segment 1 which is the Extrinsic Lumbar Segment of that System, and a Structure 1 which is the occipitalis muscle of that Segment. This taxonomy is also related as a segue structure 2504 indicating that there is fascial connectivity to System 3 which Spine and Thorax System. The Touch row 2506 provides useful information concerning the origins, insertions, blood supply and innervation for use as a reference tool in order to guide palpation of the correct structure and review anatomy according to Phase 601 (see FIG. 6A). The Activation row 2508 corresponding to Phase 605 of FIG. 6A designates HP1 2510 as being on the occipital artery at the right nuchal line of the occipital bone. HP2 2512 is a double activation point that is placed on the occipital artery at the left nuchal line of the occipital bone. Row 2514 describes the vector 2514 for HP1 2510 as occurring to the anterior/medial indicating a direction of tension for HP1 2510 to create occlusion according to the concept of Compression X Glide=Tension at 9J. A second vector 2516 allocated to HP2 2512 is also drawn to the anterior/medial.

The Pulse row 2514 corresponds to Phase 613 of FIG. 6A and identifies the distal turbulent Pulse that will be felt at the activation points or HP1 2510 and HP2 2512. This is a double activation occurring at the right and left occipital arteries because both HP1 2510 and HP2 2512 serve as activation points.

The Neurovascular Stretch row 2520 corresponds to Phase 619 of FIG. 6B and lists two additional movement sequences for a local neurovascular stretch 2522 targeting the posterior auricular nerve. In this case, there is a local stretch addressing the posterior auricular nerve: (1) bilaterally through neck flexion, and/or (2) unilaterally by use of collateral neck rotation with side flexion and neck flexion. If tolerated by the patient, a central neurovascular stretch 2524 maybe provided by lumbar flexion, hip flexion, knee flexion, and ankle flexion performed in what is known in the art as the Reverse Child's Pose or the Child's Pose.

Figure 26:
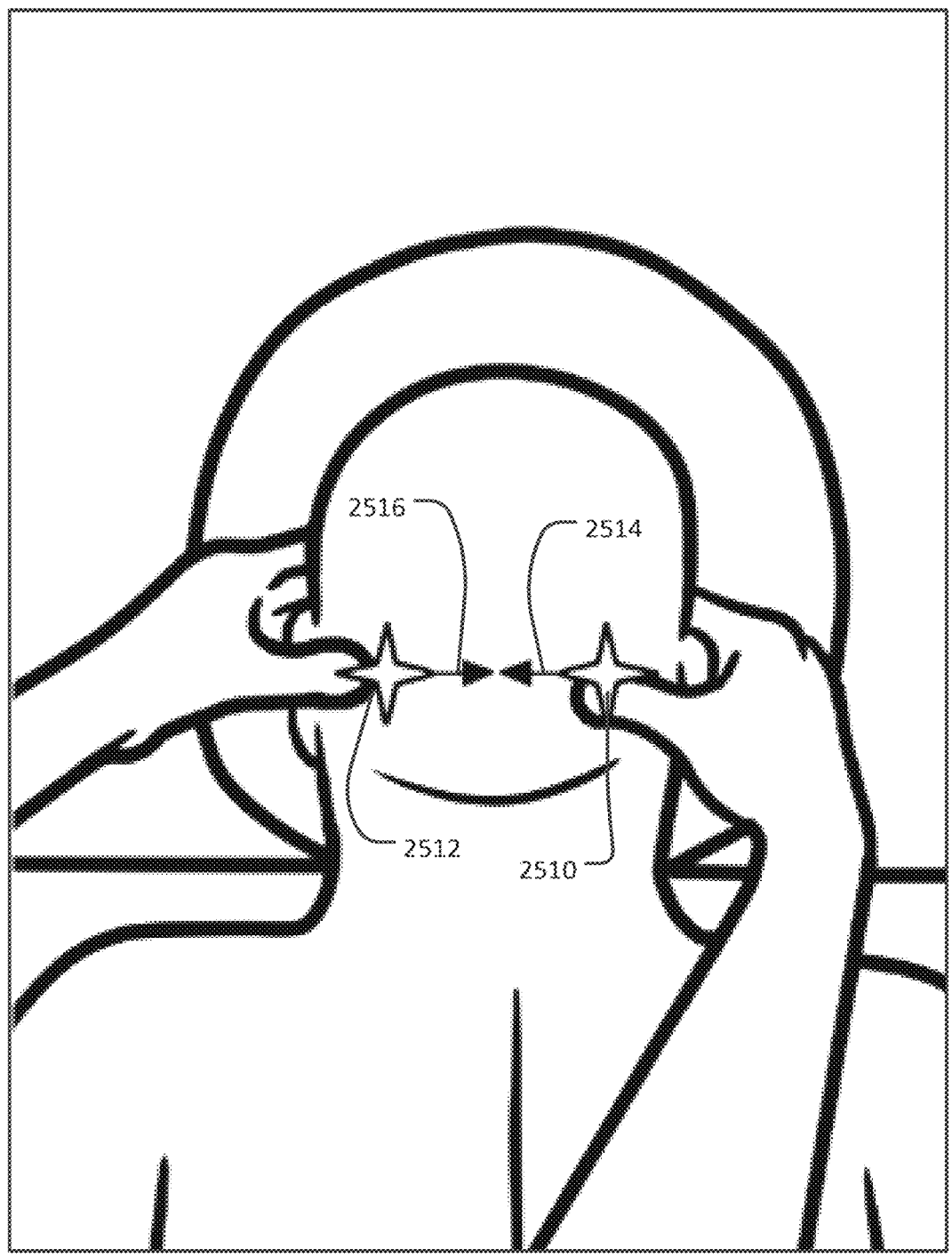
FIG. 26 shows the correct Hand Placement 1 (HP1) and Hand Placement 2 (HP2) for System 4, Segment 1, for use in the Activation component of Touch/Activation/Pulse/Neurovascular Stretch or TAPN framework.

In implementation, as shown in FIG. 26, if a patient presents with neck pain in proximity to the occipital bone, then a practitioner may provide ischemia to the occipital arteries using the framework box 2500 shown in FIG. 25 as the guide. After locating the structure using the anatomy reference in the Touch row 2506 and palpating the occipitalis muscle to elicit blood flow to the area, HP1 2510 may be placed at the right nuchal line of the occipital bone, and HP2 2512 at the left nuchal line for 30 seconds to 5 minutes. This is occurring in the Activation component 2508 of the framework 2500. Once the pulses at HP1 2510 and HP2 2512 have adequately diminished, the practitioner may move on to the next phase.

Figure 27:
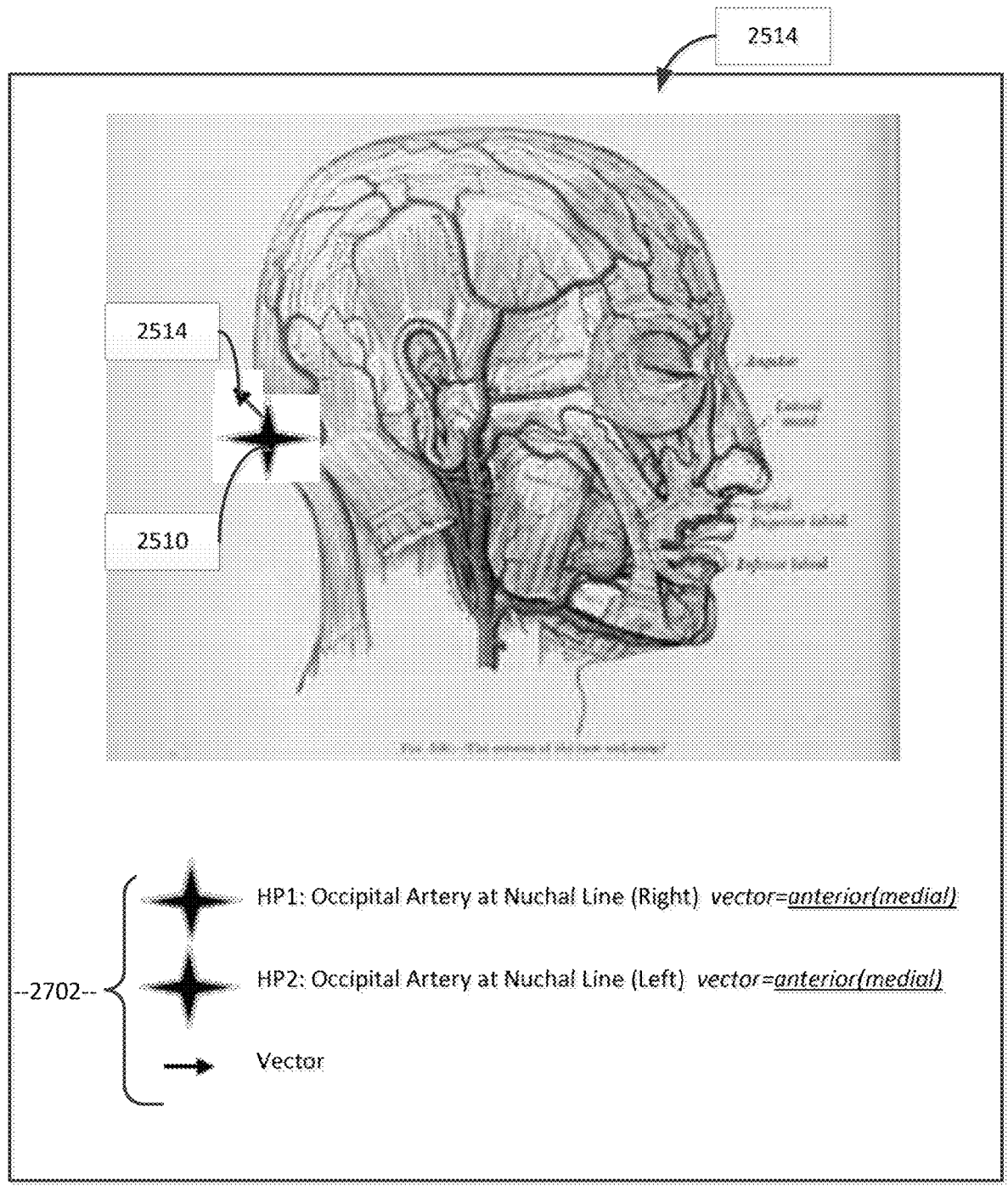
FIG. 27 shows the anatomical hand placement of Hand Placement 1 (HP1) and Hand Placement 2 (HP2) for System 4, Segment 1, atop a medical illustration from Gray's Anatomy (reproduced by permission) with the corresponding vector as indicated by an arrow.

FIG. 27 indicates the anatomical hand placements for what is depicted in FIG. 26. Using medical illustration 2700, the activation point at HP1 at the right nuchal line is indicated the star as a notation designating an activation point, as previously mentioned. HP2 2012 is performed in a mirror image on the left nuchal line. The vector 2514 proceeds as described in Activation row 2508 of FIG. 25 according to the concept of Compression X Glide=Compression(Glide)=Vector of Tension at 90°. A legend 2702 accompanies the medical illustration 2700.

Figure 28:
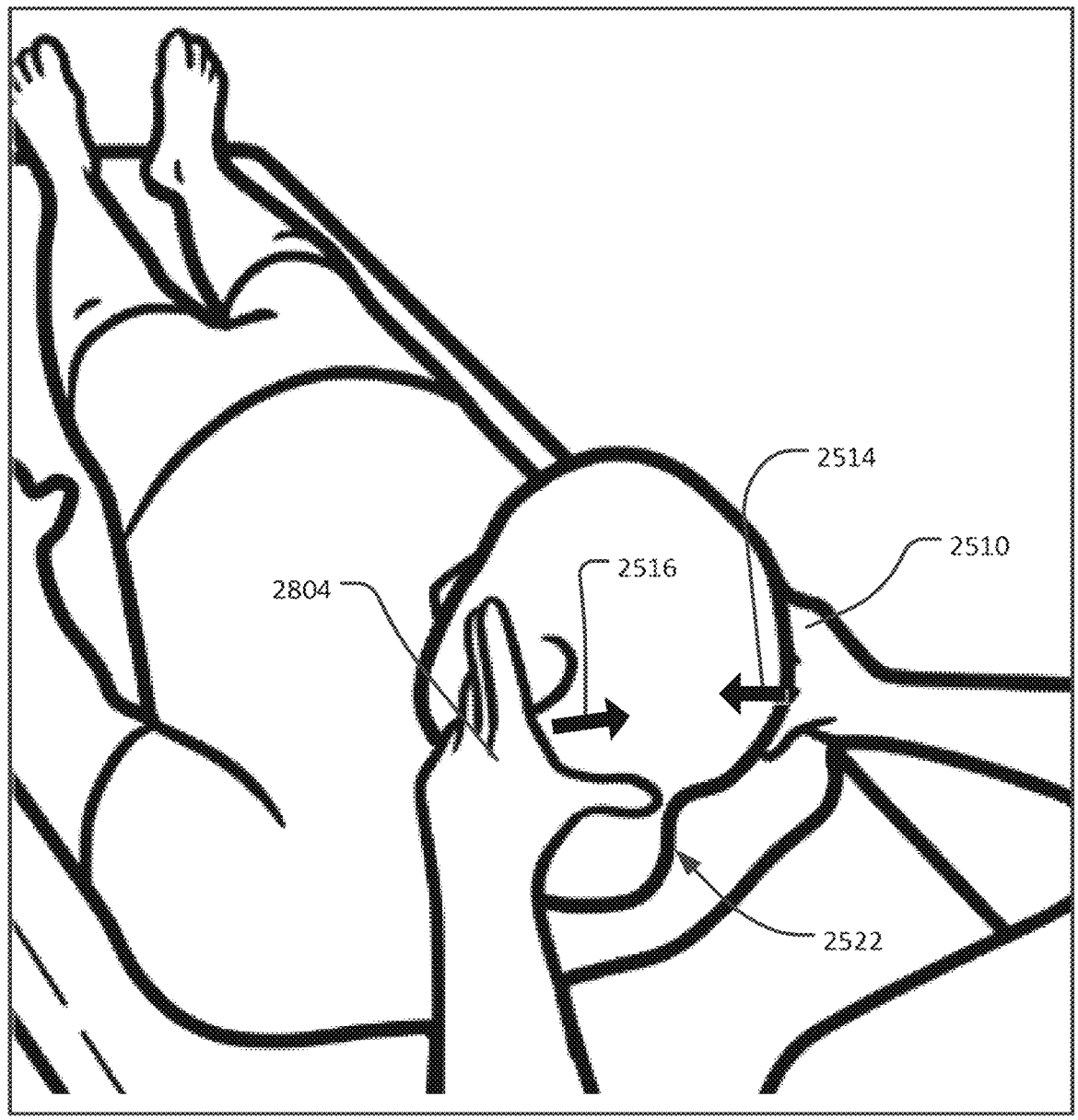
FIG. 28 shows the local neurovascular stretch called the Local Stretch in the Neurovascular portion of Touch/Activation/Pulse/Neurovascular Stretch or TAPN framework for System 4, Segment 1 Bilaterally.
Figure 29:
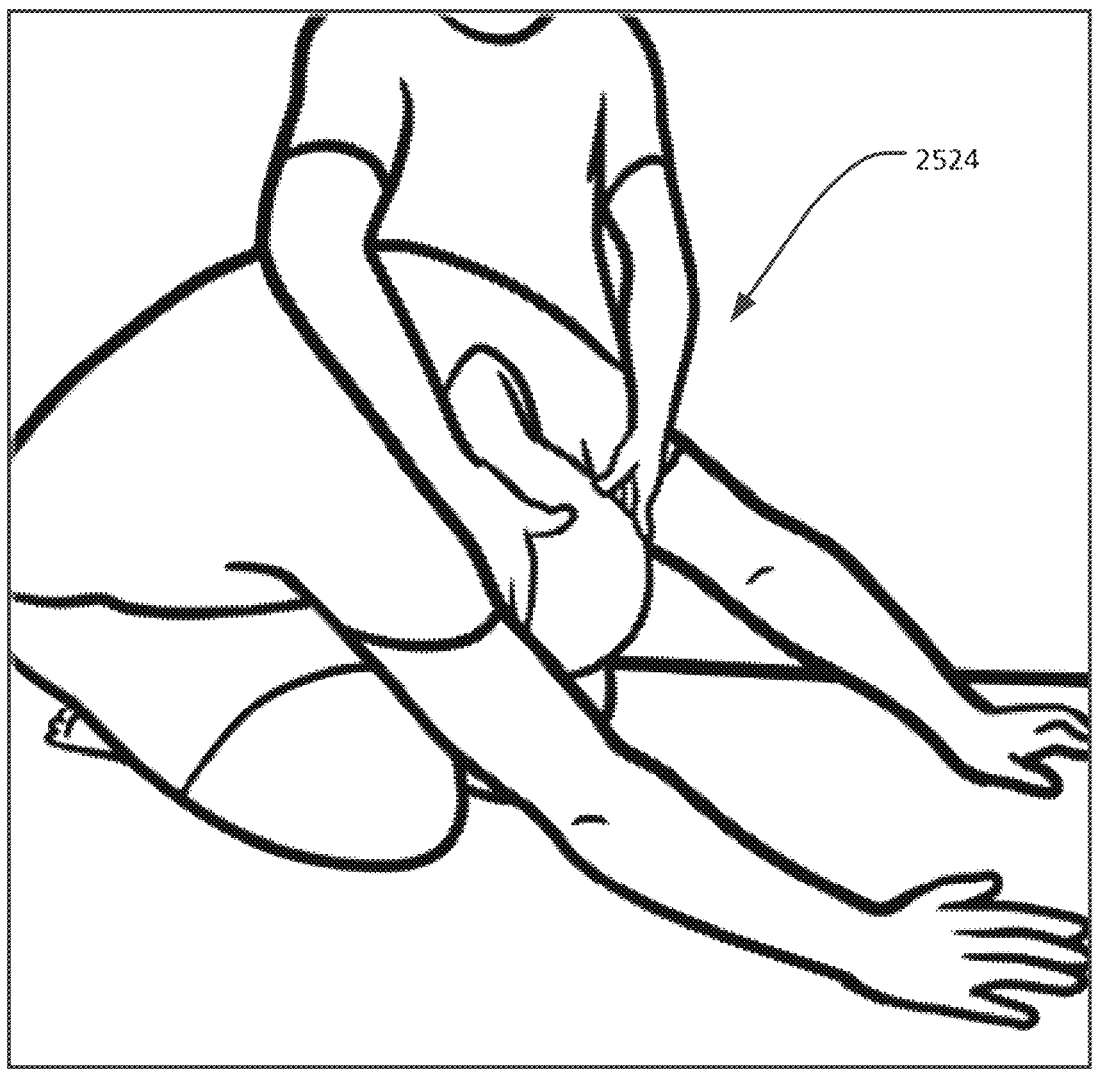
FIG. 29 shows the central neurovascular stretch called the Central Stretch in the Neurovascular portion of Touch/Activation/Pulse/Neurovascular Stretch or TAPN framework for System 4, Segment 1 Bilaterally.

FIG. 28 demonstrates use of a combined approach for the local stretch 2522 targeting the posterior auricular nerve. This means that HP1 2510 is being maintained simultaneously at the right occipital line using the correct vector 2514, while a local posterior auricular nerve stretch 2522 is being produced by the patient and/or the practitioner. If more nerve stretch is needed to reach the approximate 15% required to occlude blood vessels surrounding the nerve, and the patient can tolerate the movement, then a central stretch 2524 may be done as demonstrated in FIG. 29 as described in row 2520 of FIG. 25. This also demonstrates the combined approach where HP1 2510, is being maintained at the same time as the central stretch 2524, with the assistance of the practitioner. Additionally, the patient has assisted with flexing the lumbar region, the hip, the knee and the ankle. The patient as depicted is assuming the child's pose. The central stretch 2520 may be omitted, or the neurovascular stretch 2522, 2524 as a whole may be left out if a patient cannot tolerate the movements according to the variations.

Working Example 5—Sacral Sprain

FIG. 30 shows a TAPN framework box 3000 that may be provided by reporting form a computer database used to guide practitioners. The taxonomy code 3002 of 5.1.B.1 identifies System 5 which is the Pelvic, Abdominal and Visceral System, Segment 1.B constituting the Inferior Sacral Ligaments of that System, and Structure 1 which is the Sacrotuberous Ligament of that Segment. This taxonomy is also related as a segue Structure 3004 indicating that there is fascial connectivity to System 3 which is the Spine and Thorax System. The Touch row 3006 provides useful information concerning the origins, insertions, blood supply and innervation for use as a reference tool in order to guide palpation of the correct structure and review anatomy according to Phase 601 (see FIG. 6A). The Activation row 3008 corresponding to Phase 605 of FIG. 6A places HP1 3010 on the inferior gluteal artery at a location inferior to the piriformis. HP2 3012 makes this a double activation technique by placement for occlusion of the superior lateral sacral artery located at the posterior sacral foramen 1 and 2 of the sacrum. Activation row 3008 also describes a vector 3014 for HP1 3010 as occurring to the medial/inferoposterior indicating a direction of tension for HP1 3010 to enhance occlusion according to the concept of Compression X Glide=Tension at 90°. A vector 3016 at HP2 3012 similarly occurs to the anterior/medial direction.

The Pulse row 3018 corresponds to Phase 613 of FIG. 6A and identifies a pulse at each of the inferior gluteal artery and the lateral sacral artery that may be felt at HP1 3010 and HP2 3012, respectively.

The Neurovascular Stretch row 3020 corresponds to Phase 619 of FIG. 6B and lists two additional movement sequences for the local neurovascular stretch supplying the pudendal nerve. In this case the local stretch 3022 includes having the patient lie on one side to perform hip adduction with external rotation, flexion of the knee and inversion of the ankle. A central stretch 3024 constituting head flexion and contralateral hip extension with external rotation plus flexion of the knee may be used in addition to enhance the occlusive effect to the pudendal nerve.

Figure 31:
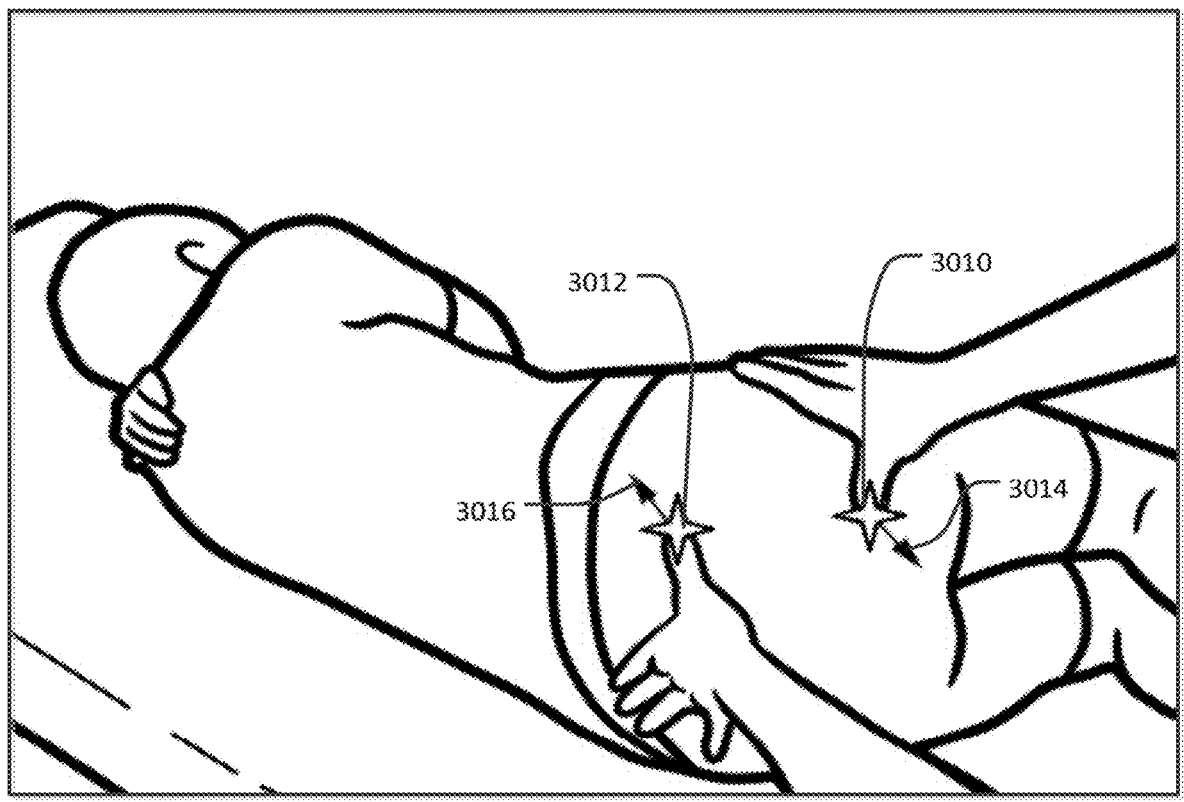
FIG. 31 shows the correct Hand Placement 1 (HP1) and Hand Placement 2 (HP2) for System 5, Segment 1B, for use in the Activation component of Touch/Activation/Pulse/Neurovascular Stretch or TAPN framework.

In implementation, as shown in FIG. 31, a patient presenting with a deep gluteal or sacral pain is lying on her side. A practitioner is administering treatment according to the TAPN framework of FIG. 30. HP1 3010 is positioned proximate the inferior gluteal artery at a location inferior to the piriformis. HP2 3012 is proximate to the superior lateral sacral artery at the posterior sacral foramen 1 and 2 of the sacrum. These placements may be administered for 30 seconds to 5 minutes as described for vectors 3014, 3016 (see FIG. 30). This occurs according to the Activation row 3008 of the framework box 3000. Once the pulses at HP1 3010 and HP2 3012 have adequately diminished, the practitioner can move on to the next phase.

Figure 32:
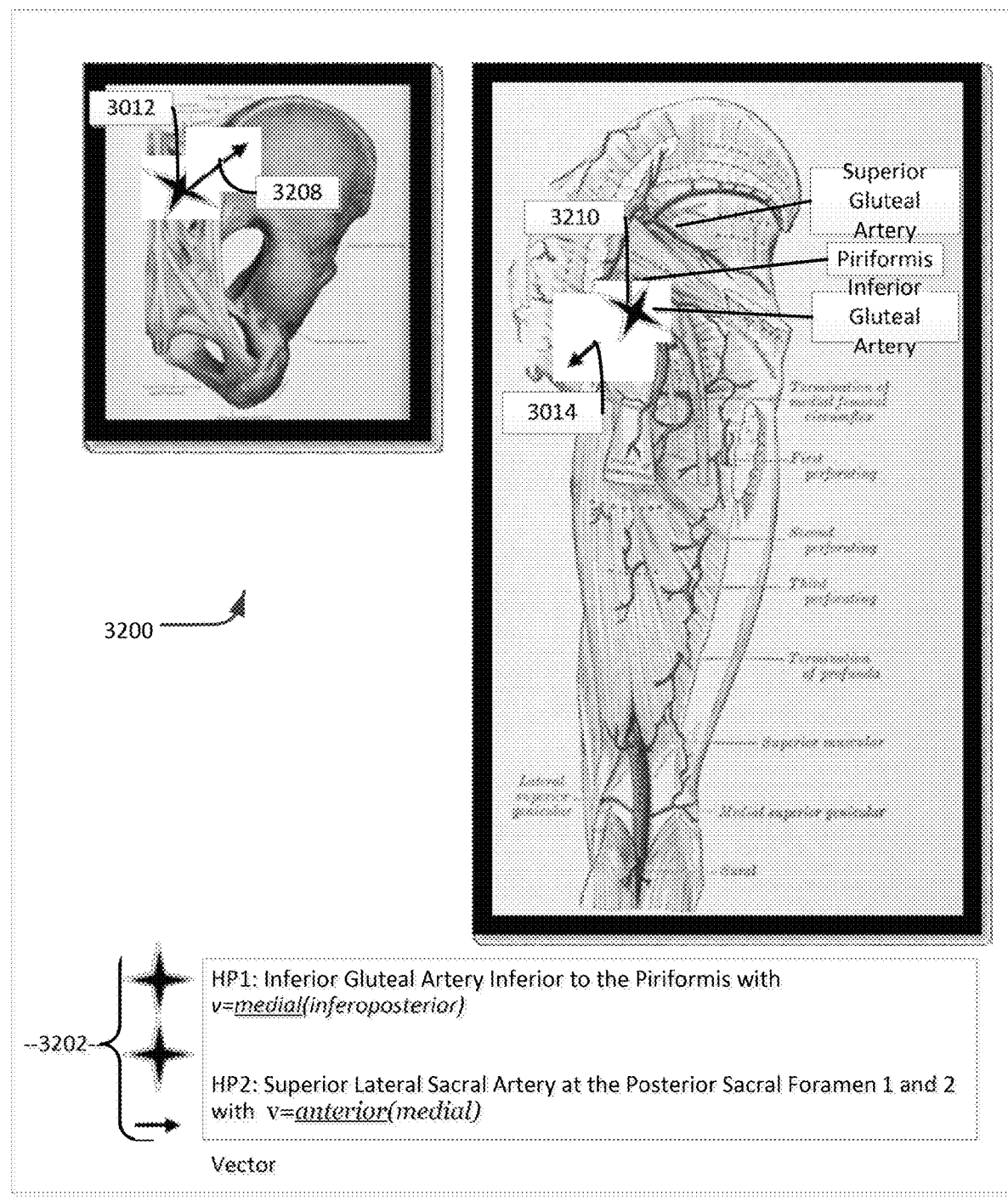
FIG. 32 shows the anatomical hand placement of Hand Placement 1 (HP1) and Hand Placement 2 (HP2) for System 5, Segment 1B, atop a medical illustration from Gray's Anatomy (reproduced by permission) with the corresponding vector as indicated by an arrow.

FIG. 32 shows the anatomical hand placements for what is depicted in FIG. 31. Medical illustration 3200 shows the activation point HP1 3010 at the inferior gluteal artery. HP2 3012 is proximate the superior lateral sacral artery. A medial/inferoposterior gliding motion from HP1 3010 along vector 3014 occludes the main arterial supply for the inferior gluteal region. A gliding motion from HP2 3012 along vector 3016 occludes the blood supply from the superior lateral sacral artery. A legend 3202 accompanies the medical illustration 3200.

Figure 33:
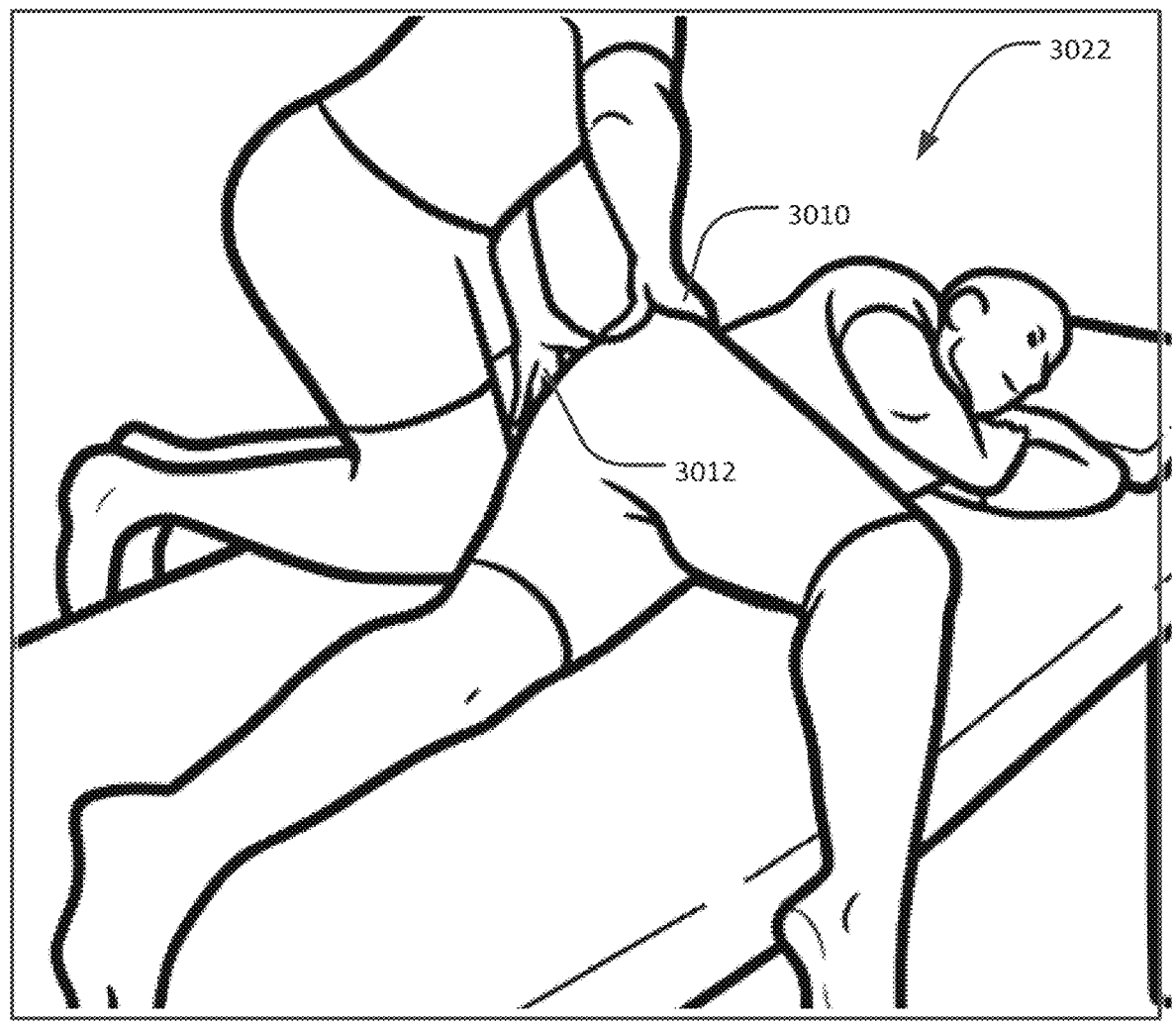
FIG. 33 shows the local neurovascular stretch called the Local Stretch in the Neurovascular portion of Touch/Activation/Pulse/Neurovascular Stretch or TAPN framework for System 5, Segment 1B.
Figure 34:
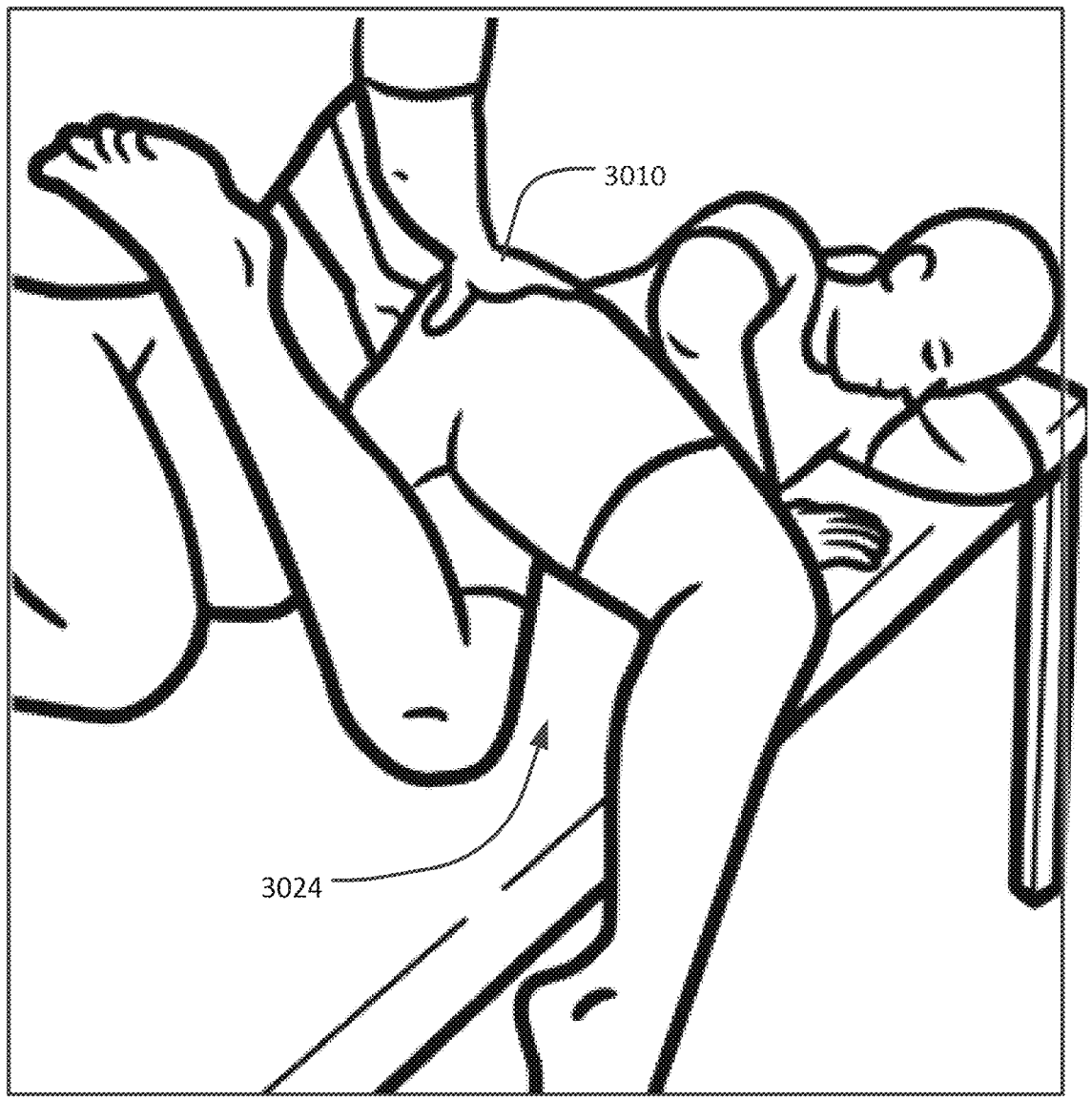
FIG. 34 shows the central neurovascular stretch called the Central Stretch in the Neurovascular portion of Touch/Activation/Pulse/Neurovascular Stretch Framework for System 5, Segment 1B.

FIG. 33 demonstrates use of a combined approach for the local stretch 3002 targeting the pudendal nerve. This means that HP1 3010 and HP2 3012 are being maintained simultaneously at the inferior gluteal artery and superior lateral sacral artery using the correct vectors 3014, 3016, while the pudendal nerve stretch 3022 is being produced by having the patient lie on her side to perform a hip adduction and external rotation with knee flexion and ankle inversion. If more nerve stretch is needed to reach the approximate 15% required to occlude blood vessels surrounding the pudendal nerve, and the patient can tolerate the movement, then a central stretch 3024 may be done as demonstrated in FIG. 34. This also demonstrates the combined approach where HP1 and HP2 3402, are being maintained at the same time as the local stretch 3022, with the assistance of the practitioner. Here the patient has assisted the central stretch 3024 by performing a head flexion with hip external rotation and knee flexion.

Figure 35:
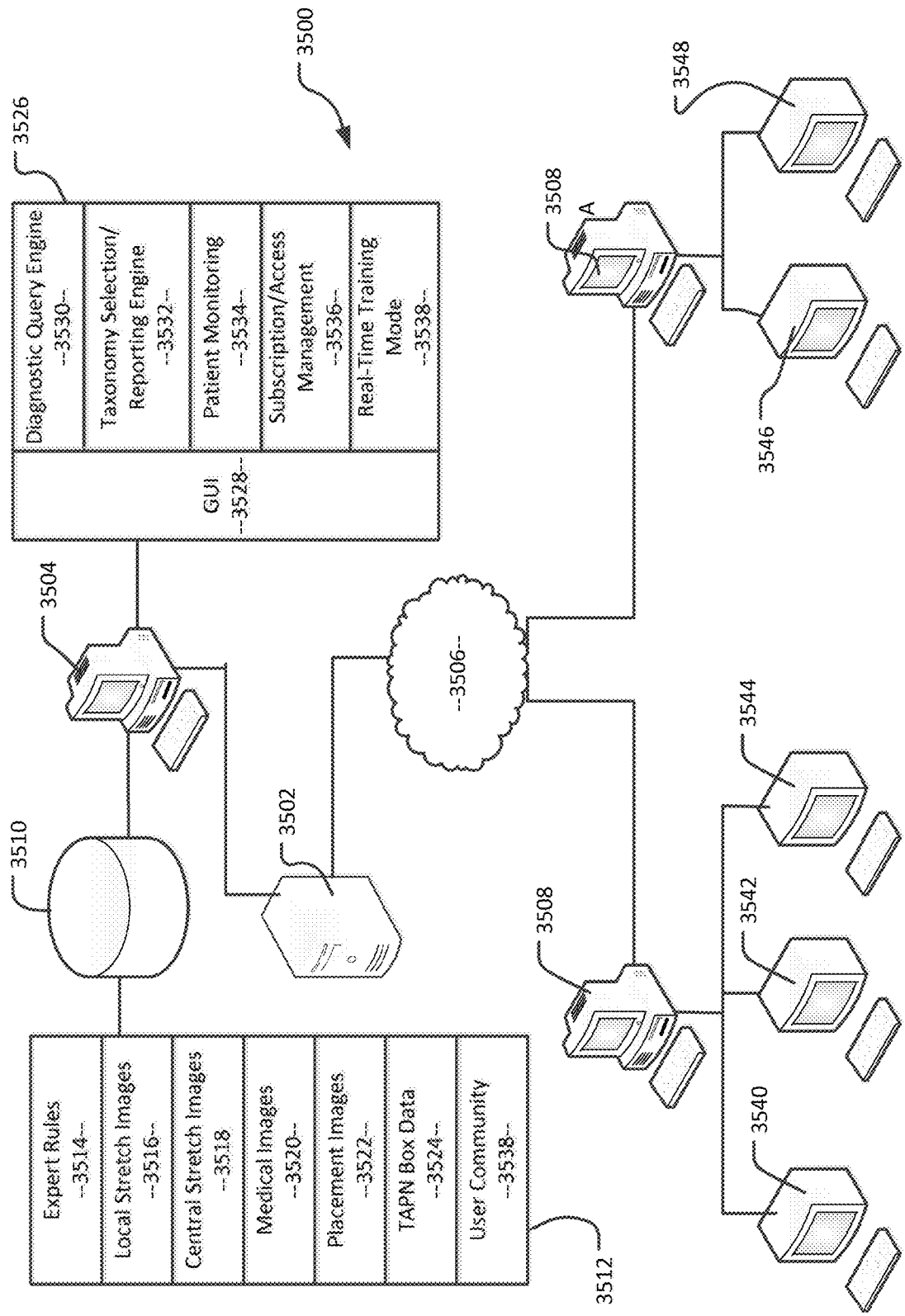
FIG. 35 shows a computer system that may be used as a guide in performing therapies as disclosed herein, and as an educational or training aid.

FIG. 35 shows a special purpose computer system 3500 that is constructed to facilitate training and education for the medical treatment of RI. The system 3500 may also be used as an in-practice guide for the treatment of patients who are in need of the treatment of RI. A central server 3502 connects a central processing station 3504 to the Internet 3506. Any number of network hosts 3508, 3508A, etc. . . . may also be connected to the central server 3502 through the Internet 3506.

A database 3510 is connected to the central processing station 3504. The database has a variety of components, such as relational database tables 3512 which may be located at a central location or in a distributed database. A system of expert rules 3514 is established by a skilled practitioner to assist in the diagnosis and treatment of RI. A practitioner of this skillset may be, for example, a person with a doctorate in Physical Therapy or another expert in anatomy and manual therapy. Access to these rules permits reporting and presentation of images shown in Working Examples 1-5 to practitioners to facilitate educational training in the treatment of injuries as a result of RI, as well as the actual treatment of the injury itself.

In one embodiment, software resident on the server 34502 or processing station 3504 may include a system reporting functionality (through use of GUI 3528) that guides practitioners who are implementing a treatment modality for a Structure of the human body. The reporting functionality may, for example, utilize an image of the human body with sequential click-downs that proceed through a system of taxonomy to arrive as a Structure in need of treatment. Once the Structure is selected, the reporting functionality may provide images and other data that guide the practitioner through the TAPN framework as shown in processes 600 (FIGS. 6A and 6B) and 700 (FIG. 7).

The images may include a table of local stretch images 3516, which may be images in the nature of FIGS. 11, 18, 23, 28 and 33 described above, as well as any other images of stretches undertaken to induce ischemia of nerves by virtue of local stretches according to the TAPN framework and taxonomy system discussed above. The images also include central stretch images 3518 which are images in the nature of FIGS. 12, 19, 24, 29 and 34 described above, as well as any other images of stretches undertaken to induce ischemia of nerves by virtue of central stretches according to the TAPN framework and taxonomy system discussed above. Generally speaking, central stretches are stretches designed to enhance the ischemic effect of local stretches, but which may be less well tolerated by a patient who has suffered an injury.

The database 3510 also includes medical images 3520. These include images in the nature of FIGS. 10, 17, 22, 27, and 32 as described above, as well as any other images of stretches undertaken to induce ischemia of nerves by virtue of local stretches according to the TAPN framework and taxonomy system discussed above. Generally speaking, these images are anatomical diagrams showing hand placements and associated vectors for various positions of HP1 and HP2 for a particular treatment protocol. This information may be supplemented by hand placement images 3522, which are preferably photographs, drawings or other images showing the positions for HP1 and HP2 on a human body according to a particular treatment protocol. A table of TAPN box data 3524 provides information that may be used to fill the fields of a TAPN box as are shown in FIGS. 8, 15, 20, 25 and 30. FIG. 14 is a generic TAPN box describing the information that may be provided to a TAPN box.

The central processing station 3504 may be provided with program logic that is organized into functional blocks of logic 3526, which may be for example, subroutines or objects that interact with a user through graphical user interface 3528. A diagnostic query engine 3530 engages in a dialogue with a practitioner/user, such as users connected to the network hosts 3508, 3508A. The query may be any query that is useful in guiding practitioners to arrive at a reported TAPN box in the nature of what is shown in FIG. 14. As one example of this, there may be shown an image of a human body 3600 as in FIG. 16. This image is divided into the various taxonomical systems, e.g., System 1—Lower Extremity 3602; System 2—Upper Extremity 3604; System 3—Spine and Thorax 3606; System 4—Cranium, Face and Anterior 3608; and System 5—Pelvic, Abdominal and Visceral 3610. There may be a dialogue, such as prompting the practitioner/user to click on any System where the patient is experiencing swelling, pain, tingling, or any other dysfunctional symptoms. Clicking upon one or more of these Systems according to a class of symptoms causes a taxonomy selection and reporting engine 3532 to generate a graphic image report 3700 of one or more Segments with structure fields 3702, 3704, 3706, 3708, each showing general areas for hand placements that may be used to treat one or more structures that are implicated in the diagnosis. Clicking upon one or more of the structure fields causes the taxonomy selection and reporting engine 3532 to access the database 3510 and generate a TAPN box (see FIG. 14) for RI treatment of the structure as guided by the system of expert rules 3512.

A patient monitoring segment 3534 tracks what treatments have been performed on each patient by taxonomy code, how well the treatment was tolerated, and whether the treatments caused any improvements or additional symptoms to occur. The occurrence of improvements or additional symptoms can be a significant factor in applying the system of expert rules. For example, in a patient who complains of both knee and spinal pain, compensation for the knee injury when striding may cause misalignments to occur in the hip, back and neck. Therefore, while all of these problems may be treated, treatment of the knee may be regarded as the primary goal with the other problems being secondary, and this may be confirmed by monitoring to assess whether the secondary problems diminish with improvement of the injury to the knee. Thus, the system of expert rules 3512 and the taxonomy selection and reporting engine 3532 may ascertain improvements or additional problems as a factor in determining the selection of treatments by taxonomic codes.

The database 3510 is optionally a propriety database in the sense that a subscription or access management engine 3536 excludes unauthorized users. For example, users connected through the network hosts 3508, 3508A may pay a monthly or annual subscription access fee. This community of users may also be able to share data for TAPN frameworks of their own creation by uploading these to a user community database segment 3538, which may also contain user community notes regarding specific TAPN protocols, such as problems or benefits observed with these protocols, suggested improvements, and whether patients generally well-tolerate specific movements suggested by thee protocols.

The system 3500 may be configured for real-time training or education 3538 through use of menu options presented through the GUI 3528. Thus, a user may place the system 3500 in a mode where patient data is only transiently retained for patient monitoring 3534 during the course of a training session where, for example, there may be a volunteer patient who has no actual injury but has been coached to complain of the symptoms that would be present in case of an actual injury. Alternatively, the menu system for the real-time training mode 3538 may be used to place the system 3500 in an interactive dialogue that demonstrates use of the system to a practitioner/user, for example, by interacting with the GUI 3528 to arrive at the TAPN boxes shown in FIGS. 8, 15, 20, 25 and 30 and having the practitioner demonstrate the treatment techniques of working Examples 1-5 to a course instructor, either on a living person or a dummy that is specially provided for training purposes.

There may be any number of network hosts 3508, 3508A. By way of example, each of network hosts 3508, 3508A may be for local networks allocated to a physical therapy practice located at a single brick-and-mortar address. For larger enterprises operating out of different addresses, the network hosts may be for wide area network or a virtual private network.

Although FIG. 35 shows conceptually that the central processing station 3504 and the database 3510 are located in a central facility away from the network hosts 3508, 3508A, it will be appreciated that this arrangement may be replaced by distributed processing and distributed databasing techniques disbursing these functionalities through use of the Internet 3506. It is also possible to have the database 3510 and the logic 3526 replicated on the network hosts 3508, 3508A for local use such that interaction with the central server 3502 is minimized. For example, the database 3510 and logic 3526 may be configured to run locally while the central processor merely manages subscription access 3536 and provides periodic updates for the content of database 3510. The network host 3508 may host any number of networked workstations 3540, 3542, 3544 while the network host 3508A is similarly connected to workstations 3546, 3548. The workstations 3540-3548 may be, for example, places where practitioners are trained or where they perform treatments.

Figure 36:
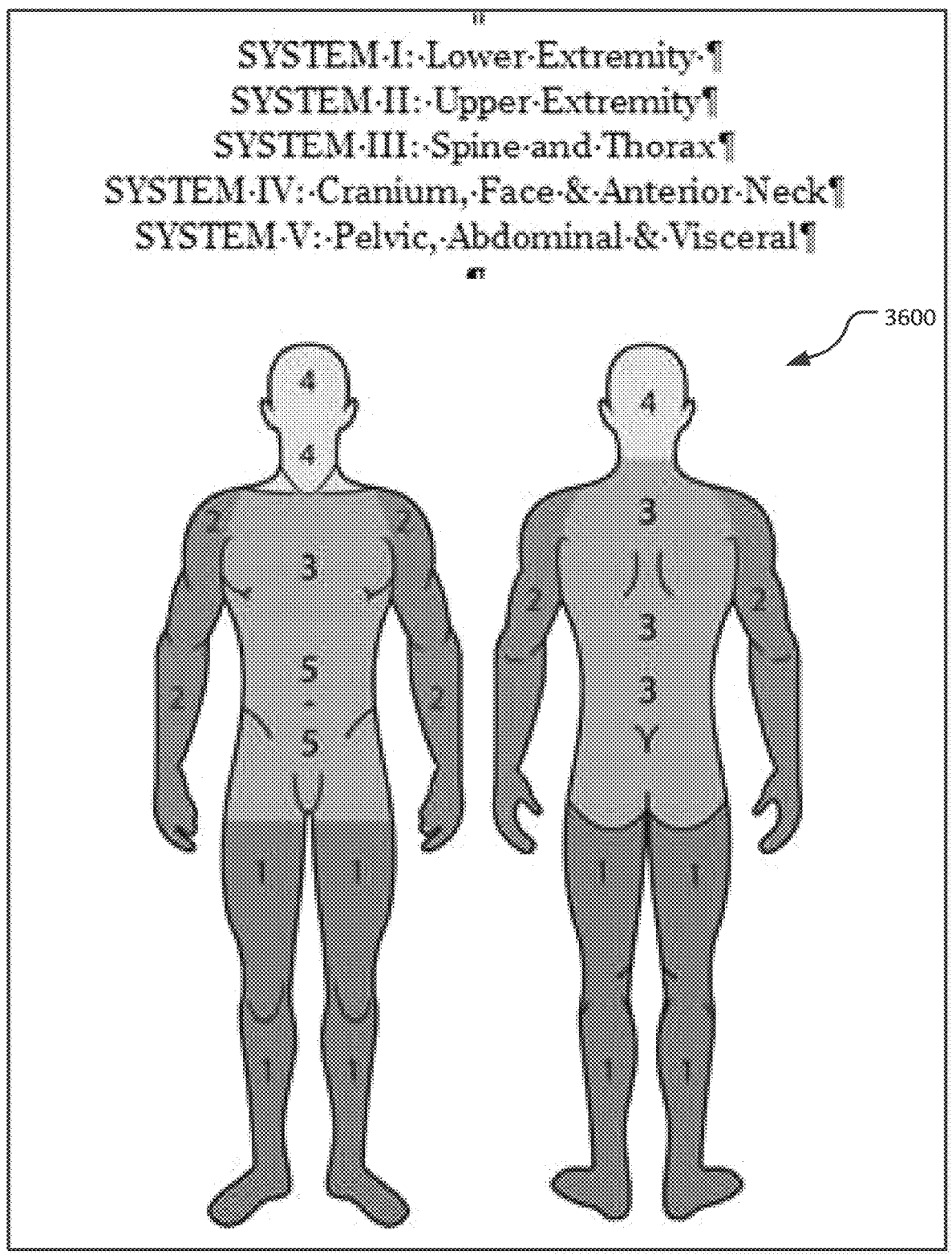
FIG. 36 shows an interactive component of a graphical user interface that may be utilized in selecting one or more taxonomical Systems of the human body as an aid to diagnosis and reporting of treatment modalities that are selected by a computer according to a system of expert rules.

FIG. 36 shows a graphical user interface (GUI) that may be utilized for purposes of reporting from the database 3510 to provide indicia that are useful for purposes of treatment and education as described above reporting purposes. A user need only click on a field that contains a system identifier in order to drill successively deeper into the taxonomy of System:Segment:Structure. Thus, if a user clicks on a particular System, such as System 3, the user will then be directed to a field-allocated breakout (not shown) of Segments for that System (System 3). The user may then click on a particular Segment to see all Structures for that Segment. Clicking on a Structure causes the computer system 3500 to generate a report that may, for example, include a TAPN table, anatomical drawings, and images that facilitate TAPN based treatment of the selected particular structure. It will be appreciated that the report may also include information for the treatment of additional or alternative structures that are associated as segue structures described above.

Program instructions and data for the operation of system 3500 may be stored on a computer readable form. A computer readable form may be, for example, a hard drive, DVD, CD-ROM, computer memory or memory stick.

Figure 37:
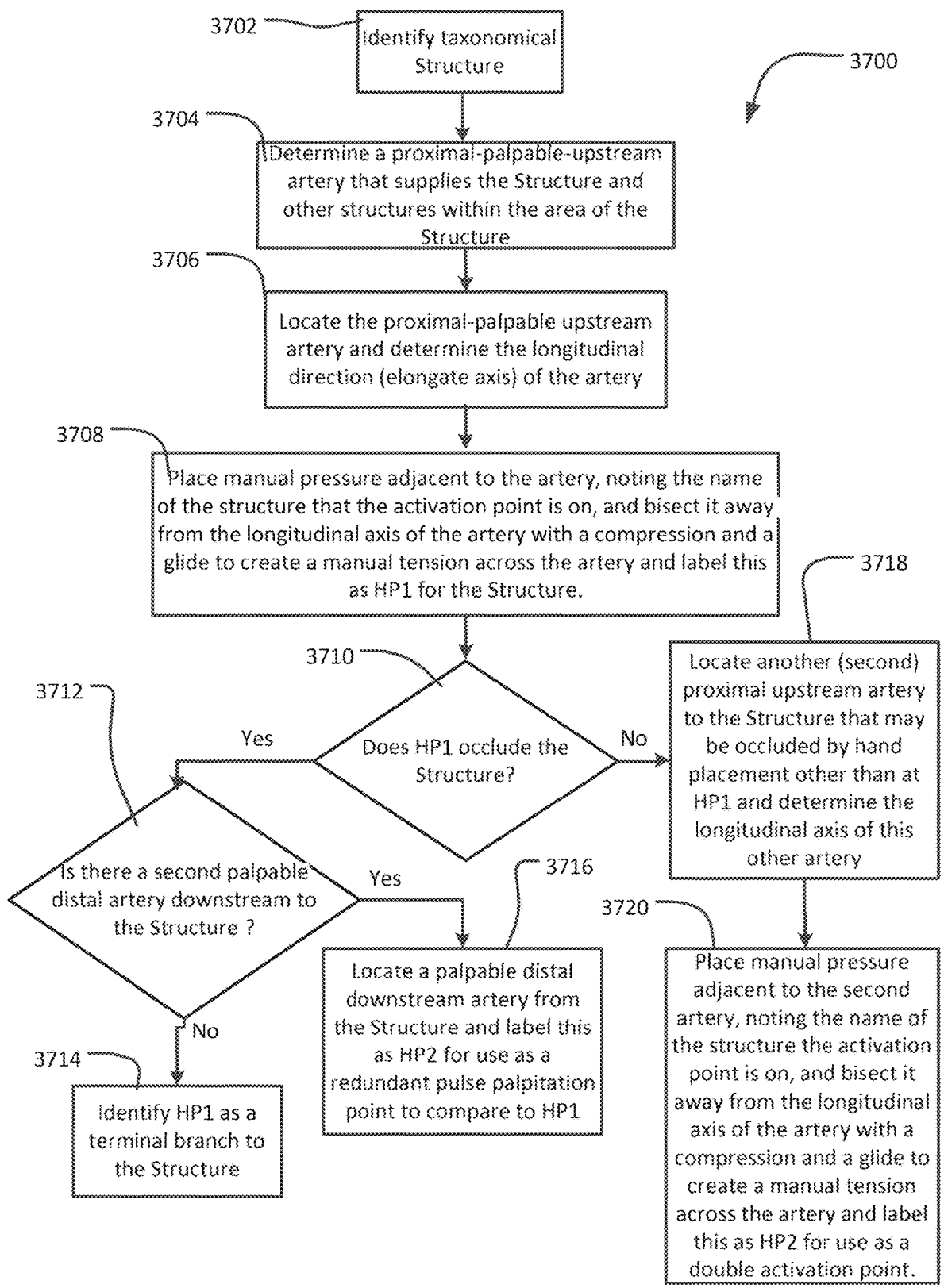
FIG. 37 is a flowchart of logic that may be utilized for the identification of Structures in developing an expert system of rules to positon compression and glide for the touch, activation and pulse activation stages for TAPN treatment of any Structure of the body.

FIG. 37 shows a logical process 3700 that may be utilized in developing an expert system of rules or data associations in determining the location of hand placements for TAPN treatment of any Structure in the human body. The process 3700 commences with identification 3702 of a taxonomical structure that is amendable to treatment. This may be, for example, discrete muscle or other component of anatomy having blood that is principally supplied by one or two main arteries. Next comes determination 3704 of a proximal-palpable-upstream artery that supplies the Structure and other structures within the area of the Structure. This may be done, for example, by consulting an anatomical diagram. Once the determination 3702 is made, it is possible to locate 3706 the proximal-palpable upstream artery on a test patient and determine the longitudinal direction (elongate axis) of the artery.

With the artery so located 3706, one can place 3708 manual pressure adjacent to the artery. Here it is also preferred to note the name of the structure where the activation point resides. The activation point is then moved to bisect away from the longitudinal axis of the artery with a compression and a glide to create a manual tension across the artery. This is a test to ascertain HP1 for the Structure. A second determination 3710 is made by ascertaining a pulse to determine whether the proposed HP1 occludes blood supply to the Structure as intended. If so, another determination 3712 is made, for example, by consulting an anatomical diagram, whether there is a second palpable distal artery downstream from the Structure. If the determination 3712 is negative, then HP1 is a terminal branch to the Structure and no HP2 is required. If the determination 3712 is positive, then HP2 is determined on the test patient by locating 3716 a palpable distal downstream artery from the Structure. This manner of HP2 may be used as a redundant pulse palpitation point to compare to HP1.

If the determination 3710 is negative, then one may locate 3718 another (second) proximal upstream artery to the Structure that may be occluded by hand placement other than at HP1. The longitudinal axis of this second artery is determined for purposes of establishing occlusion by compression plus glide. On the test patient, one may place 3720 manual pressure adjacent to the second artery. The name of the structure at the activation point is preferably recorded. One may then use compression plus glide to move the activation point HP2, bisecting away from the longitudinal axis of the artery to create a manual tension across the artery. This manner of HP2 is a double activation point because there are two points of occlusion for the same Structure. Pulses may be taken from the test patient to confirm that occlusion/activation has occurred.

Figure 38:
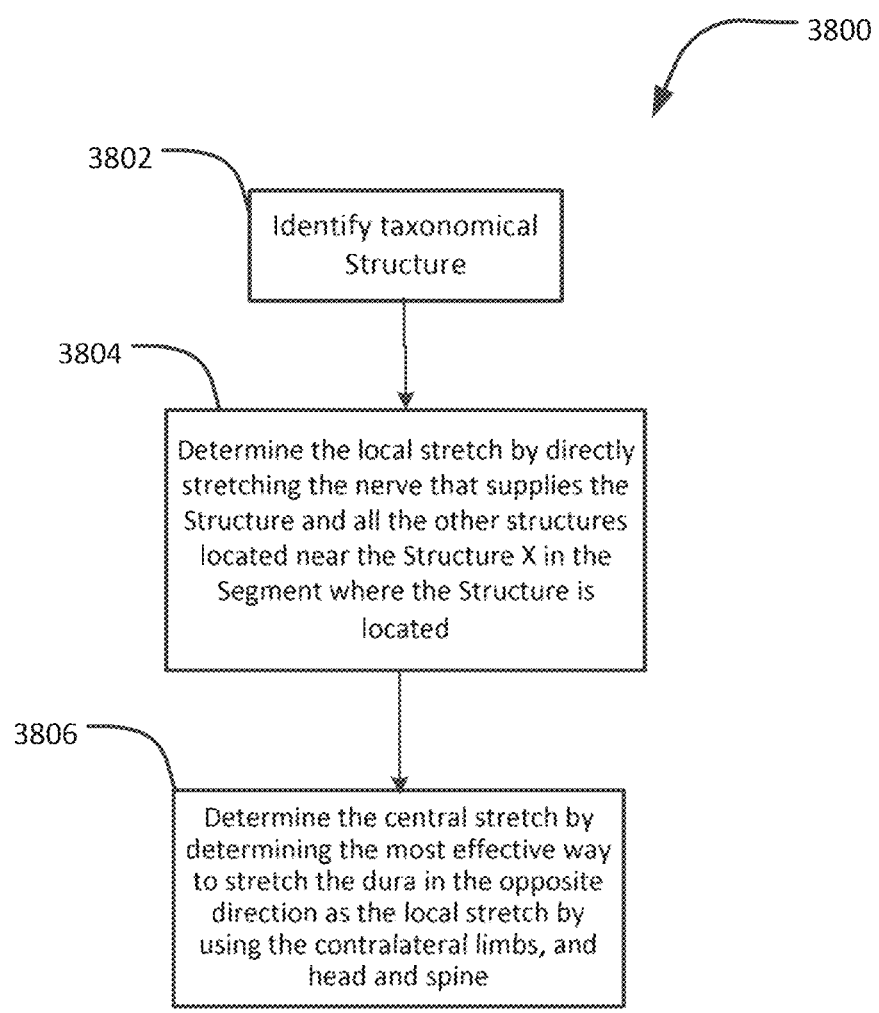
FIG. 38 is a flowchart of logic that may be utilized to develop an expert system of rules providing for local and central stretches in the neurovascular stretch stage for TAPN treatment of any Structure of the body.

FIG. 38 shows a logical process 3800 that may be utilized in developing central and local stretches for TAPN treatment of any Structure in the human body. The process 3800 begins with identification 3802 of a structure. This proceeds in the same manner as is done for identification 3702 of FIG. 37. A local stretch is determined 3804 as one or more bodily motions that directly stretch the nerve that supplies the Structure together with any other structures located near the Structure in the Segment where the Structure resides. A central stretch is determined 3806 as one or more bodily motions that effectively stretch the dura in the opposite direction as the local stretch by using the contralateral limbs, and head and spine.

Table 1 below provides a list of Structures that, among others, may be determined for treatment of RI and developed using logical processes 3700, 3800:

TABLE 1

| | Structures for TAPN Treatment | |
|---|---|---|
| System No. | System | Structure |
| 1 | Lower Extremity | Abductor Digiti Minimi (Layer 1) |
| 1 | Lower Extremity | Abductor Hallucis (Layer 1) |
| 1 | Lower Extremity | Adductor Brevis |
| 1 | Lower Extremity | Adductor Hallucis (Layer 3) |
| 1 | Lower Extremity | Adductor Longus |
| 1 | Lower Extremity | Adductor Magnus |
| 1 | Lower Extremity | Anterior Cruciate Ligament |
| 1 | Lower Extremity | Articularis Genu |
| 1 | Lower Extremity | Biceps Femoris(Long Head) |
| 1 | Lower Extremity | Biceps Femoris(Long Head) |
| 1 | Lower Extremity | Biceps Femoris(Short Head) |
| 1 | Lower Extremity | Dorsal Interossei |
| 1 | Lower Extremity | Extensor Digitorum Brevis & Extensor Hallucis Brevis |
| 1 | Lower Extremity | Extensor Digitorum Longus |
| 1 | Lower Extremity | Extensor Hallucis Longus |
| 1 | Lower Extremity | Flexor Digiti Minimi & Opponens Digiti Minimi (Layer 3) |
| 1 | Lower Extremity | Flexor Digitorum Brevis (Layer 1) |
| 1 | Lower Extremity | Flexor Digitorum Longus |
| 1 | Lower Extremity | Flexor Hallucis Brevis (Layer3) |
| 1 | Lower Extremity | Flexor Hallucis Longus |
| 1 | Lower Extremity | Flexor Retinaculum |
| 1 | Lower Extremity | Gastrocnemius & Achilles Tendon |
| 1 | Lower Extremity | Gluteus Maximus |
| 1 | Lower Extremity | Gluteus Medius |
| 1 | Lower Extremity | Gluteus Minimus |
| 1 | Lower Extremity | Gracilis |
| 1 | Lower Extremity | Iliacus |
| 1 | Lower Extremity | Iliotibial Band |
| 1 | Lower Extremity | Inferior Extensor Retinaculum |
| 1 | Lower Extremity | Inferior Gemelli |
| 1 | Lower Extremity | Interosseus Membrane of Leg |
| 1 | Lower Extremity | Joint Capsules |
| 1 | Lower Extremity | Lateral Collateral Ligament of Ankle |
| 1 | Lower Extremity | Lateral Collateral Ligament of Knee |
| 1 | Lower Extremity | Lateral Meniscus |
| 1 | Lower Extremity | Lumbricals (Layer 2) |
| 1 | Lower Extremity | Medial Collateral Ligament of Knee |
| 1 | Lower Extremity | Medial Collateral Ligaments of Ankle (Deltoid Ligament) |
| 1 | Lower Extremity | Medial Meniscus |
| 1 | Lower Extremity | Obturator Externus |
| 1 | Lower Extremity | Obturator Internus Distal ⅔(Insertion) |
| 1 | Lower Extremity | Patellar Ligament |
| 1 | Lower Extremity | Pectineus |
| 1 | Lower Extremity | Peroneus Brevis |
| 1 | Lower Extremity | Peroneus Longus |
| 1 | Lower Extremity | Peroneus Tertius |
| 1 | Lower Extremity | Piriformis |
| 1 | Lower Extremity | Plantar Calcaneonavicular Ligament (Spring Ligament) |
| 1 | Lower Extremity | Plantar Fascia |
| 1 | Lower Extremity | Plantar Interossei (Layer 4) |
| 1 | Lower Extremity | Plantaris |
| 1 | Lower Extremity | Plica |
| 1 | Lower Extremity | Popliteus |
| 1 | Lower Extremity | Posterior Cruciate Ligament |
| 1 | Lower Extremity | Psoas Major |
| 1 | Lower Extremity | Psoas Minor |
| 1 | Lower Extremity | Quadratus Femoris |
| 1 | Lower Extremity | Quadratus Plantae (Layer 2) |
| 1 | Lower Extremity | Rectus Femoris |
| 1 | Lower Extremity | Sartorius |
| 1 | Lower Extremity | Semimembranosus |
| 1 | Lower Extremity | Semimembranosus |

TABLE 1-continued

Structures for TAPN Treatment

| System No. | System | Structure |
|---|---|---|
| 1 | Lower Extremity | Semitendinosus |
| 1 | Lower Extremity | Semitendinosus |
| 1 | Lower Extremity | Soleus & Achilles Tendon |
| 1 | Lower Extremity | Superior Extensor Retinaculum |
| 1 | Lower Extremity | Superior Gemelli |
| 1 | Lower Extremity | Tensor Fascia Lata |
| 1 | Lower Extremity | Tibialis Anterior |
| 1 | Lower Extremity | Tibialis Posterior |
| 1 | Lower Extremity | Transverse Intermuscular Septum |
| 1 | Lower Extremity | Vastus Intermedius |
| 1 | Lower Extremity | Vastus Lateralis |
| 1 | Lower Extremity | Vastus Medialis |
| 2 | Upper Extremity | Abductor Pollicis Longus |
| 2 | Upper Extremity | Acromioclavicular Ligaments |
| 2 | Upper Extremity | Adductor Pollicis |
| 2 | Upper Extremity | Anconeus |
| 2 | Upper Extremity | Annular Ligament |
| 2 | Upper Extremity | Biceps Brachii |
| 2 | Upper Extremity | Bicipital Aponeurosis |
| 2 | Upper Extremity | Brachialis |
| 2 | Upper Extremity | Brachioradialis |
| 2 | Upper Extremity | Common Extensor Tendon: Extensor Carpi Radialis Brevis |
| 2 | Upper Extremity | Common Extensor Tendon: Extensor Carpi Ulnaris |
| 2 | Upper Extremity | Common Extensor Tendon: Extensor Digiti Minimi |
| 2 | Upper Extremity | Common Extensor Tendon: Extensor Digitorum Communis |
| 2 | Upper Extremity | Coracoacromial Ligaments |
| 2 | Upper Extremity | Coracobrachialis |
| 2 | Upper Extremity | Deltoid (Anterior and Middle Fibers) |
| 2 | Upper Extremity | Deltoid (Posterior Fibers) |
| 2 | Upper Extremity | Dorsal and Palmar Interossei |
| 2 | Upper Extremity | Dorsal Ligaments (Radioulnar, Radiocarpal, Intercarpal) |
| 2 | Upper Extremity | Extensor Carpi Radialis Longus |
| 2 | Upper Extremity | Extensor Indicis |
| 2 | Upper Extremity | Extensor Pollicis Brevis |
| 2 | Upper Extremity | Extensor Pollicis Longus |
| 2 | Upper Extremity | Extensor Retinaculum |
| 2 | Upper Extremity | Extensor Tendons with Expansions |
| 2 | Upper Extremity | Flexor Carpi Radialis |
| 2 | Upper Extremity | Flexor Carpi Ulnaris |
| 2 | Upper Extremity | Flexor Digitorum Profundus |
| 2 | Upper Extremity | Flexor Digitorum Superficialis (2 heads) |
| 2 | Upper Extremity | Flexor Pollicis Longus |
| 2 | Upper Extremity | Flexor Retinaculum/Transverse Carpal Ligament |
| 2 | Upper Extremity | Glenohumeral Joint Capsule |
| 2 | Upper Extremity | Hypothenar Muscles |
| 2 | Upper Extremity | Infraspinatus |
| 2 | Upper Extremity | Interosseus Membrane |
| 2 | Upper Extremity | Joint Capsules |
| 2 | Upper Extremity | Lateral Intermuscular Septum |
| 2 | Upper Extremity | Latissimus Dorsi Insertion (Distal 3rd) |
| 2 | Upper Extremity | Lumbricals (Digits 2 & 3) |
| 2 | Upper Extremity | Lumbricals (Digits 3 & 4) |
| 2 | Upper Extremity | Medial Intermuscular Septum |
| 2 | Upper Extremity | Palmar Fascia |
| 2 | Upper Extremity | Palmar Ligaments (Radioulnar, Radiocarpal, Intercarpal) |
| 2 | Upper Extremity | Palmaris Brevis |
| 2 | Upper Extremity | Palmaris Longus |
| 2 | Upper Extremity | Pectoralis Major |
| 2 | Upper Extremity | Pronator Quadratus |
| 2 | Upper Extremity | Pronator Teres |
| 2 | Upper Extremity | Quadrate Ligament |
| 2 | Upper Extremity | Radial Collateral Ligament of Elbow |
| 2 | Upper Extremity | Radial Collateral Ligament of Wrist |
| 2 | Upper Extremity | Serratus Anterior (Scapular Insertion) |
| 2 | Upper Extremity | Subscapularis |
| 2 | Upper Extremity | Supinator and Arcade of Frohse |
| 2 | Upper Extremity | Supraspinatus |
| 2 | Upper Extremity | Teres Major |
| 2 | Upper Extremity | Teres Minor |

TABLE 1-continued

Structures for TAPN Treatment

| System No. | System | Structure |
|---|---|---|
| 2 | Upper Extremity | Thenar Muscles |
| 2 | Upper Extremity | Triangular Fibrocartilage Disc |
| 2 | Upper Extremity | Triceps Brachii |
| 2 | Upper Extremity | Tunnel of Guyon |
| 2 | Upper Extremity | Ulnar Collateral Ligament (UCL) Of Wrist |
| 3 | Spine and Thorax | Diaphragm |
| 3 | Spine and Thorax | Erector Spinae (Iliocostalis, Longissimus, Spinalis) |
| 3 | Spine and Thorax | External Intercostals |
| 3 | Spine and Thorax | Heart |
| 3 | Spine and Thorax | Internal Intercostals |
| 3 | Spine and Thorax | Interspinales (Cervical, Thoracic, Lumbar) |
| 3 | Spine and Thorax | Intertransversarii (Cervical, Thoracic, Lumbar) |
| 3 | Spine and Thorax | Latissimus Dorsi Origin |
| 3 | Spine and Thorax | Levator Scapula |
| 3 | Spine and Thorax | Levatores Costorum |
| 3 | Spine and Thorax | Lung |
| 3 | Spine and Thorax | Mamillary Tissue |
| 3 | Spine and Thorax | Middle and Lower Fiber Trapezius |
| 3 | Spine and Thorax | Multifidi (Cervical, Thoracic, Lumbar) |
| 3 | Spine and Thorax | Quadratus Lumborum |
| 3 | Spine and Thorax | Rhomboids |
| 3 | Spine and Thorax | Rotatores (Cervical, Thoracic, Lumbar) |
| 3 | Spine and Thorax | Semispinalis (Cervical, Thoracic, Lumbar) |
| 3 | Spine and Thorax | Serratus Anterior (Costal Origin) |
| 3 | Spine and Thorax | Serratus Posterior Inferior |
| 3 | Spine and Thorax | Serratus Posterior Superior |
| 3 | Spine and Thorax | Splenius (Capitus, Cervicis) |
| 3 | Spine and Thorax | Subclavius |
| 3 | Spine and Thorax | Suboccipital: Obliquus Capitis Inferior |
| 3 | Spine and Thorax | Suboccipital: Obliquus Capitis Superior |
| 3 | Spine and Thorax | Suboccipital: Rectus CapitIs Posterior Major |
| 3 | Spine and Thorax | Suboccipital: Rectus Capitis Posterior Minor |
| 3 | Spine and Thorax | Supraspinous/Nuchal Ligament |
| 3 | Spine and Thorax | Supraspinous Ligament (Thoracic, Lumbar) |
| 3 | Spine and Thorax | Thoracolumbar Fascia |
| 3 | Spine and Thorax | Upper Fiber Trapezius |
| 4 | Cranium, Face and Anterior Neck | Anterior Auricular |
| 4 | Cranium, Face and Anterior Neck | Anterior Scalene |
| 4 | Cranium, Face and Anterior Neck | Aryepiglottic |
| 4 | Cranium, Face and Anterior Neck | Brain |
| 4 | Cranium, Face and Anterior Neck | Buccinator |
| 4 | Cranium, Face and Anterior Neck | Ciliary Muscle |
| 4 | Cranium, Face and Anterior Neck | Coronalis |
| 4 | Cranium, Face and Anterior Neck | Corrugator Supercilii |
| 4 | Cranium, Face and Anterior Neck | Cricothyroid |
| 4 | Cranium, Face and Anterior Neck | Depressor Anguli Oris |
| 4 | Cranium, Face and Anterior Neck | Depressor Labii Inferioris |
| 4 | Cranium, Face and Anterior Neck | Digastric |
| 4 | Cranium, Face and Anterior Neck | Dilator Muscle |
| 4 | Cranium, Face and Anterior Neck | Epicranius |
| 4 | Cranium, Face and Anterior Neck | Frontolacrimalis |
| 4 | Cranium, Face and Anterior Neck | Frontomaxilaris |
| 4 | Cranium, Face and Anterior Neck | Frontonasalis |
| 4 | Cranium, Face and Anterior Neck | Frontozygomatica |
| 4 | Cranium, Face and Anterior Neck | Genioglossus |
| 4 | Cranium, Face and Anterior Neck | Geniohyoid |
| 4 | Cranium, Face and Anterior Neck | Hyoglossus |
| 4 | Cranium, Face and Anterior Neck | Inferior Longitudinal |
| 4 | Cranium, Face and Anterior Neck | Inferior Pharyngeal Constrictor |
| 4 | Cranium, Face and Anterior Neck | Lacrimomaxillaris Suture |
| 4 | Cranium, Face and Anterior Neck | Lambdoid Suture |
| 4 | Cranium, Face and Anterior Neck | Lateral Cricoarytenoid |
| 4 | Cranium, Face and Anterior Neck | Lateral Pterygoid |
| 4 | Cranium, Face and Anterior Neck | Levator Anguli Oris |
| 4 | Cranium, Face and Anterior Neck | Levator Labii Superiores Aleque Nasi |
| 4 | Cranium, Face and Anterior Neck | Levator Labii Superioris |
| 4 | Cranium, Face and Anterior Neck | Levator Palpebrae Superioris |
| 4 | Cranium, Face and Anterior Neck | Levator Veli Palati |
| 4 | Cranium, Face and Anterior Neck | Masseter |
| 4 | Cranium, Face and Anterior Neck | Medial Pterygoid |
| 4 | Cranium, Face and Anterior Neck | Mentalis |
| 4 | Cranium, Face and Anterior Neck | Middle Pharyngeal Constrictor |
| 4 | Cranium, Face and Anterior Neck | Middle Scalene |
| 4 | Cranium, Face and Anterior Neck | Musculus Uvulae |

TABLE 1-continued

Structures for TAPN Treatment

| System No. | System | Structure |
|---|---|---|
| 4 | Cranium, Face and Anterior Neck | Mylohyoid |
| 4 | Cranium, Face and Anterior Neck | Nasalis |
| 4 | Cranium, Face and Anterior Neck | Nasomaxillaris Suture |
| 4 | Cranium, Face and Anterior Neck | Oblique Arytenoid |
| 4 | Cranium, Face and Anterior Neck | Occipitimastoid Suture |
| 4 | Cranium, Face and Anterior Neck | Omohyoid |
| 4 | Cranium, Face and Anterior Neck | Orbicularis Oculi |
| 4 | Cranium, Face and Anterior Neck | Orbicularis Oris |
| 4 | Cranium, Face and Anterior Neck | Palatoglossus |
| 4 | Cranium, Face and Anterior Neck | Palatoglossus |
| 4 | Cranium, Face and Anterior Neck | Palatopharyngeus |
| 4 | Cranium, Face and Anterior Neck | Parathyroid |
| 4 | Cranium, Face and Anterior Neck | Parietomastoid Suture |
| 4 | Cranium, Face and Anterior Neck | Parotid Gland |
| 4 | Cranium, Face and Anterior Neck | Platysma |
| 4 | Cranium, Face and Anterior Neck | porus acusticus externus |
| 4 | Cranium, Face and Anterior Neck | Posterior Auricular |
| 4 | Cranium, Face and Anterior Neck | Posterior Cricoarytenoid |
| 4 | Cranium, Face and Anterior Neck | Posterior Scalene |
| 4 | Cranium, Face and Anterior Neck | Procerus |
| 4 | Cranium, Face and Anterior Neck | Risorius |
| 4 | Cranium, Face and Anterior Neck | Salpingopharyngeus |
| 4 | Cranium, Face and Anterior Neck | Sphenofrontalis Suture |
| 4 | Cranium, Face and Anterior Neck | Sphenosquamosa Suture |
| 4 | Cranium, Face and Anterior Neck | Sphenozygomatic Suture |
| 4 | Cranium, Face and Anterior Neck | Sphincter Pupillae |
| 4 | Cranium, Face and Anterior Neck | Squamomastoid Suture |
| 4 | Cranium, Face and Anterior Neck | Squamous Suture |
| 4 | Cranium, Face and Anterior Neck | Stapedius |
| 4 | Cranium, Face and Anterior Neck | Sternocleidomastoid |
| 4 | Cranium, Face and Anterior Neck | Sternohyoid |
| 4 | Cranium, Face and Anterior Neck | Sternothyroid |
| 4 | Cranium, Face and Anterior Neck | Styloglossus |
| 4 | Cranium, Face and Anterior Neck | Stylohyoid |
| 4 | Cranium, Face and Anterior Neck | Stylopharyngeus |
| 4 | Cranium, Face and Anterior Neck | Superior Auricular |
| 4 | Cranium, Face and Anterior Neck | Superior Longitudinal |
| 4 | Cranium, Face and Anterior Neck | Superior Pharyngeal Constrictor |
| 4 | Cranium, Face and Anterior Neck | Superior Tarsal |
| 4 | Cranium, Face and Anterior Neck | Temporalis |
| 4 | Cranium, Face and Anterior Neck | Temporozygomatic Suture |
| 4 | Cranium, Face and Anterior Neck | Tensor Tympani |
| 4 | Cranium, Face and Anterior Neck | Tensor Veli Palati |
| 4 | Cranium, Face and Anterior Neck | Thyroarytenoid |
| 4 | Cranium, Face and Anterior Neck | Thyroepiglottic |
| 4 | Cranium, Face and Anterior Neck | Thyrohyoid |
| 4 | Cranium, Face and Anterior Neck | Thyroid |
| 4 | Cranium, Face and Anterior Neck | Transverse |
| 4 | Cranium, Face and Anterior Neck | Transverse Arytenoid |
| 4 | Cranium, Face and Anterior Neck | Vertical |
| 4 | Cranium, Face and Anterior Neck | Vocalis |
| 4 | Cranium, Face and Anterior Neck | Zygomaticomaxillaris Suture |
| 4 | Cranium, Face and Anterior Neck | Zygomaticus Major |
| 4 | Cranium, Face and Anterior Neck | Zygomaticus Minor |
| 5 | Pelvic, Abdominal and Visceral | Abdominals: External Obliques |
| 5 | Pelvic, Abdominal and Visceral | Abdominals: Internal Obliques |
| 5 | Pelvic, Abdominal and Visceral | Abdominals: Rectus Abdominus |
| 5 | Pelvic, Abdominal and Visceral | Abdominals: Transversus Abdominus |
| 5 | Pelvic, Abdominal and Visceral | Anterior Sacral Ligaments |
| 5 | Pelvic, Abdominal and Visceral | Appendix |
| 5 | Pelvic, Abdominal and Visceral | Ascending Colon |
| 5 | Pelvic, Abdominal and Visceral | Bladder |
| 5 | Pelvic, Abdominal and Visceral | Bulbospongiosis External |
| 5 | Pelvic, Abdominal and Visceral | Cecum |
| 5 | Pelvic, Abdominal and Visceral | Coccygeal Ligament |
| 5 | Pelvic, Abdominal and Visceral | Cremaster |
| 5 | Pelvic, Abdominal and Visceral | Deep Transverse Perineal |
| 5 | Pelvic, Abdominal and Visceral | Descending Colon |
| 5 | Pelvic, Abdominal and Visceral | Duodenum |
| 5 | Pelvic, Abdominal and Visceral | Esophagus |
| 5 | Pelvic, Abdominal and Visceral | External Urethral Sphinter |
| 5 | Pelvic, Abdominal and Visceral | Gall Bladder |
| 5 | Pelvic, Abdominal and Visceral | Iliocecal Valve |
| 5 | Pelvic, Abdominal and Visceral | Iliococcygeus (Levator Ani) |
| 5 | Pelvic, Abdominal and Visceral | Iliolumbar Ligament |
| 5 | Pelvic, Abdominal and Visceral | Illium |

TABLE 1-continued

Structures for TAPN Treatment

| System No. | System | Structure |
|---|---|---|
| 5 | Pelvic, Abdominal and Visceral | Inguinal Ligament |
| 5 | Pelvic, Abdominal and Visceral | Ischiocavernosis External |
| 5 | Pelvic, Abdominal and Visceral | Ischiococcygeus |
| 5 | Pelvic, Abdominal and Visceral | Jejunum |
| 5 | Pelvic, Abdominal and Visceral | Kidneys |
| 5 | Pelvic, Abdominal and Visceral | Levator Ani External |
| 5 | Pelvic, Abdominal and Visceral | Liver |
| 5 | Pelvic, Abdominal and Visceral | Mesentery |
| 5 | Pelvic, Abdominal and Visceral | Mons Pubis |
| 5 | Pelvic, Abdominal and Visceral | Obturator Internus (Proximal ⅓ Origin) |
| 5 | Pelvic, Abdominal and Visceral | Omentum |
| 5 | Pelvic, Abdominal and Visceral | Ovaries |
| 5 | Pelvic, Abdominal and Visceral | Pancreas |
| 5 | Pelvic, Abdominal and Visceral | Posterior Sacral Ligaments |
| 5 | Pelvic, Abdominal and Visceral | Prostate |
| 5 | Pelvic, Abdominal and Visceral | Proximal Hamstrings Origin |
| 5 | Pelvic, Abdominal and Visceral | Pubococcygeus (Levator Ani) |
| 5 | Pelvic, Abdominal and Visceral | Puborectalis (Levator Ani) |
| 5 | Pelvic, Abdominal and Visceral | Pyrimidalis |
| 5 | Pelvic, Abdominal and Visceral | Rectum |
| 5 | Pelvic, Abdominal and Visceral | Sacrospinous Ligament |
| 5 | Pelvic, Abdominal and Visceral | Sacrotuberous Ligament |
| 5 | Pelvic, Abdominal and Visceral | Sigmoid Colon |
| 5 | Pelvic, Abdominal and Visceral | Sphinter Urethrae |
| 5 | Pelvic, Abdominal and Visceral | Spleen |
| 5 | Pelvic, Abdominal and Visceral | Stomach |
| 5 | Pelvic, Abdominal and Visceral | Superficial Transverse Perineal |
| 5 | Pelvic, Abdominal and Visceral | Transverse Colon |
| 5 | Pelvic, Abdominal and Visceral | Transverse Perineal External |
| 5 | Pelvic, Abdominal and Visceral | Uereters |
| 5 | Pelvic, Abdominal and Visceral | Urethrovaginalis |
| 5 | Pelvic, Abdominal and Visceral | Uterus |

Figure 39:
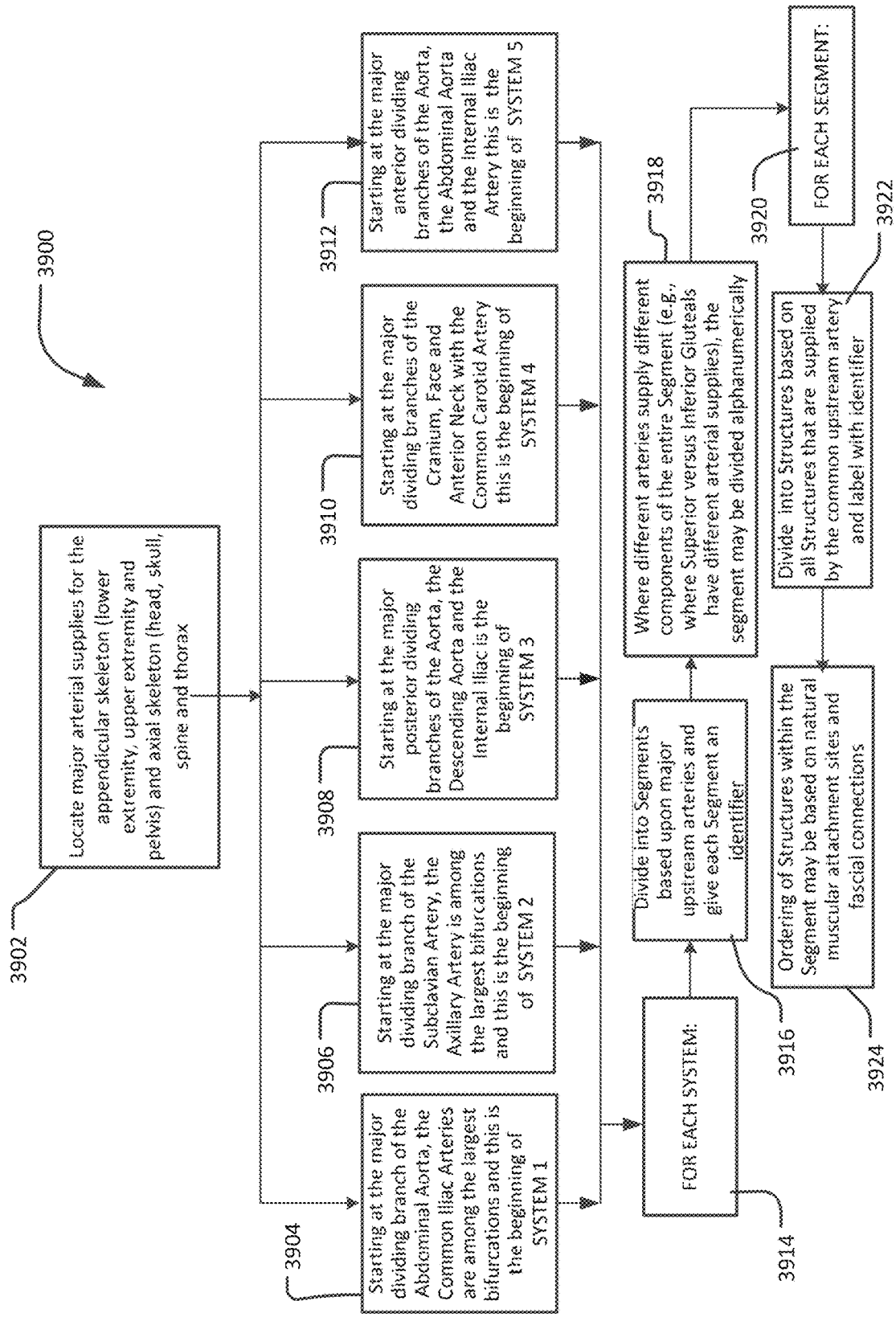
FIG. 39 is a flowchart of logic that may be utilized to develop an expert system of rules for making taxonomical subdivisions of the human body into System: Segment: and Structure.

FIG. 39 shows a logical process 3900 for ascertaining a taxonomical system that classifies the human body into components of System:Segment:Structure. The classification is primarily based upon blood supply to discrete occlusale structures. In this regard, it is possible to locate or divide 3902 the human body into major arterial supplies for the appendicular skeleton including the lower extremity and upper extremity and pelvis; together with the axial skeleton including the head, skull, spine and thorax. These may be classified as: (1) SYSTEM 1 (3904) starting at the major dividing branch of the Abdominal Aorta, the Common Iliac Arteries being the largest bifurcations mark the beginning of SYSTEM 1; SYSTEM 2 (3906) starting at the major dividing branch of the Subclavian Artery, the Axillary Artery being among the largest bifurcations mark the beginning of SYSTEM 2; SYSTEM 3 (3908) starting at the major posterior dividing branches of the Aorta, the Descending Aorta and the Internal Iliac are the beginning of SYSTEM 3; SYSTEM 4 (3910) starting at the major dividing branches of the Cranium, Face and Anterior Neck the Common Carotid Artery marks the beginning of SYSTEM 4; and SYSTEM 5 (3912) starting at the major anterior dividing branches of the Aorta, the Abdominal Aorta and the Internal Iliac Artery this is the beginning of SYSTEM 5.

Then in the next stage 3914 of classification, each System is subdivided 3916 into Segments based upon major upstream arteries. The Segments that are identified in this manner are given an identifier as part of the system of taxonomy. In some cases there will be more than one major arteries that feed blood to a discrete Segment. In this instance 3918, the Segment may be divided into subclasses by use of an additional identifier, such as a numeric identifier followed by an alphanumeric component indicating a Segment having a plurality of arterial blood supplies. By way of example, Superior versus Inferior Gluteals have different arterial supplies.

Once the Segments are located in the manner described above, the next phase 3920 includes subdividing 3922 each Segment into Structures. This subclassification may proceed by identifying discrete occlusale Structures on branches that are supplied by the common upstream artery for each Segment. Each Structure that is identified in this manner may be labeled with an identifier for use in the system of taxonomy. The Structures for each Segment may be ordered 3924 be based upon natural muscular attachment sites and fascial connections for the Structures.

Figure 40:
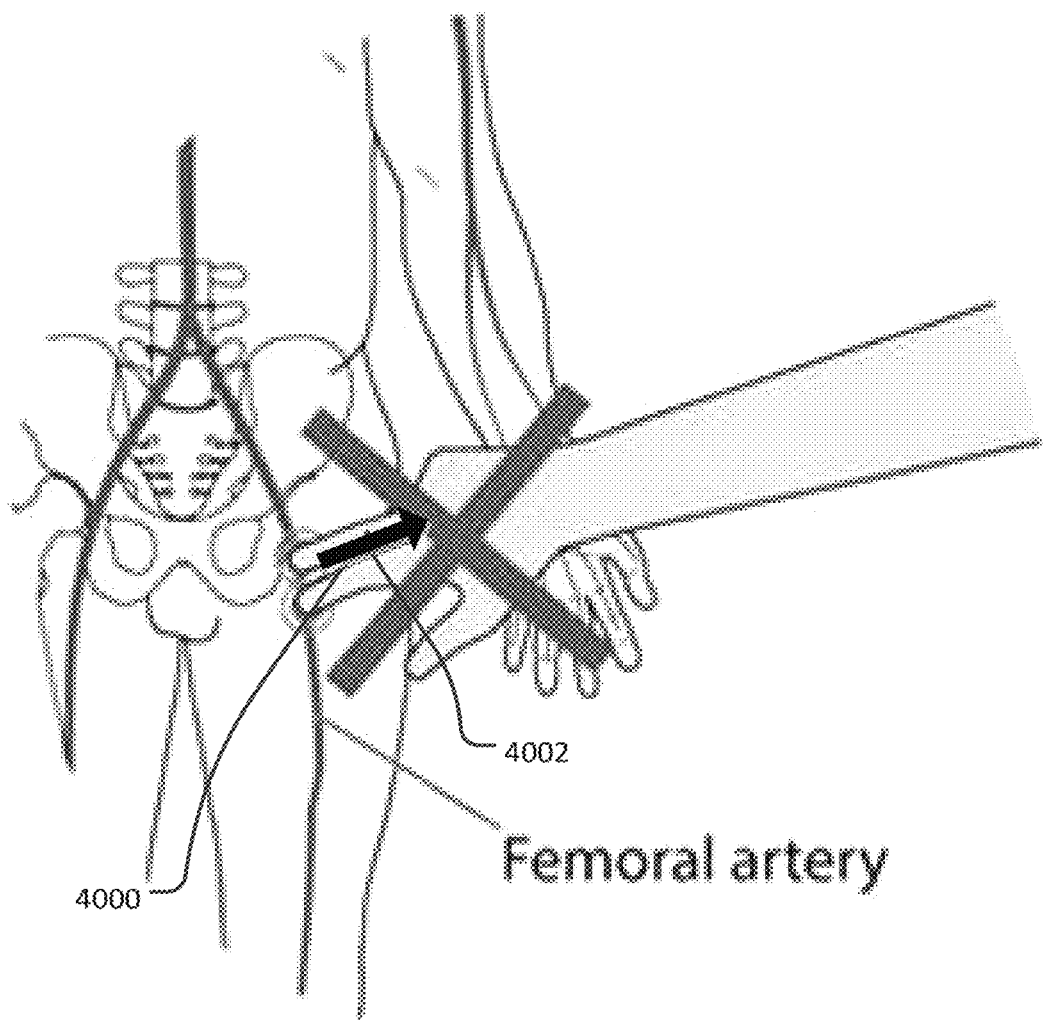
FIG. 40 provides guidance demonstrating a preferred technique for practicing occlusion by compression and glide.

FIG. 40 demonstrates preferred aspects of the compression plus guide technique. As show in this example, a practitioner's fingers are positioned at a hand placement point (HP1) 4000. The technique is being incorrectly performed because the fingers are placed directly on the femoral artery. Hand placement of activation points are always placed adjacent to the artery using the suggested vector to create the manual tourniquet by use of tension at 90 degrees. A more preferred hand placement would be off of the femoral artery with occlusion being enhanced by a glide along vector 4002 at an angle of approximately 90° to the axis of elongation in the femoral artery at the activation point.

Those skilled in the art will appreciate that the embodiments shown and described may be subjected to insubstantial changes without departing from the true scope and spirit of what is claimed as the invention. The inventor, accordingly, states her intentions to rely upon the Doctrine of Equivalents as needed in protecting her rights to the invention.

REFERENCES

The following references provide additional information on reperfusion injuries and the treatment thereof, and are hereby incorporated by reference to the same extent as though fully replicated herein.

Anderson, J. E. (2000). A Role for Nitric Oxide in Muscle Repair: Nitric Oxide-mediated Activation of Muscle Satellite Cells. Molecular Biology of the Cell, 11(5), 1859-1874.

Anrather, J., & Hallenbeck, J. M. (2013). Biological Networks in Ischemic Tolerance—Rethinking the Approach to Clinical Conditioning. Transl. Stroke Res. Translational Stroke Research, 4(1), 114-129.

Bestwick, C. S., Maffuli, N. (2004). Reactive oxygen species and tendinopathy: Do they matter? British Journal of Sports Medicine, 38(6), 672-674.

Blake, D., Unsworth, J., Outhwaite, J., Morris, C., Merry, P., Kidd, B., Lunec, J. (1989). Hypoxic-Reperfusion Injury In The Inflamed Human Joint. The Lancet, 333(8633), 289-293.

Breig, A., & Troup, J. D. (1979). Biomechanical Considerations in the Straight-Leg-Raising Test Cadaveric and Clinical Studies of the Effects of Medial Hip Rotation. Spine, 4(3), 242-570.

Butler, D., & Gifford, L. (1989). The Concept of Adverse Mechanical Tension in the Nervous System. Physiotherapy, 75(11), 622-636.

Butler, D. S. (1991). Mobilisation of the nervous system. London: Churchill Livingstone.

Burda, J., Danielisová, V., Némethová, M., Gottlieb, M., Matiašová, M., Domoráková, I., Burda, R. (2006). Delayed Postconditioning Initiates Additive Mechanism Necessary for Survival of Selectively Vulnerable Neurons After Transient Ischemia in Rat Brain. Cellular and Molecular Neurobiology Cell Mol Neurobiol, 26(7-8), 1139-1149.

Cherry-Allen, K. M., Gidday, J. M., Lee, J., Hershey, T., & Lang, C. E. (2015). Remote limb ischemic conditioning enhances motor learning in healthy humans. Journal of Neurophysiology J Neurophysiol, 113(10), 3708-3719.

Cyriax, J. (1942). Perineuritis. British Medical Journal, 1(4244), 578-580.

Elvey, R. (1980). Brachial plexus tension tests for the pathoanatomical origin of arm pain (R. Idczak, Ed.). Aspects of Manipulative Therapy, Lincoln Institute of Health Sciences.

Elvey, R. (1986). Treatment of Arm Pain Associated with Abnormal Brachial Plexus Tension. Australian Journal of Physiotherapy, 32(4), 225-230.

Fahrni, W. (1966). Observations on straight-leg-raising with special reference to nerve root adhesions. Canadian Journal of Surgery, 9(1), 44-48.

Farrell, A. J., Williams, R. B., Stevens, C. R., Lawrie, A. S., Cox, N. L., & Blake, D. R. (1992). Exercise induced release of von Willebrand factor: Evidence for hypoxic reperfusion microvascular injury in rheumatoid arthritis. Annals of the Rheumatic Diseases, 51(10), 1117-1122.

Findlay, D. M. (2007). Vascular pathology and osteoarthritis. Rheumatology, 46(12), 1763-1768.

Flaws, B. (2012). The secret of Chinese pulse diagnosis. Boulder, Colo.: Blue Poppy Press.

Frykholm, R. (1951). The mechanism of cervical radicular lesions resulting from friction or forceful traction. Acta Chirurgia Scandinavica, 102(2), 93-98.

Gillani, S., Cao, J., Suzuki, T., & Hak, D. J. (2012). The effect of ischemia reperfusion injury on skeletal muscle. Injury, 43(6), 670-675.

Gray, H., Lewis, W. H. (1918). Anatomy of the Human Body (20th ed.). Philadelphia: Lea & Febiger.

Hahn, C. D., Manlhiot, C., Schmidt, M. R., Nielsen, T. T., & Redington, A. N. (2011). Remote Ischemic Per-Conditioning: A Novel Therapy for Acute Stroke? Stroke, 42(10), 2960-2962.

Hausenloy, D. J., & Yellon, D. M. (2008). Remote ischaemic preconditioning: Underlying mechanisms and clinical application. Cardiovascular Research, 79(3), 377-386.

Heusch, G., Botker, H. E., Przyklenk, K., Redington, A., & Yellon, D. (2015). Remote ischemic conditioning. Journal of the American College of Cardiology, 65(2), 177-195.

Kalogeris, T., Baines, C. P., Krenz, M., & Korthuis, R. J. (2012). Cell Biology of Ischemia/Reperfusion Injury. International Review of Cell and Molecular Biology, 298, 229-317.

Kendall, A. C., Whatmore, J. L., Winyard, P. G., Smerdon, G. R., & Eggleton, P. (2013). Hyperbaric oxygen treatment reduces neutrophil-endothelial adhesion in chronic wound conditions through S-nitrosation. Wound Repair and Regeneration Wound Repair Regen, 21(6), 860-868.

Kenneally, M., Rubenach, H., & Elvey, R. (1988). The upper limb tension test: The SLR test of the arm (R. Grant, Ed.). Clinics in Physical Therapy, Physical Therapy of the Cervical and Thoracic Spine, 17, 167-194.

Knight, K. L. (1995). Cryotherapy in sports injury management. Champaign, IL: Human Kinetics.

Kocman, E. A., Ozatik, O., Sahin, A., Guney, T., Kose, A. A., Dag, I., et al. (2015). Effects of ischemic preconditioning protocols on skeletal muscle ischemia-reperfusion injury. *Journal of Surgical Research*, 193(2), 942-952.

Koning, M. M., Simonis, L. A., Zeeuw, S. D., Nieukoop, S., Post, S., & Verdouw, P. D. (1994). Ischaemic preconditioning by partial occlusion without intermittent reperfusion. Cardiovascular Research, 28(8), 1146-1151.

Koning, M. M., Gho, B. C., Klaarwater, E. V., Duncker, D. J., & Verdouw, P. D. (1995). Endocardial and epicardial infarct size after preconditioning by a partial coronary artery occlusion without intervening reperfusion. Importance of the degree and duration of flow reduction. Cardiovascular Research, 30(6), 1017-1027.

Konstantinov, I. E., Arab, S., Kharbanda, R. K., Li, J., Cheung, M. M., Cherepanov, V., Redington, A. N. (2004). The remote ischemic preconditioning stimulus modifies inflammatory gene expression in humans. Physiol. Genomics Physiological Genomics, 19(1), 143-150.

Leconte, C., Tixier, E., Freret, T., Toutain, J., Saulnier, R., Boulouard, M., Bernaudin, M. (2009). Delayed Hypoxic Postconditioning Protects Against Cerebral Ischemia in the Mouse. Stroke, 40(10), 3349-3355.

Lee, H., Schroeder, J. C., Shah, P., Babu, S., Thompson, C., & Belloni, F. (1996). Preconditioning with Ischemia or Adenosine Protects Skeletal Muscle from Ischemic Tissue Reperfusion Injury. *Journal of Surgical Research*, 63(1), 29-34.

Lim, S. Y., & Hausenloy, D. J. (2012). Remote Ischemic Conditioning: From Bench to Bedside. Frontiers in Physiology Front. Physio., 3.

Lundborg, G., & Rydevik, B. (1973). Effects of stretching the tibial nerve of the rabbit. Journal of Bone and Joint Surgery, 55(2), 390-401.

Maitland, G. D. (1986). Vertebral Manipulation (5th ed.). Place of publication not identified: Butterworth.

Marx, H. T., & Yu, P. N. (1967). Clinical examination of the arterial pulse. Progress in Cardiovascular Diseases, 10(3), 207-235.

Merrick, M. A. (2002). Secondary Injury After Musculoskeletal Trauma: A Review and Update. Journal of Athletic Training, 37(2), 209-217.

Murry, C. E., Jennings, R. B., & Reimer, K. A. (1986). Preconditioning with ischemia: A delay of lethal cell injury in ischemic myocardium. Circulation, 74(5), 1124-1136.

Myers, T. W. (2009). Anatomy Trains: Myofascial meridians for manual and movement therapists (2nd ed.). Edinburgh: Churchill Livingstone.

O'connell, J. (1946). The Clinical Signs Of Meningeal Irritation. Brain, 69(1), 9-21.

Ogata, K., & Naito, M. (1986). Blood flow of peripheral nerve effects of dissection stretching and compression. The Journal of Hand Surgery: Journal of the British Society for Surgery of the Hand, 11(1), 10-14.

O'rourke, M. F., & Avolio, A. P. (1980). Pulsatile flow and pressure in human systemic arteries. Studies in man and in a multibranched model of the human systemic arterial tree. Circulation Research, 46(3), 363-372.

Opie, L. H., & Lecour, S. (2011). Delayed Postconditioning: Cardioprotection at the Limit? Circulation, 124(12), 1315-1318.

Ovize, M., Przyklenk, K., & Kloner, R. A. (1992). Partial coronary stenosis is sufficient and complete reperfusion is mandatory for preconditioning the canine heart. Circulation Research, 71(5), 1165-1173.

Pope, Z. K., Willardson, J. M., & Schoenfeld, B. J. (2013). G-27 Thematic Poster—Exercise and Blood Flow Restriction. Medicine & Science in Sports & Exercise, 27(10), 2914-2926.

Przyklenk, K., Bauer, B., Ovize, M., Kloner, R. A., & Whittaker, P. (1993). Regional ischemic 'preconditioning' protects remote virgin myocardium from subsequent sustained coronary occlusion. Circulation, 87(3), 893-899.

Reid, J. (1960). Effects Of Flexion-Extension Movements Of The Head And Spine Upon The Spinal Cord And Nerve Roots. Journal of Neurology, Neurosurgery & Psychiatry, 23(3), 214-221.

Rein, S., Hanisch, U., Zwipp, H., Fieguth, A., Lwowski, S., & Hagert, E. (2013). Comparative Analysis of Inter- and Intraligamentous Distribution of Sensory Nerve Endings in Ankle Ligaments: A Cadaver Study. Foot & Ankle International, 34(7), 1017-1024.

Ren, C., Yan, Z., Wei, D., Gao, X., Chen, X., & Zhao, H. (2009). Limb remote ischemic postcondition in protects against focal ischemia in rats. Brain Research, 1288, 88-94.

Ren, C., Gao, X., Steinberg, G., & Zhao, H. (2008). Limb remote-preconditioning protects against focal ischemia in rats and contradicts the dogma of therapeutic time windows for preconditioning. Neuroscience, 151(4), 1099-1103.

Sanada, S., Komuro, I., & Kitakaze, M. (2011). Pathophysiology of myocardial reperfusion injury: Preconditioning, postconditioning, and translational aspects of protective measures. AJP: Heart and Circulatory Physiology, 301(5).

Saxena, P., Newman, M. A., Shehatha, J. S., Redington, A. N., & Konstantinov, I. E. (2010). Remote Ischemic Conditioning: Evolution of the Concept, Mechanisms, and Clinical Application. Journal of Cardiac Surgery, 25(1), 127-134.

Schmidt, M. R., Smerup, M., Konstantinov, I. E., Shimizu, M., Li, J., Cheung, M., Kharbanda, R. K. (2006). Intermittent peripheral tissue ischemia during coronary ischemia reduces myocardial infarction through a KATP-dependent mechanism: First demonstration of remote ischemic perconditioning. AJP: Heart and Circulatory Physiology, 292(4).

Schoen, M., Rotter, R., Gierer, P., Gradl, G., Strauss, U., Jonas, L., Vollmar, B. (2007). Ischemic Preconditioning Prevents Skeletal Muscle Tissue Injury, But Not Nerve Lesion Upon Tourniquet-Induced Ischemia. The Journal of Trauma: Injury, Infection, and Critical Care, 63(4), 788-797.

Shacklock, M., Butler, D., & Slater, H. (1994). The dynamic central nervous system: Structure and clinical neurobiomechanics. In J. Boyling & N. Palastanga (Eds.), Grieve's modern Manual Therapy of the Vertebral Column, 2, pp. 21-38.

Shimizu, M., Tropak, M., Diaz, R., Suto, F., Surendra, H., Kuzmin, E., Redington, A. (2009). Transient limb ischaemia remotely preconditions through a humoral mechanism acting directly on the myocardium: Evidence suggesting cross-species protection. Clin. Sci. Clinical Science, 117(5), 191-200.

Shimizu, M., Saxena, P., Konstantinov, I. E., Cherepanov, V., Cheung, M. M., Wearden, P., Redington, A. N. (2010). Remote Ischemic Preconditioning Decreases Adhesion and Selectively Modifies Functional Responses of Human Neutrophils. Journal of Surgical Research, 158(1), 155-161.

Staat, P., Rioufol, G., Piot, C., Coffin, Y., Crung, T. T., L'Huillier, I., Ovize, M. (2005). Postconditioning the Human Heart. Circulation, 112(14), 2143-2148.

Sun, J., Tong, L., Luan, Q., Deng, J., Li, Y., Li, Z., Xiong, L. (2012). Protective effect of delayed remote limb ischemic postconditioning: Role of mitochondrial KATP channels in a rat model of focal cerebral ischemic reperfusion injury, Journal of Cerebral Blood Flow & Metabolism J Cereb Blood Flow Metab, 32(5), 851-859.

Turóczi, Z., Fülöp, A., Lukáts, Á, Garbaisz, D., Lotz, G., Harsányi, L., & Szijártó, A. (2014, May 15). Postconditioning Protects Skeletal Muscle Against a Long-Lasting Vascular Occlusion. Journal of Investigative Surgery, 27(5), 282-290.

Toumi, H. (2003). The inflammatory response: Friend or enemy for muscle injury? British Journal of Sports Medicine, 37(4), 284-286.

Vleeming, A., Stoeckart, R., Volkers, A. C., & Snijders, C. J. (1990). Relation Between Form and Function in the Sacroiliac Joint, Part 1: Clinical anatomical aspects. Spine, 15(2).

Vleeming, A., Volkers, A. C., Snijders, C. J., & Stoeckart, R. (1990). Relation Between Form and Function in the Sacroiliac Joint, Part 2: Biomechanical aspects. Spine, 15(2), 133-136.

Wei, M., Xin, P., Li, S., Tao, J., Li, Y., Li, J., Redington, A. N. (2011). Repeated Remote Ischemic Postconditioning Protects Against Adverse Left Ventricular Remodeling and Improves Survival in a Rat Model of Myocardial Infarction. Circulation Research, 108(10), 1220-1225.

Woodruff, T., Blake, D. R., Freeman, J., Andrews, F. J., Salt, P., & Lunec, J. (1986). Is chronic synovitis an example of reperfusion injury? Annals of the Rheumatic Diseases, 45(7), 608-611.

Zhao, H., Ren, C., Chen, X., & Shen, J. (2012). From Rapid to Delayed and Remote Postconditioning: The Evolving Concept of Ischemic Postconditioning in Brain Ischemia. Current Drug Targets CDT, 13(2), 173-187.

Zhao, H. (2011). The Protective Effects of Ischemic Postconditioning against Stroke: From Rapid to Delayed and Remote Postconditioning. The Open Drug Discovery Journal, 5,138-147.

Zhao, H., Sapolsky, R. M., & Steinberg, G. K. (2006). Interrupting reperfusion as a stroke therapy: Ischemic postconditioning reduces infarct size after focal ischemia in rats. Journal of Cerebral Blood Flow & Metabolism J Cereb Blood Flow Metab, 1114-1121.

Zhao, Z., Corvera, J. S., Halkos, M. E., Kerendi, F., Wang, N., Guyton, R. A., & Vinten-Johansen, J. (2003). Inhibition of myocardial injury by ischemic postconditioning during reperfusion: Comparison with ischemic preconditioning. Am J Physiol Heart Circ Physiol American Journal of Physiology—Heart and Circulatory Physiology, 285(2).

What is claimed is:

1. A system for use in guiding practitioners in prevention and treatment of patients afflicted by musculoskeletal soft tissue injuries from reperfusion injury, comprising:
   a database that contains
      images of taxonomically classified hand placement for treatment of reperfusion injury at one or more Structures of interest in a human body;
      descriptive information associated with the hand placement as shown in the images as part of a framework of data demonstrating how to
         activate treatment by creating a semi-occlusive manual tourniquet at an artery that supplies blood to the one or more Structures of interest;
         stretch a portion of the human body to occlude blood flow to a nerve segment of the human body by elongation of the nerve segment proximate the one or more Structures of interest; and
      a system of expert rules that facilitate selection of the taxonomically classified images and the descriptive information;
   a processor equipped with program logic for a query engine utilizing user input to access the system of expert rules as an aid used in reporting to select and organize of the images and the descriptive information as a report that demonstrates a modality of treating reperfusion injury at a particular Structure of interest; and
   a graphical user interface configured to present the report for use in performing the modality of treatment.

2. The system of claim 1, wherein the framework data further demonstrates how to
   touch the one or more Structures of interest to there attract blood flow; and
   ascertain effectiveness of the semi-occlusive manual tourniquet by determining a shift in volume and/or rate of a pulse at the hand placement.

3. The system of claim 1, wherein the images of the report show the stretch component of the treatment being performed sequentially after activation of the treatment.

4. The system of claim 1, wherein the images of the report show the stretch component of the treatment being simultaneously in a combined approach that conducts the stretch at the same time as activation of the treatment.

5. The system of claim 4, wherein the images show the stretch occurring centrally to further elongate the nerve by motion that is not occurring proximate the hand placement.

6. The system of claim 1, wherein the images show the stretch occurring locally to stretch the nerve locally by movement of the nerve as elongated by movement of the body under the hand placement.

7. The system of claim 1 wherein the images are taxonomically classified by use of a three element code corresponding to Systems as divisions of the human body, Segments as divisions of a particular System, and Structures forming the Structures of interest in the human body.

8. The system of claim 1 wherein the descriptive information origins, insertions, blood supply and innervation in order to facilitate proper hand placement.

9. The system of claim 1, wherein the hand placement is a single activation utilizing one hand for activation.

10. The system of claim 1, wherein the hand placement is a double activation utilizing two hands for activation.

11. The system of claim 1 wherein the hand placement is for a modality of treating a groin pull.

12. The system of claim 1 wherein the hand placement is for a modality of treating pectoral strain.

13. The system of claim 1 wherein the hand placement is for a modality of treating a lower back pain.

14. The system of claim 1 wherein the hand placement is for a modality of treating neck pain.

15. The system of claim 1 wherein the hand placement is for a modality of treating asacral sprain.

16. The system of claim 1 wherein the images include a combination of hand placements shown on medical illustrations and photographs demonstrating the modality in application.

17. The system of claim 1 where the program logic is user-selectively configurable for operation in a state selected from the group consisting of treating patients and training practitioners.

18. The system of claim 1 wherein the program logic includes a module for subscription access management.

19. The system of claim 1 wherein the program logic includes a module for patient monitoring across multiple therapy sessions to provide patient monitoring data.

20. The system of claim 1 wherein the system of expert rules accesses the patient monitoring data to assist selection of a treatment modality in a follow-on treatment session.

21. The system of claim 1, wherein the particular Structure of interest includes at least one Structure selected from the group consisting of: Abductor Digiti Minimi (Layer 1), Abductor Hallucis (Layer 1), Adductor Brevis, Adductor Hallucis (Layer 3), Adductor Longus, Adductor Magnus, Anterior Cruciate Ligament, Articularis Genu, Biceps Femoris(Long Head), Biceps Femoris (Long Head), Biceps Femoris(Short Head), Dorsal Interossei, Extensor Digitorum Brevis & Extensor Hallucis Brevis, Extensor Digitorum Longus, Extensor Hallucis Longus, Flexor Digiti Minimi & Opponens Digiti Minimi (Layer 3), Flexor Digitorum Brevis (Layer 1), Flexor Digitorum Longus, Flexor Hallucis Brevis (Layer3), Flexor Hallucis Longus, Flexor Retinaculum, Gastrocnemius & Achilles Tendon, Gluteus Maximus, Gluteus Medius, Gluteus Minimus, Gracilis, Iliacus, Iliotibial Band, Inferior Extensor Retinaculum, Inferior Gemelli, Interosseus Membrane of Leg, Joint Capsules, Lateral Collateral Ligament of Ankle, Lateral Collateral Ligament of Knee, Lateral Meniscus, Lumbricals (Layer 2), Medial Collateral Ligament of Knee, Medial Collateral Ligaments of Ankle (Deltoid Ligament), Medial Meniscus, Obturator Externus, Obturator Internus Distal ⅔ (Insertion)m Patellar Ligament, Pectineus, Peroneus Brevis, Peroneus Longus, Peroneus Tertius, Piriformis, Plantar Calcaneonavicular Ligament (Spring Ligament), Plantar Fascia, Plantar Interossei (Layer 4), Plantaris, Plica, Popliteus, Posterior Cruciate Ligament, Psoas Major, Psoas Minor, Quadratus Femoris, Quadratus Plantae (Layer 2), Rectus Femoris, Sartorius, Semimembranosus, Semimembranosus, Semitendinosus, Semitendinosus, Soleus & Achilles Tendon, Superior Extensor Retinaculum, Superior Gemelli, Tensor Fascia Lata, Tibialis Anterior, Tibialis Posterior, Transverse Intermuscular Septum, Vastus Intermedius, Vastus Lateralis, and Vastus Medialis.

22. The system of claim 1, wherein the particular Structure of interest includes at least one Structure selected from the group consisting of: Common Extensor Tendon: Extensor Carpi Ulnaris, Abductor Pollicis Longus, Acromioclavicular Ligaments, Adductor Pollicis, Anconeus, Annular Ligament, Biceps Brachii, Bicipital Aponeurosis, Brachialis, Brachioradialis, Common Extensor Tendon: Extensor Carpi Radialis Brevis, Common Extensor Tendon: Extensor Carpi Ulnaris, Common Extensor Tendon: Extensor Digiti Minimi, Common Extensor Tendon: Extensor Digitorum Communis, Coracoacromial Ligaments, Coracobrachialis, Deltoid (Anterior and Middle Fibers), Deltoid (Posterior Fibers), Dorsal and Palmar Interossei, Dorsal Ligaments (Radioulnar, Radiocarpal, Intercarpal), Extensor Carpi Radialis Longus, Extensor Indicis, Extensor Pollicis Brevis, Extensor Pollicis Longus, Extensor Retinaculum, Extensor Tendons with Expansions, Flexor Carpi Radialis, Flexor Carpi Ulnaris, Flexor Digitorum Profundus, Flexor Digitorum Superficialis (2 heads), Flexor Pollicis Longus, Flexor Retinaculum/Transverse Carpal Ligament, Glenohumeral Joint Capsule, Hypothenar Muscles, Infraspinatus, Interosseus Membrane, Joint Capsules, Lateral Intermuscular Septum, Latissimus Dorsi Insertion (Distal 3rd), Lumbricals (Digits 2 & 3). Lumbricals (Digits 3 & 4), Medial Intermuscular Septum, Palmar Fascia, Palmar Ligaments (Radioulnar, Radiocarpal, Intercarpal), Palmaris Brevis, Palmaris Longus, Pectoralis Major, Pronator Quadratus, Pronator Teres, Quadrate Ligament, Radial Collateral Ligament of Elbow, Radial Collateral Ligament of Wrist, Serratus Anterior (Scapular Insertion), Subscapularis, Supinator and Arcade of Frohse, Supraspinatus, Teres Major, Teres Minor, Thenar Muscles, Triangular Fibrocartilage Disc, Triceps Brachii, Tunnel of Guyon, and Ulnar Collateral Ligament (UCL) Of Wrist.

23. The system of claim 1, wherein the particular Structure of interest includes at least one Structure selected from the group consisting of: Diaphragm, Erector Spinae (Iliocostalis, Longissimus, Spinalis), External Intercostals, Heart, Internal Intercostals, Interspinales (Cervical, Thoracic, Lumbar), Intertransversarii (Cervical, Thoracic, Lumbar), Latissimus Dorsi Origin, Levator Scapula, Levatores Costorum, Lung, Mamillary Tissue, Middle and Lower Fiber Trapezius, Multifidi (Cervical, Thoracic, Lumbar), Quadratus Lumborum, Rhomboids, Rotatores (Cervical, Thoracic, Lumbar), Semispinalis (Cervical, Thoracic, Lumbar), Serratus Anterior (Costal Origin), Serratus Posterior Inferior, Serratus Posterior Superior, Splenius (Capitus, Cervicis), Subclavius, Suboccipital: Obliquus Capitis Inferior, Suboccipital: Obliquus Capitis Superior, Suboccipital: Rectus Capitls Posterior Major, Suboccipital: Rectus Capitis Posterior Minor, Supraspinous/Nuchal Ligament, Supraspinous Ligament (Thoracic, Lumbar), Thoracolumbar Fascia, and Upper Fiber Trapezius.

24. The system of claim 1, wherein the particular Structure of interest includes at least one Structure selected from the group consisting of: Anterior Auricular, Anterior Scalene, Aryepiglottic, Brain, Buccinator, Ciliary Muscle, Coronalis, Corrugator Supercilii, Cricothyroid, Depressor Anguli Oris, Depressor Labii Inferioris, Digastric, Dilator Muscle, Epicranius, Frontolacrimalis, Frontomaxilaris, Frontonasalis, Frontozygomatica, Genioglossus, Geniohyoid, Hyoglossus, Inferior Longitudinal, Inferior Pharyngeal Constrictor, Lacrimomaxillaris Suture, Lambdoid Suture, Lateral Cricoarytenoid, Lateral Pterygoid, Levator Anguli Oris, Levator Labii Superiores Aleque Nasi, Levator Labii Superioris, Levator Palpebrae Superioris, Levator Veli Palati, Masseter, Medial Pterygoid, Mentalis, Middle Pharyngeal Constrictor, Middle Scalene, Musculus Uvulae, Mylohyoid, Nasalis, Nasomaxillaris Suture, Oblique Arytenoid, Occipitimastoid Suture, Omohyoid, Orbicularis Oculi, Orbicularis Oris, Palatoglossus, Palatoglossus, Palatopharyngeus, Parathyroid, Parietomastoid Suture, Parotid Gland, Platysma, porus acusticus externus, Posterior Auricular, Posterior Cricoarytenoid, Posterior Scalene, Procerus, Risorius, Salpingopharyngeus, Sphenofrontalis Suture, Sphenosquamosa Suture, Sphenozygomatic Suture, Sphincter Pupillae, Squamomastoid Suture, Squamous Suture, Stapedius, Sternocleidomastoid, Sternohyoid, Sternothyroid, Styloglossus, Stylohyoid, Stylopharyngeus, Superior Auricular, Superior Longitudinal, Superior Pharyngeal Constrictor, Superior Tarsal, Temporalis, Temporozygomatic Suture, Tensor Tympani, Tensor Veli Palati, Thyroarytenoid, Thyroepiglottic, Thyrohyoid, Thyroid, Transverse, Transverse Arytenoid, Vertical, Vocalis, Zygomaticomaxillaris Suture, Zygomaticus Major, and Zygomaticus Minor.

25. The system of claim 1, wherein the particular Structure of interest includes at least one Structure selected from the group consisting of: Abdominals: External Obliques, Abdominals: Internal Obliques, Abdominals: Rectus Abdominus, Abdominals: Transversus Abdominus, Anterior Sacral Ligaments, Appendix, Ascending Colon, Bladder, Bulbospongiosis External, Cecum, Coccygeal Ligament, Cremaster, Deep Transverse Perineal, Descending Colon, Duodenum, Esophagus, External Urethral Sphincter, Gall Bladder, Iliocecal Valve, Iliococcygeus (Levator Ani), Iliolumbar Ligament, Illium, Inguinal Ligament, Ischiocavernosis External, Ischiococcygeus, Jejunum, Kidneys, Levator Ani External, Liver, Mesentery, Mons Pubis, Obturator Internus (Proximal ⅓ Origin), Omentum, Ovaries, Pancreas, Posterior Sacral Ligaments, Prostate, Proximal Hamstrings Origin, Pubococcygeus (Levator Ani), Puborectalis (Levator Ani), Pyrimidalis, Rectum, Sacrospinous Ligament, Sacrotuberous Ligament, Sigmoid Colon, Sphinter Urethrae, Spleen, Stomach, Superficial Transverse Perineal, Transverse Colon, Transverse Perineal External, Uereters, Urethrovaginalis, and Uterus.

26. A method of treating a human body, the method including steps of
consulting a report created by the system of claim 1 for guidance and, as guided by the report:
touching the particular Structure of interest in the human body to there attract blood flow;
activating treatment by creating a semi-occlusive manual tourniquet at an artery that supplies blood to the particular Structure of interest;
ascertaining effectiveness of the semi-occlusive manual tourniquet by determining a shift in volume and/or rate of a pulse at the hand placement; and
stretching a portion of the human body to occlude blood flow to a nerve segment of the human body by elongation of the nerve segment proximate the particular Structure of interest.

27. The method of claim 26, wherein the Structure of interest includes at least one Structure selected from the group consisting of: Abductor Digiti Minimi (Layer 1), Abductor Hallucis (Layer 1), Adductor Brevis, Adductor Hallucis (Layer 3), Adductor Longus, Adductor Magnus, Anterior Cruciate Ligament, Articularis Genu, Biceps Femoris(Long Head), Biceps Femoris (Long Head), Biceps Femoris(Short Head), Dorsal Interossei, Extensor Digitorum Brevis & Extensor Hallucis Brevis, Extensor Digitorum Longus, Extensor Hallucis Longus, Flexor Digiti Minimi & Opponens Digiti Minimi (Layer 3), Flexor Digitorum Brevis (Layer 1), Flexor Digitorum Longus, Flexor Hallucis Brevis (Layer3), Flexor Hallucis Longus, Flexor Retinaculum, Gastrocnemius & Achilles Tendon, Gluteus Maximus, Gluteus Medius, Gluteus Minimus, Gracilis, Iliacus, Iliotibial Band, Inferior Extensor Retinaculum, Inferior Gemelli, Interosseus Membrane of Leg, Joint Capsules, Lateral Collateral Ligament of Ankle, Lateral Collateral Ligament of Knee, Lateral Meniscus, Lumbricals (Layer 2), Medial Collateral Ligament of Knee, Medial Collateral Ligaments of Ankle (Deltoid Ligament), Medial Meniscus, Obturator Externus, Obturator Internus Distal ⅔ (Insertion)m Patellar Ligament, Pectineus, Peroneus Brevis, Peroneus Longus, Peroneus Tertius, Piriformis, Plantar Calcaneonavicular Ligament (Spring Ligament), Plantar Fascia, Plantar Interossei (Layer 4), Plantaris, Plica, Popliteus, Posterior Cruciate Ligament, Psoas Major, Psoas Minor, Quadratus Femoris, Quadratus Plantae (Layer 2), Rectus Femoris, Sartorius, Semimembranosus, Semimembranosus, Semitendinosus, Semitendinosus, Soleus & Achilles Tendon, Superior Extensor Retinaculum, Superior Gemelli, Tensor Fascia Lata, Tibialis Anterior, Tibialis Posterior, Transverse Intermuscular Septum, Vastus Intermedius, Vastus Lateralis, and Vastus Medialis.

28. The method of claim 26, wherein the Structure of interest includes at least one Structure selected from the group consisting of: Common Extensor Tendon: Extensor Carpi Ulnaris, Abductor Pollicis Longus, Acromioclavicular Ligaments, Adductor Pollicis, Anconeus, Annular Ligament, Biceps Brachii, Bicipital Aponeurosis, Brachialis, Brachioradialis, Common Extensor Tendon: Extensor Carpi Radialis Brevis, Common Extensor Tendon: Extensor Carpi Ulnaris, Common Extensor Tendon: Extensor Digiti Minimi, Common Extensor Tendon: Extensor Digitorum Communis, Coracoacromial Ligaments, Coracobrachialis, Deltoid (Anterior and Middle Fibers), Deltoid (Posterior Fibers), Dorsal and Palmar Interossei, Dorsal Ligaments (Radioulnar, Radiocarpal, Intercarpal), Extensor Carpi Radialis Longus, Extensor Indicis, Extensor Pollicis Brevis, Extensor Pollicis Longus, Extensor Retinaculum, Extensor Tendons with Expansions, Flexor Carpi Radialis, Flexor Carpi Ulnaris, Flexor Digitorum Profundus, Flexor Digitorum Superficialis (2 heads), Flexor Pollicis Longus, Flexor Retinaculum/ Transverse Carpal Ligament, Glenohumeral Joint Capsule, Hypothenar Muscles, Infraspinatus, Interosseus Membrane, Joint Capsules, Lateral Intermuscular Septum, Latissimus Dorsi Insertion (Distal 3rd), Lumbricals (Digits 2 & 3). Lumbricals (Digits 3 & 4), Medial Intermuscular Septum, Palmar Fascia, Palmar Ligaments (Radioulnar, Radiocarpal, Intercarpal), Palmaris Brevis, Palmaris Longus, Pectoralis Major, Pronator Quadratus, Pronator Teres, Quadrate Ligament, Radial Collateral Ligament of Elbow, Radial Collateral Ligament of Wrist, Serratus Anterior (Scapular Insertion), Subscapularis, Supinator and Arcade of Frohse, Supraspinatus, Teres Major, Teres Minor, Thenar Muscles, Triangular Fibrocartilage Disc, Triceps Brachii, Tunnel of Guyon, and Ulnar Collateral Ligament (UCL) Of Wrist.

29. The method of claim 26, wherein the Structure of interest includes at least one Structure selected from the group consisting of: Diaphragm, Erector Spinae (Iliocostalis, Longissimus, Spinalis), External Intercostals, Heart, Internal Intercostals, Interspinales (Cervical, Thoracic, Lumbar), Intertransversarii (Cervical, Thoracic, Lumbar), Latissimus Dorsi Origin, Levator Scapula, Levatores Costorum, Lung, Mamillary Tissue, Middle and Lower Fiber Trapezius, Multifidi (Cervical, Thoracic, Lumbar), Quadratus Lumborum, Rhomboids, Rotatores (Cervical, Thoracic, Lumbar), Semispinalis (Cervical, Thoracic, Lumbar), Serratus Anterior (Costal Origin), Serratus Posterior Inferior, Serratus Posterior Superior, Splenius (Capitus, Cervicis), Subclavius, Suboccipital: Obliquus Capitis Inferior, Suboccipital: Obliquus Capitis Superior, Suboccipital: Rectus Capitls Posterior Major, Suboccipital: Rectus Capitis Posterior Minor, Supraspinous/Nuchal Ligament, Supraspinous Ligament (Thoracic, Lumbar), Thoracolumbar Fascia, and Upper Fiber Trapezius.

30. The method of claim 26, wherein the Structure of interest includes at least one Structure selected from the group consisting of: Anterior Auricular, Anterior Scalene, Aryepiglottic, Brain, Buccinator, Ciliary Muscle, Coronalis, Corrugator Supercilii, Cricothyroid, Depressor Anguli Oris, Depressor Labii Inferioris, Digastric, Dilator Muscle, Epicranius, Frontolacrimalis, Frontomaxilaris, Frontonasalis, Frontozygomatica, Genioglossus, Geniohyoid, Hyoglossus, Inferior Longitudinal, Inferior Pharyngeal Constrictor, Lacrimomaxillaris Suture, Lambdoid Suture, Lateral Cricoarytenoid, Lateral Pterygoid, Levator Anguli Oris, Levator Labii Superiores Aleque Nasi, Levator Labii Superioris, Levator Palpebrae Superioris, Levator Veli Palati, Masseter, Medial Pterygoid, Mentalis, Middle Pharyngeal Constrictor, Middle Scalene, Musculus Uvulae, Mylohyoid, Nasalis, Nasomaxillaris Suture, Oblique Arytenoid, Occipitimastoid Suture, Omohyoid, Orbicularis Oculi, Orbicularis Oris, Palatoglossus, Palatoglossus, Palatopharyngeus, Parathyroid, Parietomastoid Suture, Parotid Gland, Platysma, porus acusticus externus, Posterior Auricular, Posterior Cricoarytenoid, Posterior Scalene, Procerus, Risorius, Salpingopharyngeus, Sphenofrontalis Suture, Sphenosquamosa Suture, Sphenozygomatic Suture, Sphincter Pupillae, Squamomastoid Suture, Squamous Suture, Stapedius, Sternocleidomastoid, Sternohyoid, Sternothyroid, Styloglossus, Stylohyoid, Stylopharyngeus, Superior Auricular, Superior Longitudinal, Superior Pharyngeal Constrictor, Superior Tarsal, Temporalis, Temporozygomatic Suture, Tensor Tympani, Tensor Veli Palati, Thyroarytenoid, Thyroepiglottic, Thyrohyoid, Thyroid, Transverse, Transverse Arytenoid, Vertical, Vocalis, Zygomaticomaxillaris Suture, Zygomaticus Major, and Zygomaticus Minor.

31. The method of claim 26, wherein the Structure of interest includes at least one Structure selected from the group consisting of: Abdominals: External Obliques, Abdominals: Internal Obliques, Abdominals: Rectus Abdominus, Abdominals: Transversus Abdominus, Anterior Sacral Ligaments, Appendix, Ascending Colon, Bladder, Bulbospongiosis External, Cecum, Coccygeal Ligament, Cremaster, Deep Transverse Perineal, Descending Colon, Duodenum, Esophagus, External Urethral Sphinter, Gall Bladder, Iliocecal Valve, Iliococcygeus (Levator Ani), Iliolumbar Ligament, Illium, Inguinal Ligament, Ischiocavernosis External, Ischiococcygeus, Jejunum, Kidneys, Levator Ani External, Liver, Mesentery, Mons Pubis, Obturator Internus (Proximal ⅓ Origin), Omentum, Ovaries, Pancreas, Posterior Sacral Ligaments, Prostate, Proximal Hamstrings Origin, Pubococcygeus (Levator Ani), Puborectalis (Levator Ani), Pyrimidalis, Rectum, Sacrospinous Ligament, Sacrotuberous Ligament, Sigmoid Colon, Sphinter Urethrae, Spleen, Stomach, Superficial Transverse Perineal, Transverse Colon, Transverse Perineal External, Uereters, Urethrovaginalis, and Uterus.

32. A method of preventing or treating reperfusion injury in a human body including steps of:
- consulting a system that organizes
  - images of taxonomically classified hand placement for treatment of reperfusion injury at one or more Structures of interest in a human body;
  - descriptive information associated with the hand placement as shown in the images as part of a framework of data demonstrating how to
    - activate treatment by creating a semi-occlusive manual tourniquet at an artery that supplies blood to the one or more Structures of interest;
    - stretch a portion of the human body to occlude blood flow to a nerve segment of the human body by elongation of the nerve segment proximate the one or more Structures of interest; and
  - rules that facilitate selection of the taxonomically classified images and the descriptive information;
- the one or more Structures of interest being parts of the human body that are proximate a site which is susceptible to reperfusion injury,
- the one or more Structures of interest being selected from the group consisting of muscles, tendons, ligaments, fascia, skin, fibrous tissues, connective tissue, fat, synovial membranes, nerves, blood vessels, glands, ducts, organs, and combinations thereof;
- touching the one or more Structures of interest to attract blood flow;
- activating occlusive treatment by creating a semi-occlusive manual tourniquet at an artery that supplies blood to one or more Structures of interest in a body,
- ascertaining effectiveness of the semi-occlusive manual tourniquet by determining a shift in volume and/or rate of a pulse at the hand placement; and
- stretching a portion of the human body to occlude blood flow to a nerve segment of the human body by elongation of the nerve segment proximate to the Structure of interest.

33. The method of claim 32, wherein the Structure of interest includes at least one Structure selected from the group consisting of: Abductor Digiti Minimi (Layer 1), Abductor Hallucis (Layer 1), Adductor Brevis, Adductor Hallucis (Layer 3), Adductor Longus, Adductor Magnus, Anterior Cruciate Ligament, Articularis Genu, Biceps Femoris(Long Head), Biceps Femoris (Long Head), Biceps Femoris(Short Head), Dorsal Interossei, Extensor Digitorum Brevis & Extensor Hallucis Brevis, Extensor Digitorum Longus, Extensor Hallucis Longus, Flexor Digiti Minimi & Opponens Digiti Minimi (Layer 3), Flexor Digitorum Brevis (Layer 1), Flexor Digitorum Longus, Flexor Hallucis Brevis (Layer3), Flexor Hallucis Longus, Flexor Retinaculum, Gastrocnemius & Achilles Tendon, Gluteus Maximus, Gluteus Medius, Gluteus Minimus, Gracilis, Iliacus, Iliotibial Band, Inferior Extensor Retinaculum, Inferior Gemelli, Interosseus Membrane of Leg, Joint Capsules, Lateral Collateral Ligament of Ankle, Lateral Collateral Ligament of Knee, Lateral Meniscus, Lumbricals (Layer 2), Medial Collateral Ligament of Knee, Medial Collateral Ligaments of Ankle (Deltoid Ligament), Medial Meniscus, Obturator Externus, Obturator Internus Distal ⅔ (Insertion)m Patellar Ligament, Pectineus, Peroneus Brevis, Peroneus Longus, Peroneus Tertius, Piriformis, Plantar Calcaneonavicular Ligament (Spring Ligament), Plantar Fascia, Plantar Interossei (Layer 4), Plantaris, Plica, Popliteus, Posterior Cruciate Ligament, Psoas Major, Psoas Minor, Quadratus Femoris, Quadratus Plantae (Layer 2), Rectus Femoris, Sartorius, Semimembranosus, Semimembranosus, Semitendinosus, Semitendinosus, Soleus & Achilles Tendon, Superior Extensor Retinaculum, Superior Gemelli, Tensor Fascia Lata, Tibialis Anterior, Tibialis Posterior, Transverse Intermuscular Septum, Vastus Intermedius, Vastus Lateralis, and Vastus Medialis.

34. The method of claim 32, wherein the Structure of interest includes at least one Structure selected from the group consisting of: Common Extensor Tendon: Extensor Carpi Ulnaris, Abductor Pollicis Longus, Acromioclavicular Ligaments, Adductor Pollicis, Anconeus, Annular Ligament, Biceps Brachii, Bicipital Aponeurosis, Brachialis, Brachioradialis, Common Extensor Tendon: Extensor Carpi Radialis Brevis, Common Extensor Tendon: Extensor Carpi Ulnaris, Common Extensor Tendon: Extensor Digiti Minimi, Common Extensor Tendon: Extensor Digitorum Communis, Coracoacromial Ligaments, Coracobrachialis, Deltoid (Anterior and Middle Fibers), Deltoid (Posterior Fibers), Dorsal and Palmar Interossei, Dorsal Ligaments (Radioulnar, Radiocarpal, Intercarpal), Extensor Carpi Radialis Longus, Extensor Indicis, Extensor Pollicis Brevis, Extensor Pollicis Longus, Extensor Retinaculum, Extensor Tendons with Expansions, Flexor Carpi Radialis, Flexor Carpi Ulnaris, Flexor Digitorum Profundus, Flexor Digitorum Superficialis (2 heads), Flexor Pollicis Longus, Flexor Retinaculum/ Transverse Carpal Ligament, Glenohumeral Joint Capsule, Hypothenar Muscles, Infraspinatus, Interosseus Membrane, Joint Capsules, Lateral Intermuscular Septum, Latissimus Dorsi Insertion (Distal 3rd), Lumbricals (Digits 2 & 3). Lumbricals (Digits 3 & 4), Medial Intermuscular Septum, Palmar Fascia, Palmar Ligaments (Radioulnar, Radiocarpal, Intercarpal), Palmaris Brevis, Palmaris Longus, Pectoralis Major, Pronator Quadratus, Pronator Teres, Quadrate Ligament, Radial Collateral Ligament of Elbow, Radial Collateral Ligament of Wrist, Serratus Anterior (Scapular Insertion), Subscapularis, Supinator and Arcade of Frohse, Supraspinatus, Teres Major, Teres Minor, Thenar Muscles, Triangular Fibrocartilage Disc, Triceps Brachii, Tunnel of Guyon, and Ulnar Collateral Ligament (UCL) Of Wrist.

35. The method of claim 32, wherein the Structure of interest includes at least one Structure selected from the group consisting of: Diaphragm, Erector Spinae (Iliocostalis, Longissimus, Spinalis), External Intercostals, Heart, Internal Intercostals, Interspinales (Cervical, Thoracic, Lumbar), Intertransversarii (Cervical, Thoracic, Lumbar), Latissimus Dorsi Origin, Levator Scapula, Levatores Costorum, Lung, Mamillary Tissue, Middle and Lower Fiber Trapezius, Multifidi (Cervical, Thoracic, Lumbar), Quadratus Lumborum, Rhomboids, Rotatores (Cervical, Thoracic, Lumbar), Semispinalis (Cervical, Thoracic, Lumbar), Serratus Anterior (Costal Origin), Serratus Posterior Inferior, Serratus Posterior Superior, Splenius (Capitus, Cervicis), Subclavius, Suboccipital: Obliquus Capitis Inferior, Suboccipital: Obliquus Capitis Superior, Suboccipital: Rectus Capitls Posterior Major, Suboccipital: Rectus Capitis Posterior Minor, Supraspinous/Nuchal Ligament, Supraspinous Ligament (Thoracic, Lumbar), Thoracolumbar Fascia, and Upper Fiber Trapezius.

36. The method of claim 32, wherein the Structure of interest includes at least one Structure selected from the group consisting of: Anterior Auricular, Anterior Scalene, Aryepiglottic, Brain, Buccinator, Ciliary Muscle, Coronalis, Corrugator Supercilii, Cricothyroid, Depressor Anguli Oris, Depressor Labii Inferioris, Digastric, Dilator Muscle, Epicranius, Frontolacrimalis, Frontomaxilaris, Frontonasali s, Frontozygomatica, Genioglossus, Geniohyoid, Hyoglossus, Inferior Longitudinal, Inferior Pharyngeal Constrictor, Lacrimomaxillaris Suture, Lambdoid Suture, Lateral Cricoarytenoid, Lateral Pterygoid, Levator Anguli Oris, Levator Labii Superiores Aleque Nasi, Levator Labii Superioris, Levator Palpebrae Superioris, Levator Veli Palati, Masseter, Medial Pterygoid, Mentalis, Middle Pharyngeal Constrictor, Middle Scalene, Musculus Uvulae, Mylohyoid, Nasalis, Nasomaxillari s Suture, Oblique Arytenoid, Occipitimastoid Suture, Omohyoid, Orbicularis Oculi, Orbicularis Oris, Palatoglossus, Palatoglossus, Palatopharyngeus, Parathyroid, Parietomastoid Suture, Parotid Gland, Platysma, porus acusticus externus, Posterior Auricular, Posterior Cricoarytenoid, Posterior Scalene, Procerus, Risorius, Salpingopharyngeus, Sphenofrontalis Suture, Sphenosquamosa Suture, Sphenozygomatic Suture, Sphincter Pupillae, Squamomastoid Suture, Squamous Suture, Stapedius, Sternocleidomastoid, Sternohyoid, Sternothyroid, Styloglossus, Stylohyoid, Stylopharyngeus, Superior Auricular, Superior Longitudinal, Superior Pharyngeal Constrictor, Superior Tarsal, Temporalis, Temporozygomatic Suture, Tensor Tympani, Tensor Veli Palati, Thyroarytenoid, Thyroepiglottic, Thyrohyoid, Thyroid, Transverse, Transverse Arytenoid, Vertical, Vocalis, Zygomaticomaxillaris Suture, Zygomaticus Major, and Zygomaticus Minor.

37. The method of claim 32, wherein the Structure of interest includes at least one Structure selected from the group consisting of: Abdominals: External Obliques, Abdominals: Internal Obliques, Abdominals: Rectus Abdominus, Abdominals: Transversus Abdominus, Anterior Sacral Ligaments, Appendix, Ascending Colon, Bladder, Bulbospongiosis External, Cecum, Coccygeal Ligament, Cremaster, Deep Transverse Perineal, Descending Colon, Duodenum, Esophagus, External Urethral Sphinter, Gall Bladder, Iliocecal Valve, Iliococcygeus (Levator Ani), Iliolumbar Ligament, Illium, Inguinal Ligament, Ischiocavernosis External, Ischiococcygeus, Jejunum, Kidneys, Levator Ani External, Liver, Mesentery, Mons Pubis, Obturator Internus (Proximal ⅓ Origin), Omentum, Ovaries, Pancreas, Posterior Sacral Ligaments, Prostate, Proximal Hamstrings Origin, Pubococcygeus (Levator Ani), Puborectalis (Levator Ani), Pyrimidalis, Rectum, Sacrospinous Ligament, Sacrotuberous Ligament, Sigmoid Colon, Sphinter Urethrae, Spleen, Stomach, Superficial Transverse Perineal, Transverse Colon, Transverse Perineal External, Uereters, Urethrovaginalis, and Uterus.

38. A computer readable form comprising:
data including
images of taxonomically classified hand placement for treatment of reperfusion injury at one or more Structures of interest in a human body;
descriptive information associated with the hand placement as shown in the images as part of a framework of data demonstrating how to
activate treatment by creating a semi-occlusive manual tourniquet at an artery that supplies blood to the one or more Structures of interest;
stretch a portion of the human body to occlude blood flow to a nerve segment of the human body by elongation of the nerve segment proximate the one or more Structures of interest and
rules that facilitate selection of the taxonomically classified images and the descriptive information;
the one or more Structures of interest being parts of the human body that are proximate a site which is susceptible to reperfusion injury, and
the one or more Structures of interest being selected from the group consisting of muscles, tendons, ligaments, fascia, skin, fibrous tissues, connective tissue, fat, synovial membranes, nerves, blood vessels, glands, ducts, organs, and combinations thereof.

39. The computer readable form of claim 38, wherein the Structure of interest includes at least one Structure selected from the group consisting of: Abductor Digiti Minimi (Layer 1), Abductor Hallucis (Layer 1), Adductor Brevis, Adductor Hallucis (Layer 3), Adductor Longus, Adductor Magnus, Anterior Cruciate Ligament, Articularis Genu, Biceps Femoris(Long Head), Biceps Femoris (Long Head), Biceps Femoris(Short Head), Dorsal Interossei, Extensor Digitorum Brevis & Extensor Hallucis Brevis, Extensor Digitorum Longus, Extensor Hallucis Longus, Flexor Digiti Minimi & Opponens Digiti Minimi (Layer 3), Flexor Digitorum Brevis (Layer 1), Flexor Digitorum Longus, Flexor Hallucis Brevis (Layer3), Flexor Hallucis Longus, Flexor Retinaculum, Gastrocnemius & Achilles Tendon, Gluteus Maximus, Gluteus Medius, Gluteus Minimus, Gracilis, Iliacus, Iliotibial Band, Inferior Extensor Retinaculum, Inferior Gemelli, Interosseus Membrane of Leg, Joint Capsules, Lateral Collateral Ligament of Ankle, Lateral Collateral Ligament of Knee, Lateral Meniscus, Lumbricals (Layer 2), Medial Collateral Ligament of Knee, Medial Collateral Ligaments of Ankle (Deltoid Ligament), Medial Meniscus, Obturator Externus, Obturator Internus Distal ⅔ (Insertion)m Patellar Ligament, Pectineus, Peroneus Brevis, Peroneus Longus, Peroneus Tertius, Piriformis, Plantar Calcaneonavicular Ligament (Spring Ligament), Plantar Fascia, Plantar Interossei (Layer 4), Plantaris, Plica, Popliteus, Posterior Cruciate Ligament, Psoas Major, Psoas Minor, Quadratus Femoris, Quadratus Plantae (Layer 2), Rectus Femoris, Sartorius, Semimembranosus, Semimembranosus, Semitendinosus, Semitendinosus, Soleus & Achilles Tendon, Superior Extensor Retinaculum, Superior Gemelli, Tensor Fascia Lata, Tibialis Anterior, Tibialis Posterior, Transverse Intermuscular Septum, Vastus Intermedius, Vastus Lateralis, and Vastus Medialis.

40. The computer readable form of claim 38, wherein the Structure of interest includes at least one Structure selected from the group consisting of: Common Extensor Tendon: Extensor Carpi Ulnaris, Abductor Pollicis Longus, Acromioclavicular Ligaments, Adductor Pollicis, Anconeus, Annular Ligament, Biceps Brachii, Bicipital Aponeurosis, Brachialis, Brachioradialis, Common Extensor Tendon: Extensor Carpi Radialis Brevis, Common Extensor Tendon: Extensor Carpi Ulnaris, Common Extensor Tendon: Extensor Digiti Minimi, Common Extensor Tendon: Extensor Digitorum Communis, Coracoacromial Ligaments, Coracobrachialis, Deltoid (Anterior and Middle Fibers), Deltoid (Posterior Fibers), Dorsal and Palmar Interossei, Dorsal Ligaments (Radioulnar, Radiocarpal, Intercarpal), Extensor Carpi Radialis Longus, Extensor Indicis, Extensor Pollicis Brevis, Extensor Pollicis Longus, Extensor Retinaculum, Extensor Tendons with Expansions, Flexor Carpi Radialis, Flexor Carpi Ulnaris, Flexor Digitorum Profundus, Flexor Digitorum Superficialis (2 heads), Flexor Pollicis Longus, Flexor Retinaculum/Transverse Carpal Ligament, Glenohumeral Joint Capsule, Hypothenar Muscles, Infraspinatus, Interosseus Membrane, Joint Capsules, Lateral Intermuscular Septum, Latissimus Dorsi Insertion (Distal 3rd), Lumbricals (Digits 2 & 3). Lumbricals (Digits 3 & 4), Medial Intermuscular Septum, Palmar Fascia, Palmar Ligaments (Radioulnar, Radiocarpal, Intercarpal), Palmaris Brevis, Palmaris Longus, Pectoralis Major, Pronator Quadratus, Pronator Teres, Quadrate Ligament, Radial Collateral Ligament of Elbow, Radial Collateral Ligament of Wrist, Serratus Anterior (Scapular Insertion), Subscapularis, Supinator and Arcade of Frohse, Supraspinatus, Teres Major, Teres Minor, Thenar Muscles, Triangular Fibrocartilage Disc, Triceps Brachii, Tunnel of Guyon, and Ulnar Collateral Ligament (UCL) Of Wrist.

41. The method of claim 38, wherein the Structure of interest includes at least one Structure selected from the group consisting of: Diaphragm, Erector Spinae (Iliocostalis, Longissimus, Spinalis), External Intercostals, Heart, Internal Intercostals, Interspinales (Cervical, Thoracic, Lumbar), Intertransversarii (Cervical, Thoracic, Lumbar), Latissimus Dorsi Origin, Levator Scapula, Levatores Costorum, Lung, Mamillary Tissue, Middle and Lower Fiber Trapezius, Multifidi (Cervical, Thoracic, Lumbar), Quadratus Lumborum, Rhomboids, Rotatores (Cervical, Thoracic, Lumbar), Semispinalis (Cervical, Thoracic, Lumbar), Serratus Anterior (Costal Origin), Serratus Posterior Inferior, Serratus Posterior Superior, Splenius (Capitus, Cervicis), Subclavius, Suboccipital: Obliquus Capitis Inferior, Suboccipital: Obliquus Capitis Superior, Suboccipital: Rectus Capitls Posterior Major, Suboccipital: Rectus Capitis Posterior Minor, Supraspinous/Nuchal Ligament, Supraspinous Ligament (Thoracic, Lumbar), Thoracolumbar Fascia, and Upper Fiber Trapezius.

42. The computer readable form of claim 38, wherein the Structure of interest includes at least one Structure selected from the group consisting of: Anterior Auricular, Anterior Scalene, Aryepiglottic, Brain, Buccinator, Ciliary Muscle, Coronalis, Corrugator Supercilii, Cricothyroid, Depressor Anguli Oris, Depressor Labii Inferioris, Digastric, Dilator Muscle, Epicranius, Frontolacrimalis, Frontomaxilaris, Frontonasali s, Frontozygomatica, Genioglossus, Geniohyoid, Hyoglossus, Inferior Longitudinal, Inferior Pharyngeal Constrictor, Lacrimomaxillaris Suture, Lambdoid Suture, Lateral Cricoarytenoid, Lateral Pterygoid, Levator Anguli Oris, Levator Labii Superiores Aleque Nasi, Levator Labii Superioris, Levator Palpebrae Superioris, Levator Veli Palati, Masseter, Medial Pterygoid, Mentalis, Middle Pharyngeal Constrictor, Middle Scalene, Musculus Uvulae, Mylohyoid, Nasalis, Nasomaxillaris Suture, Oblique Arytenoid, Occipitimastoid Suture, Omohyoid, Orbicularis Oculi, Orbicularis Oris, Palatoglossus, Palatoglossus, Palatopharyngeus, Parathyroid, Parietomastoid Suture, Parotid Gland, Platysma, porus acusticus externus, Posterior Auricular, Posterior Cricoarytenoid, Posterior Scalene, Procerus, Risorius, Salpingopharyngeus, Sphenofrontalis Suture, Sphenosquamosa Suture, Sphenozygomatic Suture, Sphincter Pupillae, Squamomastoid Suture, Squamous Suture, Stapedius, Sternocleidomastoid, Sternohyoid, Sternothyroid, Styloglossus, Stylohyoid, Stylopharyngeus, Superior Auricular, Superior Longitudinal, Superior Pharyngeal Constrictor, Superior Tarsal, Temporalis, Temporozygomatic Suture, Tensor Tympani, Tensor Veli Palati, Thyroarytenoid, Thyroepiglottic, Thyrohyoid, Thyroid, Transverse, Transverse Arytenoid, Vertical, Vocalis, Zygomaticomaxillaris Suture, Zygomaticus Major, and Zygomaticus Minor.

43. The computer readable form of claim 38, wherein the Structure of interest includes at least one Structure selected from the group consisting of: Abdominals: External Obliques, Abdominal s: Internal Obliques, Abdominals: Rectus Abdominus, Abdominals: Transversus Abdominus, Anterior Sacral Ligaments, Appendix, Ascending Colon, Bladder, Bulbospongiosis External, Cecum, Coccygeal Ligament, Cremaster, Deep Transverse Perineal, Descending Colon, Duodenum, Esophagus, External Urethral Sphinter, Gall Bladder, Iliocecal Valve, Iliococcygeus (Levator Ani), Iliolumbar Ligament, Illium, Inguinal Ligament, Ischiocavernosis External, Ischiococcygeus, Jejunum, Kidneys, Levator Ani External, Liver, Mesentery, Mons Pubis, Obturator Internus (Proximal ⅓ Origin), Omentum, Ovaries, Pancreas, Posterior Sacral Ligaments, Prostate, Proximal Hamstrings Origin, Pubococcygeus (Levator Ani), Puborectalis (Levator Ani), Pyrimidalis, Rectum, Sacrospinous Ligament, Sacrotuberous Ligament, Sigmoid Colon, Sphinter Urethrae, Spleen, Stomach, Superficial Transverse Perineal, Transverse Colon, Transverse Perineal External, Uereters, Urethrovaginalis, and Uterus.

\* \* \* \* \*

UNITED STATES PATENT AND TRADEMARK OFFICE
CERTIFICATE OF CORRECTION

PATENT NO. : 10,786,424 B1
APPLICATION NO. : 16/045201
DATED : September 29, 2020
INVENTOR(S) : Vinita Chandra-Mody It is certified that error appears in the above-identified patent and that said Letters Patent is hereby corrected as shown below:

In the Claims

Column 42, Line 60 the text "Distal 2/3 (Insertion)m Patellar" should be -- Distal 2/3 (Insertion) Patellar --

Column 42, Line 66-67-Line 1 the text "...Sartorius, Semimembranosus, Semimembranosus, Semitendinosus, Semitendinosus, Soleus" should be -- Sartorius, Semimembranosus, Semitendinosus, Soleus --

Column 45, Line 15 the text "Distal 2/3 (Insertion)m Patellar" should be -- Distal 2/3 (Insertion) Patellar --

Column 45, Line 49 the text "(Digits 2 & 3)." should be -- (Digits 2 & 3), --

Column 46, Line 30 the text "Palatoglossus, Palatoglossus, Palatophryngeus," should be -- Palatoglossus, Palatophryngeus, --

Column 47, Line 60 the text "Distal 2/3 (Insertion)m Patellar" should be -- Distal 2/3 (Insertion) Patellar --

Column 49, Line 5 the text "Nasomaxillari s Suture," should be -- Nasomaxillaris Suture --

Column 49, Line 7 the text "Palatoglossus, Palatoglossus, Palatopharyngeius," should be -- Palatoglossus, Palatopharyngeius, --

Column 50, Lines 6-7 the text "Biceps Femoris(Long Head), Biceps Femoris (Long Head), Biceps" should be -- Biceps Femoris(Long Head), Biceps --

Column 50, Line 22 the text "Distal 2/3 (Insertion)m Patellar" should be -- Distal 2/3 (Insertion) Patellar --

Signed and Sealed this
Fifth Day of July, 2022

Katherine Kelly Vidal
*Director of the United States Patent and Trademark Office*

CERTIFICATE OF CORRECTION (continued)
U.S. Pat. No. 10,786,424 B1

Column 51, Line 27 the text "Frontonasali s, Frontozygomatica," should be changed to
-- Frontonasalis, Frontozygomatica, --

Column 52, Line 19 the text "Abdominal s: Internal" should be changed to -- Abdominals: Internal --